(12) United States Patent
Lee et al.

(10) Patent No.: US 11,473,127 B2
(45) Date of Patent: Oct. 18, 2022

(54) ANALYTICAL SIGNAL FOR DETERMINATION OF THE PRESENCE OF A TARGET NUCLEIC ACID SEQUENCE

(71) Applicant: SEEGENE, INC., Seoul (KR)

(72) Inventors: Young Jo Lee, Seoul (KR); Han Bit Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 216 days.

(21) Appl. No.: 16/498,157

(22) PCT Filed: Mar. 27, 2018

(86) PCT No.: PCT/KR2018/003590
§ 371 (c)(1),
(2) Date: Sep. 26, 2019

(87) PCT Pub. No.: WO2018/182281
PCT Pub. Date: Oct. 4, 2018

(65) Prior Publication Data
US 2021/0102236 A1 Apr. 8, 2021

(30) Foreign Application Priority Data

Mar. 28, 2017 (KR) .................. 10-2017-0039306

(51) Int. Cl.
*C12Q 1/682* (2018.01)
*G16B 25/20* (2019.01)

(52) U.S. Cl.
CPC ............. *C12Q 1/682* (2013.01); *G16B 25/20* (2019.02)

(58) Field of Classification Search
CPC ................ C12Q 1/682; C12Q 1/6851; C12Q 2527/101; C12Q 2547/101; C12Q 2561/113; C12Q 2563/107; G16B 25/20
See application file for complete search history.

(56) References Cited

U.S. PATENT DOCUMENTS

2017/0362646 A1* 12/2017 Chun ..................... G16B 30/00

FOREIGN PATENT DOCUMENTS

| KR | 10-2016-0126092 A | 11/2016 |
| WO | WO-2013115442 A1 | 8/2013 |
| WO | WO-2014176575 A1 | 10/2014 |
| WO | WO-2015/147412 A1 | 10/2015 |
| WO | WO-2015147412 A1 | 10/2015 |
| WO | WO-2016/052991 A1 | 4/2016 |
| WO | WO-2016/093620 A1 | 6/2016 |
| WO | WO-2016093619 A1 | 6/2016 |
| WO | WO-2017105104 A1 | 6/2017 |

OTHER PUBLICATIONS

Chakravorty, et al. (2011) "Rapid Detection of Fluoroquinolone-Resistant and Heteroresistant *Mycobacterium tuberculosis* by Use of Sloppy Molecular Beacons and Dual Melting-Temperature Codes in a Real-Time PCR Assay." *Journal of Clinical Microbiology*, Mar. 2011, 49(3):932-940.
Liu, et al. (2013) "Triplex real-time PCR melting curve analysis for detecting *Mycobacterium tuberculosis* mutations associated with resistance to second-line drugs in a single reaction." *J Antimicrob Chemother*, Jan. 2013; 68:1097-1103.
International Search Report (ISR) from corresponding PCT Application No. PCTKR2018003590, dated Aug. 3, 2018.
Sanchez J Aquiles et al., BMC Biotechnology, Biomed Central Ltd, vol. 6, No. 44, Dec. 4, 2006, pp. 1-14.

\* cited by examiner

*Primary Examiner* — David C Thomas
(74) *Attorney, Agent, or Firm* — Harness, Dickey & Pierce, P.L.C.

(57) ABSTRACT

The present invention relates to a method for providing an analytical signal for determination of the presence of a target nucleic acid sequence in a sample. The present invention can contribute to dramatic improvement in methods for detecting target nucleic acid sequences using different detection temperatures and reference values. The present invention allows detection of a target nucleic acid sequence in a more accurate, effective and reproducible manner, by removing or adjusting a signal region that may affect the detection of a target nucleic acid sequence.

17 Claims, 23 Drawing Sheets

Specification includes a Sequence Listing.

ANALYTICAL SIGNAL FOR DETERMINATION OF THE PRESENCE OF A TARGET NUCLEIC ACID SEQUENCE

CROSS-REFERENCE TO RELATED APPLICATIONS

This application is a national phase application of PCT Application No. PCT/KR2018/003590, filed on Mar. 27, 2018, which claims the benefit and priority to Korean Patent Application No. 10-2017-0039306, filed Mar. 28, 2017. The entire disclosures of the applications identified in this paragraph are incorporated herein by references.

FIELD

The present invention relates to a method for providing an analytical signal for determination of the presence of a target nucleic acid sequence from signals detected at a relatively high detection temperature and at a relatively low detection temperature.

BACKGROUND

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences include Molecular beacon method using dual-labeled probes with hairpin structure (Tyagi et al, Nature Biotechnology v. 14 March 1996), HyBeacon method (French D J et al., Mol. Cell Probes, 15(6):363-374 (2001)), Hybridization probe method using two probes labeled each of donor and acceptor (Bernad et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers include Sunrise primer method (Nazarenko et al, 2516-2521 Nucleic Acids Research, 1997, v. 25 no. 12, and U.S. Pat. No. 6,117,635), Scorpion primer method (Whitcombe et al, 804-807, Nature Biotechnology v. 17 August 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO cleavage AND extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (WO 2014/104818).

The conventional real-time detection technologies described above detect signals generated from fluorescent labels at a selected detection temperature in signal amplification process associated with or with no target amplification. When a plurality of target nucleic acid sequences using a single type of label in a single reaction tube are detected in accordance with the conventional real-time detection technologies, generated signals for target nucleic acid sequences are not differentiated from each other. Therefore, the conventional real-time detection technologies generally employ different types of labels for detecting a plurality of target nucleic acid sequences. The melting analysis using Tm difference permits to detect a plurality of target nucleic acid sequences even using a single type of label. However, the melting analysis has serious shortcomings in that its performance time is longer than real-time technologies and design of probes with different Tm values becomes more difficult upon increasing target sequences.

Accordingly, where novel methods or approaches being not dependent on melting analysis for detecting a plurality of target nucleic acid sequences using a single type of label in a single reaction vessel and a single type of detector are developed, they enable to detect a plurality of target nucleic acid sequences with dramatically enhanced convenience, cost-effectiveness and efficiency. In addition, the combination of the novel methods with other detection methods (e.g., melting analysis) would also result in detection of a plurality of target nucleic acid sequences using a single type of label in a single reaction vessel with dramatically enhanced efficiency.

To this end, the present inventors have disclosed a method for detecting a plurality of target nucleic acid sequences using a single type of detector in a single reaction vessel (WO 2015/147412). According to the method, the presence of the target nucleic acid sequence having a relatively low detection temperature can be determined by a difference between the signal detected at a relatively high detection temperature and the signal detected at a relatively low detection temperature. Particularly, based on the finding that the intensities of signals at the relatively low detection temperature and the relatively high detection temperature are different from each other, the present inventors have introduced a reference value representing a relationship of change in signals at different detection temperatures to obtain the difference between signals at the relatively high detection temperature and at the relatively low detection temperature.

Typically, the reference value is predetermined by acquiring a certain range of values via repetitive experiments using a control sample containing only a target nucleic acid sequence having a relatively high detection temperature and then selecting a suitable one among the acquired values. It has been observed, however, that selection of inappropriate reference value may lead to erroneous results in some reactions.

Accordingly, for being free from such erroneous results, there is an urgent need to develop a novel method for providing an analytical signal for determination of the presence of a target nucleic acid sequence in much more accurate manner.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY

Accordingly, it is an object of this invention to provide a method for providing an analytical signal for determination of the presence of a target nucleic acid sequence.

It is another object of this invention to provide a computer readable storage medium containing instructions to configure a processor to perform a method for providing an analytical signal for determination of the presence of a target nucleic acid sequence.

It is still another object of this invention to provide a device for providing an analytical signal for determination of the presence of a target nucleic acid sequence.

It is further object of this invention to provide a computer program to be stored on a computer readable storage medium to configure a processor to perform a method for providing an analytical signal for determination of the presence of a target nucleic acid sequence.

Other objects and advantages of the present invention will become apparent from the detailed description to follow taken in conjugation with the appended claims and drawings.

DETAILED DESCRIPTION

Figure 1:
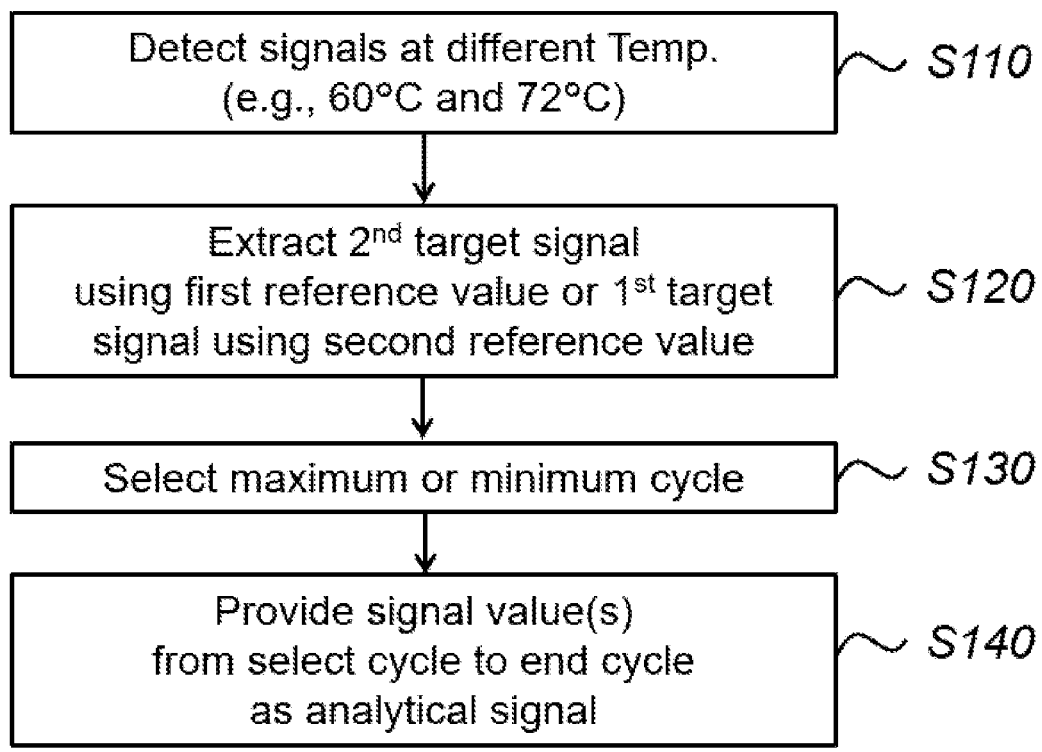
FIGS. 1, 2, 3 and 4 are flow charts representing embodiments of this invention 100, 200, 300 and 400 for providing an analytical signal for determination of the presence of a target nucleic acid sequence.

I. Provision of an Analytical Signal for Determination of the Presence of a Target Nucleic Acid Sequence In one aspect of this invention, there is provided a method for providing an analytical signal for determination of the presence of a target nucleic acid sequence in a sample, comprising:

(a) incubating the sample with a first signal-generating means capable of generating a signal for a first target nucleic acid sequence and a second signal-generating means capable of generating a signal for a second target nucleic acid sequence in a single reaction vessel and detecting signals at a relatively high detection temperature and a relatively low detection temperature by a single type of detector; wherein the incubation is performed by a signal-generating process; wherein the detection is performed at one or more cycles of the signal-generating process to obtain a signal value at each of the one or more cycles; wherein the two signals to be generated by the two signal-generating means are not differentiated by the single type of detector;

(b) processing the signal values obtained in the step (a) by using a second reference value to extract the signal for the first target nucleic acid sequence or processing the signal values obtained in the step (a) by using a first reference value to extract the signal for the second target nucleic acid sequence; wherein the first reference value is a value representing a relationship of change in signals provided by the first signal-generating means at the relatively high detection temperature and the relatively low detection temperature, and the second reference value is a value representing a relationship of change in signals provided by the second signal-generating means at the relatively high detection temperature and the relatively low detection temperature; wherein the first reference value is determined from a control reaction using the first target nucleic acid sequence and the first signal-generating means and the second reference value is determined from a control reaction using the second target nucleic acid sequence and the second signal-generating means;

(c) selecting a cycle having a maximum signal value or a minimum signal value in the extracted signal for the first target nucleic acid sequence or the second target nucleic acid sequence; and (d) providing a signal value(s) from the selected cycle to an end cycle as an analytical signal for determination of the presence of the first target nucleic acid sequence or the second target nucleic acid sequence.

The present invention will be described in more detail with reference to the flow charts of FIGS. 1 to 4 as follows:

Step (a): Incubation and Signal Detection (S110; S210; S310; S410)

In step (a), the sample is incubated with a first signal-generating means capable of generating a signal for a first target nucleic acid sequence and a second signal-generating means capable of generating a signal for a second target nucleic acid sequence in a single reaction vessel. Afterwards, signals at a relatively high detection temperature and a relatively low detection temperature are detected by a single type of detector.

The term "sample" as used herein refers to any material undergoing the method of the present invention. Particularly, the term "sample" refers to any material containing or presumed to contain a nucleic acid of interest (one or both of a first target nucleic acid sequence and a second target nucleic acid sequence) or which is itself a nucleic acid containing or presumed to contain a target nucleic acid sequence of interest. More particularly, the term "sample" as used herein includes biological samples (e.g., cells, tissues, and fluid from a biological source) and non-biological samples (e.g., food, water and soil). The biological samples includes, but not limited to, virus, bacteria, tissue, cell, blood, serum, plasma, lymph, sputum, swab, aspirate, bronchoalveolar lavage fluid, milk, urine, feces, ocular fluid, saliva, semen, brain extracts, spinal cord fluid (SCF), appendix, spleen and tonsillar tissue extracts, amniotic fluid and ascitic fluid. In addition, the sample may include natural-occurring nucleic acid molecules isolated from biological sources and synthetic nucleic acid molecules. The samples herein include those subjected or not subjected to a nucleic acid extraction process.

The term used herein "target nucleic acid", "target nucleic acid sequence" or "target sequence" refers to a nucleic acid sequence of interest for analysis, detection or quantification. The target nucleic acid sequence comprises a sequence in a single strand as well as in a double strand. The target nucleic acid sequence comprises a sequence newly generated in reactions as well as a sequence initially present in a sample.

The target nucleic acid sequence may include any DNA (gDNA and cDNA), RNA molecules and their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature.

The target nucleic acid sequence should not be construed as limiting the sequence known at a given time or the sequence available as of a given time, but instead should be read to encompass the sequence that may be available or known now or at any time in the future. In other words, the target nucleic acid sequence may or may not be known at the time of practicing the present method. In case of unknown target nucleic acid, its sequence may be determined by one of conventional sequencing methods prior to performing the present method.

Two target nucleic acid sequences usable in the present invention comprise the first target nucleic acid sequence and the second target nucleic acid sequence. The terms "first target nucleic acid sequence" and "second target nucleic acid sequence" are used herein to distinguish two different target nucleic acid sequences. For instance, the first target nucleic acid sequence and the second target nucleic acid sequence may be two different genes, two different gene regions or two different DNA sequences of interest. Particularly, the first target nucleic acid sequence may be derived from one organism, whereas the second target nucleic acid sequence from another organism.

According to an embodiment of this invention, one of the two target nucleic acid sequences comprise a nucleotide variation, or one of the two target nucleic acid sequences comprises one type of the nucleotide variation and the other comprises the other type of the nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term "nucleotide variation" used herein includes any variation at a particular location in a nucleic acid sequence. In other words, the term "nucleotide variation" includes a wild type and its any mutant type at a particular location in a nucleic acid sequence.

According to the present invention, the sample (or target nucleic acid sequences in the sample) is incubated with two signal-generating means in order to obtain signals for the target nucleic acid sequences.

The term "incubating," "incubate," or "incubation" as used herein refers to bring components together for their interaction or reaction. Particularly, the term refers to subjecting the components herein to a signal-generating process.

The term "signal" as used herein refers to a measurable output.

The signal change may serve as an indicator indicating qualitatively or quantitatively the presence or absence of an analyte (a target nucleic acid sequence).

Examples of useful indicators include fluorescence intensity, luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The most widely used indicator is fluorescence intensity.

Signals include various signal characteristics from the signal detection, e.g., signal intensity [e.g., RFU (relative fluorescence unit) value or in the case of performing amplification, RFU values at a certain cycle, at selected cycles or at end-point], signal change shape (or pattern) or Ct value, or values obtained by mathematically processing the characteristics.

According to an embodiment, the term "signal" with conjunction with reference value or sample analysis includes not only signals per se obtained at detection temperatures but also a modified signal provided by mathematically processing the signals.

According to an embodiment of this invention, when an amplification curve is obtained by real-time PCR, various signal values (or characteristics) from the amplification curve may be selected and used for determination of target presence (intensity, $C_t$ value or amplification curve data).

The terms "signal for a first target nucleic acid sequence" and "signal for a second target nucleic acid sequence" as used herein refer to signals representing the first target nucleic acid sequence and the second target nucleic acid sequence, respectively. A significant level of the signal for a first target nucleic acid sequence or second target nucleic acid sequence indicates the presence of the first target nucleic acid sequence or the second target nucleic acid sequence. On the contrary, insignificant level of the signal (e.g., background signal) indicates the absence of the first target nucleic acid sequence or the second target nucleic acid sequence.

The signal (particularly, the signal intensity) may vary depending upon its detection temperature as well as a signal-generating means employed.

The incubation herein is performed by a signal-generating process using signal-generating means.

The term "signal-generating process" as used herein refers to any process capable of generating signals in a dependent manner on the presence of a target nucleic acid sequence in a sample.

The term "signal-generating means" as used herein refers to any material used in generation of signals indicating the presence of target nucleic acid sequences, for example including oligonucleotides, labels and enzymes. Alternatively, the term used herein "signal-generating means" can be used to refer to any methods using the materials for signal generation.

In particular, the terms "first signal-generating means" and "second signal-generating means" as used herein refer to means for generating signals for a first target nucleic acid sequence and a second target nucleic acid sequence, respectively. The first signal-generating means and the second signal-generating means may include common components (e.g., a single type of label and a single type of enzyme) or different components (e.g., different types of oligonucleotides) used in signal generation. In particular, the first signal-generating means and the second signal-generating means are characterized by having a single type of label (the same label). Thus, the signal derived from the label of the first signal-generating means is not differentiated from the signal derived from the label of the second signal-generating means by conventional methods.

A wide variety of the signal-generating means have been known to one of skill in the art. The signal-generating means include both labels per se and oligonucleotides with labels. The labels may include a fluorescent label, a luminescent label, a chemiluminescent label, an electrochemical label and a metal label. The label per se may serve as signal-generating means, for example, an intercalating dye. Alternatively, a single label or an interactive dual label containing a donor molecule and an acceptor molecule may be used as signal-generating means in the form of linkage to at least one oligonucleotide.

The signal-generating means may comprise additional components for generating signals such as nucleolytic enzymes (e.g., 5'-nucleases and 3'-nucleases).

The signal-generating process is accompanied with signal change. The signal change may serve as an indicator indicating qualitatively or quantitatively the presence or absence of a target nucleic acid sequence.

The details of "signal-generating process" are disclosed in WO 2015/147412 filed by the present inventors, the teachings of which are incorporated herein by reference in its entirety.

According to an embodiment, the signal-generating process is a signal amplification process.

According to an embodiment of this invention, the signal-generating process is a process with amplification or with no amplification of a target nucleic acid sequence.

Particularly, the signal-generating process is a process with amplification of a target nucleic acid molecule. More particularly, the signal-generating process is a process with amplification of a target nucleic acid molecule and capable of increasing or decreasing signals (particularly, increasing signals) upon amplifying the target nucleic acid molecule.

The term used herein "signal generation" include appearance or disappearance of signals and increase or decrease in signals. Particularly, the term "signal generation" means increase in signals.

The signal-generating process may be performed in accordance with a multitude of methods known to one of skill in the art. The methods include TaqMan™ probe method (U.S. Pat. No. 5,210,015), Molecular Beacon method (Tyagi et al., Nature Biotechnology, 14 (3):303(1996)), Scorpion method (Whitcombe et al., Nature Biotechnology 17:804-807 (1999)), Sunrise or Amplifluor method (Nazarenko et al., Nucleic Acids Research, 25(12):2516-2521(1997), and U.S. Pat. No. 6,117,635), Lux method (U.S. Pat. No. 7,537,886), CPT (Duck P, et al., Biotechniques, 9:142-148(1990)), LNA method (U.S. Pat. No. 6,977,295), Plexor method (Sherrill C B, et al., Journal of the American Chemical Society, 126: 4550-4556(2004)), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), Hybridization probe (Bernard P S, et al., Clin Chem 2000, 46, 147-148), PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (WO 2014/104818) and CER method (WO 2011/037306).

When the signal-generating process is performed in accordance with TaqMan™ probe method, the signal-generation means may comprise a primer pair, a probe with an interactive dual label and DNA polymerase having 5' to 3' nuclease activity. When the signal-generating process is performed in accordance with PTOCE method, the signal-generation means may comprise a primer pair, PTO (Probing and Tagging Oligonucleotide), CTO (Capturing and Templating Oligonucleotide) and DNA polymerase having 5' to 3' nuclease activity. Either PTO or CTO may be labeled with suitable labels.

According to an embodiment, the signal-generating process is performed in a process involving signal amplification together with target amplification.

According to an embodiment, the amplification reaction as the signal-generating process is performed in such a manner that signals are amplified simultaneously with amplification of the target nucleic acid sequence (e.g., real-time PCR). Alternatively, the amplification reaction is performed in such a manner that signals are amplified with no amplification of the target nucleic acid molecule [e.g., CPT method (Duck P, et al., Biotechniques, 9:142-148 (1990)), Invader assay (U.S. Pat. Nos. 6,358,691 and 6,194, 149)].

A multitude of methods have been known for amplification of a target nucleic acid molecule, including, but not limited to, PCR (polymerase chain reaction), LCR (ligase chain reaction, see Wiedmann M, et al., "Ligase chain reaction (LCR)—overview and applications." PCR Methods and Applications 1994 February; 3(4):551-64), GLCR (gap filling LCR, see WO 90/01069, EP 439182 and WO 93/00447), Q-beta (Q-beta replicase amplification, see Cahill P, et al., Clin Chem., 37(9):1482-5(1991), U.S. Pat. No. 5,556,751), SDA (strand displacement amplification, see G T Walker et al., Nucleic Acids Res. 20(7):16911696 (1992), EP 497272), NASBA (nucleic acid sequence-based amplification, see Compton, J. Nature 350(6313):912 (1991)), TMA (Transcription-Mediated Amplification, see Hofmann W P et al., J Clin Virol. 32(4):289-93(2005); U.S. Pat. No. 5,888,779) or RCA (Rolling Circle Amplification, see Hutchison C. A. et al., Proc. Natl Acad. Sci. USA. 102:1733217336(2005)).

After incubation of the sample, signals from the two signal-generating means (i.e., first signal generating means and second-signal generating means) are detected at a relatively high detection temperature and a relatively low detection temperature.

The present invention may be performed by using any type of signal-generating means in view of detection temperatures. One of the two signal-generating means may be designed to provide signals at both of the two detection temperatures in the presence of a corresponding target nucleic acid sequence, while the other designed to provide signals only at the relatively low detection temperature in the presence of a corresponding target nucleic acid sequence. Alternatively, the two signal-generating means all may be designed to provide signals at both of the two detection temperatures in the presence of a corresponding target nucleic acid sequence.

According to an embodiment, the detection temperatures are predetermined in considering a temperature range to allow for signal generation by the signal-generating means. The detection temperatures comprise the relatively high detection temperature (e.g., 72° C.) and the relatively low detection temperature (e.g., 60° C.).

According to an embodiment, the relatively high detection temperature is a temperature capable of generating a signal for the target nucleic acid sequence having the relatively high detection temperature, and the relatively low detection temperature is a temperature capable of generating both of a signal for the target nucleic acid sequence having the relatively low detection temperature and a signal for the target nucleic acid sequence having the relatively high detection temperature.

According to another embodiment, the relatively high detection temperature and the relatively low detection temperature are those capable of generating both of a signal for the target nucleic acid sequence having the relatively low detection temperature and a signal for the target nucleic acid sequence having the relatively high detection temperature.

One of features of the present invention is to determine differentially the presence of the two target nucleic acid sequences by detecting at different detection temperatures signals indicative of the presence of the two target nucleic acid sequences.

According to an embodiment, the detection temperatures for target nucleic acid sequences are predetermined in considering a temperature range to allow signal generation by the signal-generating means.

The present invention is based on the finding that there is a certain temperature range to allow signal generation in a dependent manner on signal-generating means.

For example, when a signal-generating means generates a signal upon hybridization (or association) between two nucleic acid molecules and do not generate a signal upon non-hybridization (or dissociation) between them, a signal is generated at temperatures allowing hybridization between two nucleic acid molecules, however, no signal is generated at temperatures failing to hybridize between two nucleic acid molecules. As such, there is a certain temperature range to allow signal generation i.e., signal detection) and other temperature range not to allow signal generation. The temperature ranges are affected by the Tm value of the hybrid of the two nucleic acid molecules employed in the signal-generation means.

Considering the two temperature ranges, a detection temperature may be determined for each of the target nucleic acid sequences. A relatively high detection temperature can be selected from the former temperature range, and the relatively high detection temperature is assigned to the first target nucleic acid sequence. A relatively low detection temperature can be selected from the latter temperature range, and the relatively low detection temperature is assigned to the second target nucleic acid.

The important technical feature of the present invention is to extract the signal for the second target nucleic acid sequence or the signal for the first target nucleic acid sequence, by analyzing both the signal at the relatively high detection temperature and the signal at the relatively low detection temperature.

The detection of signals is carried out in a detector, particularly a single type of detector.

The term "a single type of detector" as used herein means a detection means for a single type of signal. In a detector comprising several channels (e.g., photodiodes) for several different types of signals, each channel (e.g., a photodiode) corresponds to "a single type of detector".

According to an embodiment of this invention, the two signal-generating means comprise an identical label and signals from the label are not differentiated by the single type of detector.

The detection of signals from the two signal-generating means at a relatively high detection temperature and a relatively low detection temperature is performed at one or more cycles of the signal-generating process to obtain a signal value at each of the one or more cycles.

The term used herein "cycle" refers to a unit of changes of conditions in a plurality of measurements accompanied with changes of conditions. For example, the changes of conditions include changes in temperature, reaction time, reaction number, concentration, pH and/or replication number of a target nucleic acid molecule sequence. Therefore, the cycle may include time or process cycle, unit operation cycle and reproductive cycle. For example, an isothermal amplification allows for a plurality of measurements for a sample in the course of reaction time under isothermal conditions and the reaction time may correspond to the changes of conditions and a unit of the reaction time may correspond to a cycle.

Particularly, when repeating a series of reactions or repeating a reaction with a time interval, the term "cycle" refers to a unit of the repetition.

For example, in a polymerase chain reaction (PCR), a cycle refers to a reaction unit comprising denaturation of a target molecule, annealing (hybridization) between the target molecule and primers and primer extension. The increases in the repetition of reactions may correspond to the changes of conditions and a unit of the repetition may correspond to a cycle.

The number of cycles at which the detection is performed includes, but not limited to, 1-5, 1-10, 1-15, 1-20, 1-25, 1-30, 1-35, 1-40, 1-45, 1-50, 1-55 and 1-60. When the detection is performed at a plurality of cycles, the cycles may be consecutive cycles or non-consecutive cycles.

The detection of signals provides a signal value at each cycle of the signal-generating process. The term "signal value" as used herein means either a signal value actually measured at each cycle of the signal-generating process (e.g., actual value of fluorescence intensity processed by amplification reaction) or a modified value thereof. The modified value may include mathematically processed value of measured signal value (e.g., intensities). Examples of mathematically processed value of measured signal value may include logarithmic value and derivative of measured signal values. The term "signal" as used herein is intended to encompass the term "signal value" and therefore these terms will be used interchangeably.

The signals generated by the two signal-generating means are not differentiated by a single type of detector. The term "signals not differentiated by a single type of detector" means that signals are not differentiated from each other at a certain detection temperature by a single type of detector due to their identical or substantially identical signal properties (e.g., optical properties, emission wavelength and electrical signal).

The term used herein "a single type of signal" means signals providing identical or substantially identical signal properties (e.g., optical properties, emission wavelength and electrical signal). For example, FAM and CAL Fluor 610 provide different types of signals from one another.

The signals are generated by the signal-generating process, thereby providing a data set. The term used herein "data set" refers to a set of data points. The term used herein "data point" means a coordinate value comprising a cycle and a signal value at the cycle. Data points obtained by the signal-generating process may be plotted with coordinate values in a rectangular coordinate system, giving a curve (e.g., amplification curve). The curve may be a fitted or normalized (e.g., baseline-subtracted) curve. In particular, the signals detected are plotted against cycles.

In a particular embodiment, the signals, and the data sets, the data points and the curve thereof are baseline-subtracted.

Step (b): Processing Signal Values for Extraction of a Signal for a Target Nucleic Acid Sequence (S120; S220; S320; S420)

Afterwards, the signal values obtained in the step (a) are processed by using a second reference value to extract the signal for the first target nucleic acid sequence or processed by using a first reference value to extract the signal for the second target nucleic acid sequence.

The term "reference value" as used herein describes a relationship or degree of change in signals, a signal change or a signal difference, in particular numerically, when two signals are generated at different detection temperatures (i.e., relatively high detection temperature and relatively low detection temperature). Stated otherwise, the "reference value" includes any value reflecting a pattern (rule) of a signal change at different detection temperatures. Also, the term "reference value" indicates a value representing the degree of change between a signal detected at relatively high detection temperature and a signal detected at relatively low detection temperature for a particular target nucleic acid sequence. The reference value may indicate a value used herein to transform, convert, adjust or modify a signal detected at one temperature into a signal at another temperature. The reference value may vary depending upon the types of the target nucleic acid sequences, the types of the signal-generating means and the conditions of incubation and detection. Thus, a variety of reference values may be determined for different or same target nucleic acid sequences.

The reference value may be expressed in various aspects. For example, the reference value may be expressed as numerical values, the presence/absence of signal or plot with signal characteristics.

The term "reference value" is further described herein as "first reference value" or "second reference value". In the terms, the terms "first" and "second" are used for distinguishing reference values for the first target nucleic acid sequence and second target nucleic acid sequence, respectively.

Particularly, the terms "first reference value" and "second reference value" as used herein refer to reference values which are predetermined for the first target nucleic acid sequence and for the second target nucleic acid sequence, respectively and which are used in the signal extraction of the second target nucleic acid sequence and of the first target nucleic acid in step (b), respectively.

More particularly, the first reference value is a value representing a relationship of change in two signals provided by the first signal-generating means at the relatively high detection temperature and the relatively low detection temperature, and the second reference value is a value representing a relationship of change in two signals provided by the second signal-generating means at the relatively high detection temperature and the relatively low detection temperature.

In an embodiment, the reference value may be determined considering a signal value at a selected cycle. In other words, the reference value may be determined considering a signal value at a selected cycle among signals detected at a relatively high detection temperature and at a relatively low detection temperature. In such case, the selected cycle may be one of cycles following a baseline region of an amplification curve, particularly one of cycles in a plateau region, more particularly an end cycle.

In an alternative embodiment, the reference value may be determined considering a plurality of signal values at different selected cycles. For instance, the reference value may be determined considering a mean of a plurality of signal values at different selected cycles.

The reference values will be described in detail below.

The reference value may be predetermined by incubating a corresponding target nucleic acid sequence with a signal-generating means, detecting signals at a relatively high detection temperature and a relatively low detection temperature, and then obtaining a relationship of change in signals detected at the relatively high detection temperature and the relatively low detection temperature.

According to an embodiment, the reference value is predetermined by using a standard material corresponding to a target nucleic acid sequence.

According to an embodiment, the reference value is predetermined from a control reaction. For example, the first reference value is predetermined from a control reaction using the first target nucleic acid sequence and the first signal-generating means and the second reference value is predetermined from a control reaction using the second target nucleic acid sequence and the second signal-generating means.

According to an embodiment, the reference value may be predetermined by using a control sample containing a corresponding target nucleic acid sequence. For instance, the first reference value may be predetermined by using a control sample containing the first target nucleic acid sequence and the second reference value may be predetermined by using a control sample containing the second target nucleic acid sequence.

The reference value may be predetermined by acquiring a certain range of values via iterative reactions for the control reaction (or control sample) under various conditions (e.g., concentrations of a target nucleic acid sequence and types of primers) and selecting a suitable one among the acquired values.

In an embodiment, the reference value may be selected such that a signal for a target nucleic acid sequence not to be extracted is eliminated. In other embodiment, the reference value may be selected such that a signal for a target nucleic acid sequence to be extracted is not eliminated or eliminated as little as possible. In another embodiment, the reference value may be selected such that signal for a target nucleic acid sequence not to be extracted is eliminated and signal for a target nucleic acid sequence to be extracted is not eliminated or eliminated as little as possible.

For example, where one intends to extract a signal for a first target nucleic acid sequence by using a second reference value, the second reference value may be selected such that the signal for the second target nucleic acid sequence is eliminated and the signal for the first target nucleic acid sequence is not eliminated.

More specifically, when the target nucleic acid sequences comprise "*Chlamydia trachomatis* (CT)" and "*Neisseria gonorrhoeae* (NG)" and a signal for "NG" is intended to be extracted, the reference value for CT may be selected such that the signal for CT is completely eliminated and the signal for NG is not eliminated or eliminated as little as possible.

The reference value may be empirically obtained by repetitive experiments.

The reference value may be selected among a certain range empirically obtained by repetitive experiments. In this regard, it is advantageous that a relatively high value within the range is selected as a reference value, because the relatively high reference value has a higher propensity to eliminate a signal intended not to be extracted, compared to relatively low reference values. For example, when a range from 1.1 to 1.50 is obtained, a value around 1.50 may be more suitable as a reference value. Alternatively, a value exceeding the range may be selected as a reference value. For example, a value of 5%, 10%, 20%, 30%, 40%, 50%, 60%, 70%, 80%, 90% or 100% greater than the upper limit of the range may be selected a reference value. However, it is noted that too high reference value is not desirable, since it may rather eliminate a signal intended to be extracted.

According to an embodiment, the reference value can be calculated by the difference between signals provided by a corresponding signal-generating means at the relatively high detection temperature and the relatively low detection temperature.

According to an embodiment, the reference value can be calculated by mathematically processing the signals provided by a corresponding signal-generating means at the relatively high detection temperature and the relatively low detection temperature.

In certain embodiment, the mathematical processing includes calculation (e.g., addition, multiplication, subtraction and division) using signals or other values derived from signals.

According to an embodiment of this invention, the mathematical processing of the signals to obtain the reference value is a calculation of a ratio of the signal provided by a corresponding signal-generating means at the relatively low detection temperature to the signal provided by a corresponding signal-generating means at the relatively high detection temperature. According to an embodiment of this invention, the mathematical processing of the signals to obtain the reference value is a calculation of a ratio of the signal provided by a corresponding signal-generating means at the relatively high detection temperature to the signal provided by a corresponding signal-generating means at the relatively low detection temperature.

The ratio may be a ratio of a signal value at a cycle of signals detected at the relatively low detection temperature to a signal value at the cycle of signals detected at the relatively high detection temperature. Alternatively, the ratio may be a ratio of a signal value at a select cycle of signals detected at the relatively high detection temperature to a signal value at the select cycle of signals detected at the relatively low detection temperature. The cycle selected for ratio calculation may be one of cycles following a baseline region of an amplification curve. Particularly, the cycle for ratio calculation may be one of cycles in a plateau region. More particularly, the cycle for ratio calculation may be the end cycle.

In an embodiment, the reference value can be obtained by a mean of ratios at several cycles, e.g., consecutive two cycles, three cycles, four cycles, five cycles, etc. Further, the reference value can be suitably selected in consideration of ratios at several cycles. For example, the reference value can be selected as being a slightly higher than a ratio of a signal value at a select cycle or ratios of signal values at several cycles.

In a particular embodiment, the reference value may be calculated in accordance with the mathematical Equation II:

Reference value for a target=[signal at the relatively low temperature for a sample containing only the target]÷[signal at the relatively high temperature for a sample containing only the target] <Equation II>

The mathematical processing for obtaining the reference value may be carried out in various fashions. The mathematical processing may be carried out by use of a machine. For example, the signals may undergo a mathematical processing by a processor in a detector or real-time PCR device. Alternatively, the signals may manually undergo a mathematical processing particularly according to a predetermined algorithm.

According to an embodiment of this invention, signal-generating means for the reference value may be the same as that for the step (a).

According to an embodiment, the processing of the signal values in the step (b) is carried out by eliminating the signal for the second target nucleic acid sequence from the signals obtained in the step (a) by the second reference value or eliminating the signal for the first target nucleic acid sequence from the signals obtained in the step (a) by the first reference value.

More particularly, the elimination of the signal generated by the second signal generating means is to mathematically eliminate the signal for the second target nucleic acid sequence from the signals obtained in the step (a) and the elimination of the signal generated by the first signal generating means is to mathematically eliminate the signal for the first target nucleic acid sequence from the signals obtained in the step (a).

Still more particularly, the elimination of the signal generated by the second (or first) signal generating means is to mathematically eliminate the signal for the second (or first) target nucleic acid sequence from the signal detected at a relatively low temperature, or to mathematically eliminate the signal for the second (or first) target nucleic acid sequence from the signal detected at a relatively high temperature.

The present inventors developed two technologies for detecting multiple target nucleic acid sequences in a sample using different detection temperatures. In the former technology, the first signal-generating means generates signals both at the relatively high detection temperature and the relatively low detection temperature and the second signal-generating means generates a signal at the relatively low detection temperature (see WO 2015/147412). In the latter technology, both the first signal-generating means and the second signal-generating means generate signals both at the relatively high detection temperature and the relatively low detection temperature (see WO 2016/093619). The former and latter technologies are called as MuDT1 and MuDT2 technologies, respectively.

Where the present invention is applied to the MuDT1 technology (see WO 2015/147412), it may be performed as follows:

According to an embodiment, the first signal-generating means generates signals at the relatively high detection temperature and the relatively low detection temperature and the second signal-generating means generates a signal at the relatively low detection temperature, and the processing of the signal values in the step (b) comprises mathematically processing the signal values by using the first reference value to extract the signal for the second target nucleic acid sequence from the signal at the relatively low detection temperature obtained in the step (a).

More particularly, the extraction of the signal for the second target nucleic acid sequence may be performed by the following mathematical Equation I-1:

Extracted signal for the second target nucleic acid sequence=[signal at the relatively low detection temperature obtained in the step (a)]−[(signal at the relatively high detection temperature obtained in the step (a))×(first reference value)]; <Equation I-1> wherein the first reference value is a ratio of the signal provided by the first signal-generating means at the relatively low detection temperature to the signal provided by the first signal-generating means at the relatively high detection temperature.

In the mathematical Equations described herein, the symbol "−" represents minus, particularly signal subtraction. For example, the signal subtraction may be performed at each cycle by subtracting a signal value at a cycle in one signal from a signal value at a corresponding cycle in another signal.

In the mathematical Equations described herein, the symbol "×" represents multiplication.

In the mathematical Equations described herein, the symbol "÷" represents division.

According to the extraction of the signal for the second target nucleic acid sequence by the mathematical Equation I-1, the signal detected at the relatively low detection temperature reflects a combination of the signal for the first target nucleic acid sequence and the signal for the second target nucleic acid sequence, whereas the signal detected at the relatively high detection temperature only reflects the signal for the first target nucleic acid sequence. Thus, the signal for the second target nucleic acid sequence may be obtained by subtracting the signal detected at the relatively high detection temperature from the signal detected at the relatively low detection temperature, with a proviso that the signals for the first target nucleic acid sequence at the relatively high detection temperature and the relatively low detection temperature are not changed. However, considering that the signals vary depending upon the detection temperatures, it is necessary to adjust (transform) the signal detected at the relatively high detection temperature into a signal to be expected at the relatively low detection temperature, prior to the signal subtraction. For this purpose, the first reference value is used.

According to an alternative embodiment, the first signal-generating means generates signals at the relatively high detection temperature and the relatively low detection temperature and the second signal-generating means generates a signal at the relatively low detection temperature, and the processing of the signal values in the step (b) comprises mathematically processing the signal values by using the first reference value to extract the signal for the second target nucleic acid sequence from the signal at the relatively high detection temperature obtained in the step (a).

More particularly, the extraction of the signal for the second target nucleic acid sequence is performed by the following mathematical Equation I-2:

Extracted signal for the second target nucleic acid sequence=[signal at the relatively high detection temperature obtained in the step (a)]−[(signal at the relatively low detection temperature obtained in the step (a))÷(first reference value)]; <Equation I-2> wherein the first reference value is a ratio of the signal provided by the first signal-generating means at the relatively low detection temperature to the signal provided by the first signal-generating means at the relatively high detection temperature.

In the MuDT1 technology, the signal detected at the relatively high detection temperature may be considered as the extracted signal for the first target nucleic acid sequence because the signal for the first target nucleic acid sequence is only detected at the relatively high detection temperature.

In the mathematical Equations I-1 and I-2, the first reference value is represented by the ratio of the signal at the relatively low detection temperature to the signal at the relatively high detection temperature. It would be understood by one of skill in the art that the signal extraction for the second target nucleic acid sequence may be accomplished with a modification using a first reference value represented by the ratio of the signal at the relatively high detection temperature to the signal at the relatively low detection temperature. Those of skill in the art would understand that such modification falls within the spirit and scope of the invention.

Where the present invention is applied to the MuDT2 technology (see WO 2016/093619), it may be performed as follows:

According to an embodiment, the two signal-generating means generate signals at the relatively high detection temperature and the relatively low detection temperature.

According to an embodiment, when the second reference value is greater than the first reference value, (i) the processing of the signal values in the step (b) comprises mathematically extracting the signal for the second target nucleic acid sequence by the first reference value from the signal at the relatively low detection temperature; (ii) the processing of the signal values in the step (b) comprises mathematically extracting the signal for the second target nucleic acid sequence by the first reference value from the signal at the relatively high detection temperature in the step (a); (iii) the processing of the signal values in the step (b) comprises mathematically extracting the signal for the first target nucleic acid sequence by the second reference value from the signal at the relatively low detection temperature; or (iv) the processing of the signal values in the step (b) comprises mathematically extracting the signal for the first target nucleic acid sequence by the second reference value from the signal the signal at the relatively high detection temperature in the step (a).

More particularly, the extraction of the signal for the second target nucleic acid sequence by the first reference value from signals at the relatively low detection temperature is performed by the mathematical Equation I-1; the extraction of the signal for the second target nucleic acid sequence by the first reference value from signals at the relatively high detection temperature is performed by the following mathematical Equation I-2; the extraction of the signal for the first target nucleic acid sequence by the second reference value from signals at the relatively low detection temperature is performed by the following mathematical Equation I-3; or the extraction of the signal for the first target nucleic acid sequence by the second reference value from signals at the relatively high detection temperature is performed by the following mathematical Equation I-4:

Extracted signal for the second target nucleic acid sequence=[signal at the relatively low detection temperature obtained in the step (a)]−[(signal at the relatively high detection temperature obtained in the step (a))×(first reference value)];   <Equation I-1>

Extracted signal for the second target nucleic acid sequence=[signal at the relatively high detection temperature obtained in the step (a)]−[(signal at the relatively low detection temperature obtained in the step (a))÷(first reference value)];   <Equation I-2> wherein the first reference value is a ratio of the signal provided by the first signal-generating means at the relatively low detection temperature to the signal provided by the first signal-generating means at the relatively high detection temperature;

Extracted signal for the first target nucleic acid sequence=[signal at the relatively low detection temperature obtained in the step (a)]−[(signal at the relatively high detection temperature obtained in the step (a))×(second reference value)];   <Equation I-3>

Extracted signal for the first target nucleic acid sequence=[signal at the relatively high detection temperature obtained in the step (a)]−[(signal at the relatively low detection temperature obtained in the step (a))÷(second reference value)];   <Equation I-4> wherein the second reference value is a ratio of the signal provided by the second signal-generating means at the relatively low detection temperature to the signal provided by the second signal-generating means at the relatively high detection temperature.

When referring to the mathematical Equation I-3, each of the signals detected at the relatively low detection temperature and at the relatively high detection temperature reflects a combination of the signal for the first target nucleic acid sequence and the signal for the second target nucleic acid sequence. Assuming that the second reference value is greater than the first reference value, the multiplication of the signal at the relatively high detection temperature by the second reference value allows the signal for the second target nucleic acid sequence (contained in the signal detected at the relatively high detection temperature) to be transformed into the signal expected to be detected at the relatively low detection temperature. In addition, the multiplication also transforms the signal for the first target nucleic acid sequence (contained in the signal detected at the relatively high detection temperature) into the signal greater than that expected to be detected at the relatively low detection temperature. Thus, the signal subtraction of the transformed signals from the signal detected at the relatively low detection temperature will allow for the signal extraction of the first target nucleic acid sequence, since such subtraction will eliminate the signal for the second target nucleic acid sequence.

In the Equations I-1, I-2, I-3 and I-4, the reference values are represented by the ratio of the signal at the relatively low detection temperature to the signal at the relatively high detection temperature. It would be understood by one of skill in the art that the signal extraction may be accomplished with a modification using reference values represented by the ratio of the signal at the relatively high detection temperature to the signal at the relatively low detection temperature. Those of skill in the art would understand that such modification falls within the spirit and scope of the invention.

It is noted that the mathematical Equations I-1 and I-2 are commonly used in both the MuDT1 technology and the MuDT2 technology; whereas the mathematical Equations I-3 and I-4 are used only in the MuDT2 technology. Therefore, prior to application of the mathematical Equations according the method of the present invention, it is essential to ascertain which of the two technologies was carried out.

The use of the extracted signal in determining the presence of a target nucleic acid sequence may result in false positive or false negative results when using an unsuitable reference value. To overcome this problem, the method of the present invention provides only a specific region as an analytical signal for use in determining the presence of a target nucleic acid sequence.

Step (c): Selection of Cycle Having Maximum or Minimum Signal Value (S130; S230; S330; S430)

In the step (c), a cycle having a maximum signal value or a minimum signal value is selected from the extracted signal for the first target nucleic acid sequence or the second target nucleic acid sequence.

Interestingly, the present inventors have found that a cycle having a maximum signal value (also referred to herein as "maximum cycle") or a minimum signal value (also referred to herein as "minimum cycle") is an important indicator in analyzing the extracted signal, particularly, in analyzing an erroneously extracted signal.

Based on our findings, a cycle having a maximum signal value or a minimum signal value serves as a reference point for distinguishing between a target-related signal region and a target-unrelated signal region.

The term "target-related signal region" as used herein refers to a region of an extracted signal, which is considered to be significant in determining the presence or absence of a target nucleic acid sequence of interest, since the region contains an accurate signal associated with the target nucleic acid sequence. Thus, "the signal in the target-related signal region" is used as an analytical signal for determining the presence/absence of a target nucleic acid sequence.

The term "target-unrelated signal region" as used herein refers to a region of an extracted signal, which is considered to be negligible in determining the presence or absence of a target nucleic acid sequence of interest, since the region may contain an inaccurate signal unassociated with the target nucleic acid sequence. Thus, "the signal in the target-unrelated signal region" is not used as an analytical signal for determining the presence/absence of a target nucleic acid sequence.

For a more comprehensive understanding of the role of the cycle having the maximum signal value or the minimum signal value in analyzing the extracted signal, an exemplary embodiment of the present invention is discussed, including a signal-generating process in which the signal intensity increases with amplification of a target nucleic acid sequence, and a extraction process performed in accordance with MuDT1 technology using mathematical Equation I-1.

In the exemplary embodiment, when a suitable reference value of the first target nucleic acid sequence is used, the extracted signal for the second target nucleic acid sequence may show (i) increasing pattern or (ii) substantially zero (0); however if an unsuitable reference value of the first target nucleic acid sequence is applied, all or a part of the resulting extracted signal may show a decreasing pattern.

Considering the above patterns, a cycle having a minimum signal value may play an important role in interpreting the extracted signal, particularly an erroneously extracted signal.

Typically, a cycle having a minimum signal value may be an inflection point at which the signal changes from a decreasing pattern (i.e., downward pattern) to an increasing pattern (i.e., upward pattern).

Based on the inference above, the region before the cycle having the minimum signal value showing a decreased pattern may be considered as being reflective of poor extraction; and the region after the cycle having the minimum signal value showing an increased pattern may be considered as being reflective of proper extraction.

In particular, the decreasing pattern appearing before the cycle having the minimum signal value may indicate that the signal for the second target nucleic acid sequence has not been suitably extracted to the level at which it actually contributes to the signal at the relatively low detection temperature (the expected level for proper extraction).

Also, the signal value at the cycle having the minimum signal value may indicate that the signal for the target nucleic acid sequence has been extracted to the lowest level. On the other hand, an increasing pattern appearing after the cycle having the minimum signal value may indicate that the signal for the target nucleic acid sequence is properly extracted (when the signal value is above RFU 0) or that the poorly extracted signal is being improved or recovered (when the signal value is below RFU 0).

Accordingly, when a cycle having a minimum signal value is selected, the region showing an increasing pattern is considered to be significant in determining the presence or absence of a target nucleic acid sequence of interest, which corresponds to a target-related signal region.

This inference can be applied to the role of the cycle having the maximum signal value in analyzing the extracted signal by, for example, MuDT1 technology using mathematical Equation I-2. In an exemplary embodiment in which when a suitable reference value for the first target nucleic acid sequence is used, the extracted signal for the second target nucleic acid sequence may show (i) decreasing pattern or (ii) substantially zero (0), however if an unsuitable reference value for the first target nucleic acid sequence is used, all or a part of the resulting extracted signal may show an increasing pattern.

Accordingly, when a cycle having a maximum signal value is selected, the region showing a decreasing pattern is considered to be significant in determining the presence or absence of a target nucleic acid sequence of interest, which corresponds to a target-related signal region.

In all embodiments of this invention, the target-related signal region can be used to determine the presence of the target nucleic acid sequence, even if it contains a signal pattern that is not theoretically predicted. The target-related signal region may be regarded as being correspond to an exponential phase in an amplification curve.

It will be appreciated that the target-related signal region may consist of a single cycle or a plurality of cycles. For instance, if the cycle having the maximum signal value or the minimum signal value is an end cycle, the target-related signal region consists of only one cycle; if the cycle having the maximum signal value or the minimum signal value is any cycle other than an end cycle, the target-related signal region consists of a plurality of cycles.

As used herein, the cycle having the maximum signal value or the minimum signal value may be referred to as a "selected cycle" or "select cycle".

The selected cycle as described above may be a cycle having a maximum signal value (having the highest signal value) or a cycle having the minimum signal value (having the lowest signal value), which depends upon the signal-generating process and the extraction process used in the step (b).

According to an embodiment of the present invention, when the suitably extracted signal for a target nucleic acid sequence of interest exhibits an increasing signal pattern in the presence of the target nucleic acid sequence in a sample, the selected cycle as described above may be a cycle having the minimum signal value (having the lowest signal value).

According to another embodiment of the present invention, when the suitably extracted signal for a target nucleic acid sequence of interest exhibits a decreasing signal pattern in the presence of the target nucleic acid sequence in a sample, the selected cycle as described above may be a cycle having a maximum signal value (having the highest signal value).

Where the present invention is applied to the MuDT1 technology (see WO 2015/147412), the selected cycle may be as follows:

(i) When a signal-generating process in which the signal intensity increases with amplification of a target nucleic acid sequence is performed and the extraction of the signal for the second target nucleic acid sequence is performed by the mathematical Equation I-1, the selected cycle may be a cycle having the minimum signal value; and (ii) When a signal-generating process in which the signal intensity increases with amplification of a target nucleic acid sequence is performed and the extraction of the signal for the second target nucleic acid sequence is performed by the mathematical Equation I-2, the selected cycle may be a cycle having a maximum signal value.

Alternatively, where the present invention is applied to the MuDT2 technology (see WO 2016/093619) and the second reference value is greater than the first reference value, the selected cycle may be as follows:

(i) When a signal-generating process in which the signal intensity increases with amplification of a target nucleic acid sequence is performed and the extraction of the signal for the second target nucleic acid sequence is performed by the mathematical Equation I-1, the selected cycle may be a cycle having the minimum signal value;

(ii) When a signal-generating process in which the signal intensity increases with amplification of a target nucleic acid sequence is performed and the extraction of the signal for the second target nucleic acid sequence is performed by the mathematical Equation I-2, the selected cycle may be a cycle having a maximum signal value;

(iii) When a signal-generating process in which the signal intensity increases with amplification of a target nucleic acid sequence is performed and the extraction of the signal for the first target nucleic acid sequence is performed by the mathematical Equation I-3, the selected cycle may be a cycle having a maximum signal value;

(iv) When a signal-generating process in which the signal intensity increases with amplification of a target nucleic acid sequence is performed and the extraction of the signal for the first target nucleic acid sequence is performed by the mathematical Equation I-4, the selected cycle may be a cycle having the minimum signal value;

(v) When a signal-generating process in which the signal intensity decreases with amplification of a target nucleic acid sequence is performed and the extraction of the signal for the second target nucleic acid sequence is performed by the mathematical Equation I-1, the selected cycle may be a cycle having a maximum signal value;

(vi) When a signal-generating process in which the signal intensity decreases with amplification of a target nucleic acid sequence is performed and the extraction of the signal for the second target nucleic acid sequence is performed by the mathematical Equation I-2, the selected cycle may be a cycle having the minimum signal value;

(vii) When a signal-generating process in which the signal intensity decreases with amplification of a target nucleic acid sequence is performed and the extraction of the signal for the first target nucleic acid sequence is performed by the mathematical Equation I-3, the selected cycle may be a cycle having the minimum signal value; and (viii) When a signal-generating process in which the signal intensity decreases with amplification of a target nucleic acid sequence is performed and the extraction of the signal for the first target nucleic acid sequence is performed by the mathematical Equation I-4, the selected cycle may be a cycle having a maximum signal value.

The determination of the selected cycle may be exemplified by referring to FIGS. 6A and 6B, and FIGS. 7A and 7B.

Figure 6A:
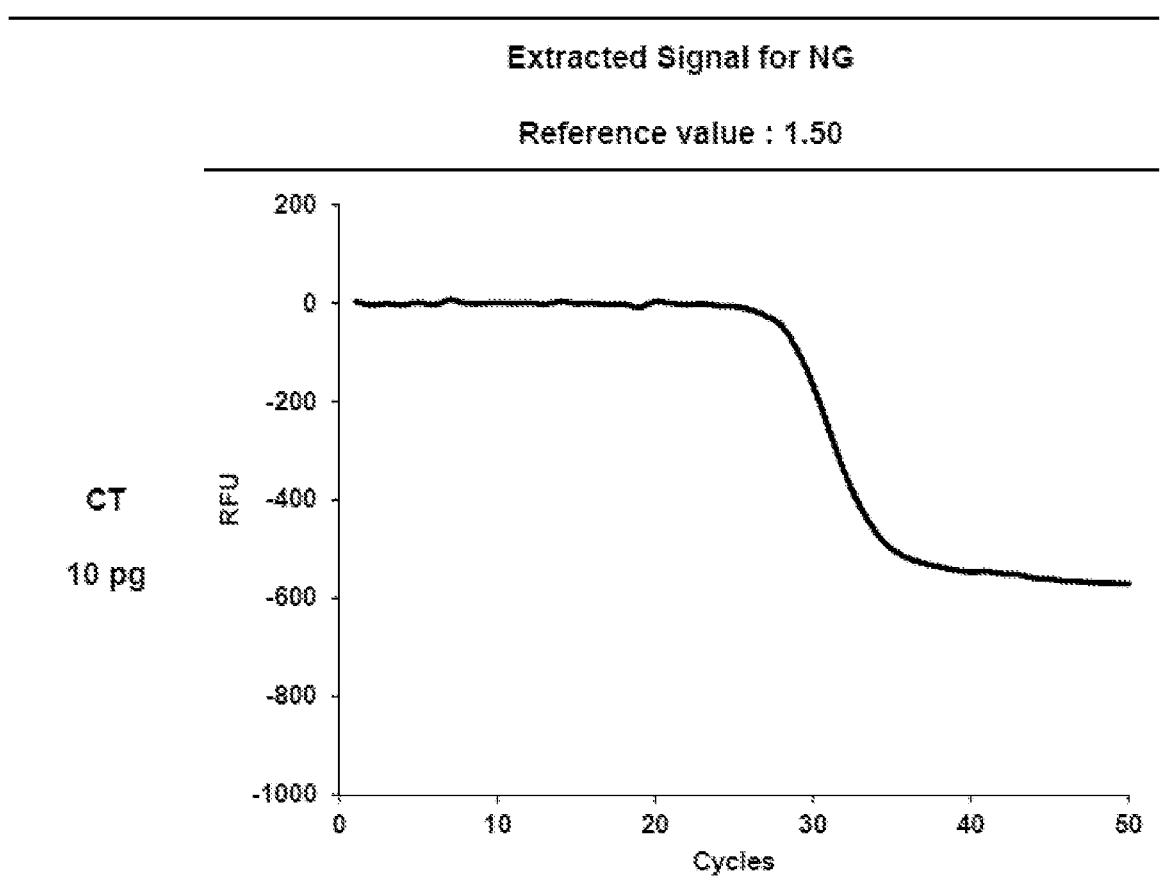
FIG. 6A represents an example of a signal extraction for NG target by using Equation I-1 in the sample containing 10 pg of CT target.

As shown in FIG. 6A, an extracted signal for NG target is obtained by using a single reference value of 1.50 from a sample containing 10 pg of CT target. Then, the extracted signal for NG is analyzed and a cycle having the minimum signal value (indicated as "Minimum cycle"; corresponding to $50^{th}$ cycle) is then selected (see FIG. 6B; top left).

Figure 7A:
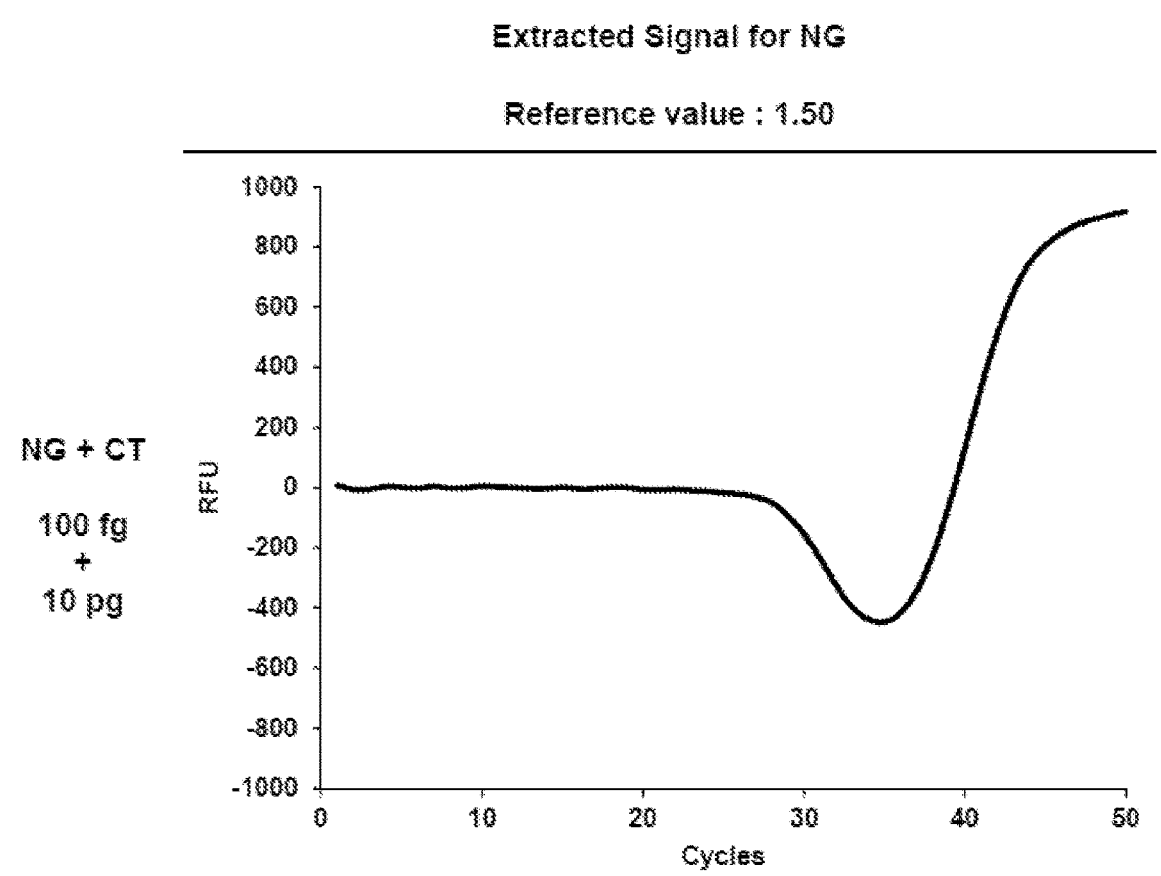
FIG. 7A represents an example of a signal extraction for NG target by using Equation I-1 in the sample containing 100 fg of NG and 10 pg of CT target.

As shown in FIG. 7A, an extracted signal for NG target is obtained by using a single reference value of 1.50 from a sample containing 100 fg of NG target and 10 pg of CT target. Then, the extracted signal for NG is analyzed and a cycle having the minimum signal value (indicated as "Minimum cycle"; corresponding to $35^{th}$ cycle) is then selected (see FIG. 7B; top left).

In an embodiment of the present invention, the selection of a cycle having a maximum signal value or a minimum signal value may be performed only when the extracted signal in the step (b) is erroneous.

Hereinafter, the embodiment will be described in detail in Section "Use of Criterion" below:

"Use of Criterion"

According to the embodiment, when the signal for the target nucleic acid sequence is correctly extracted in the step (b), the cycle having the maximum signal value or the minimum signal value may not be selected; when the signal for the target nucleic acid sequence is erroneously extracted in the step (b), the cycle having the maximum signal value or the minimum signal value may be selected.

Figure 3:
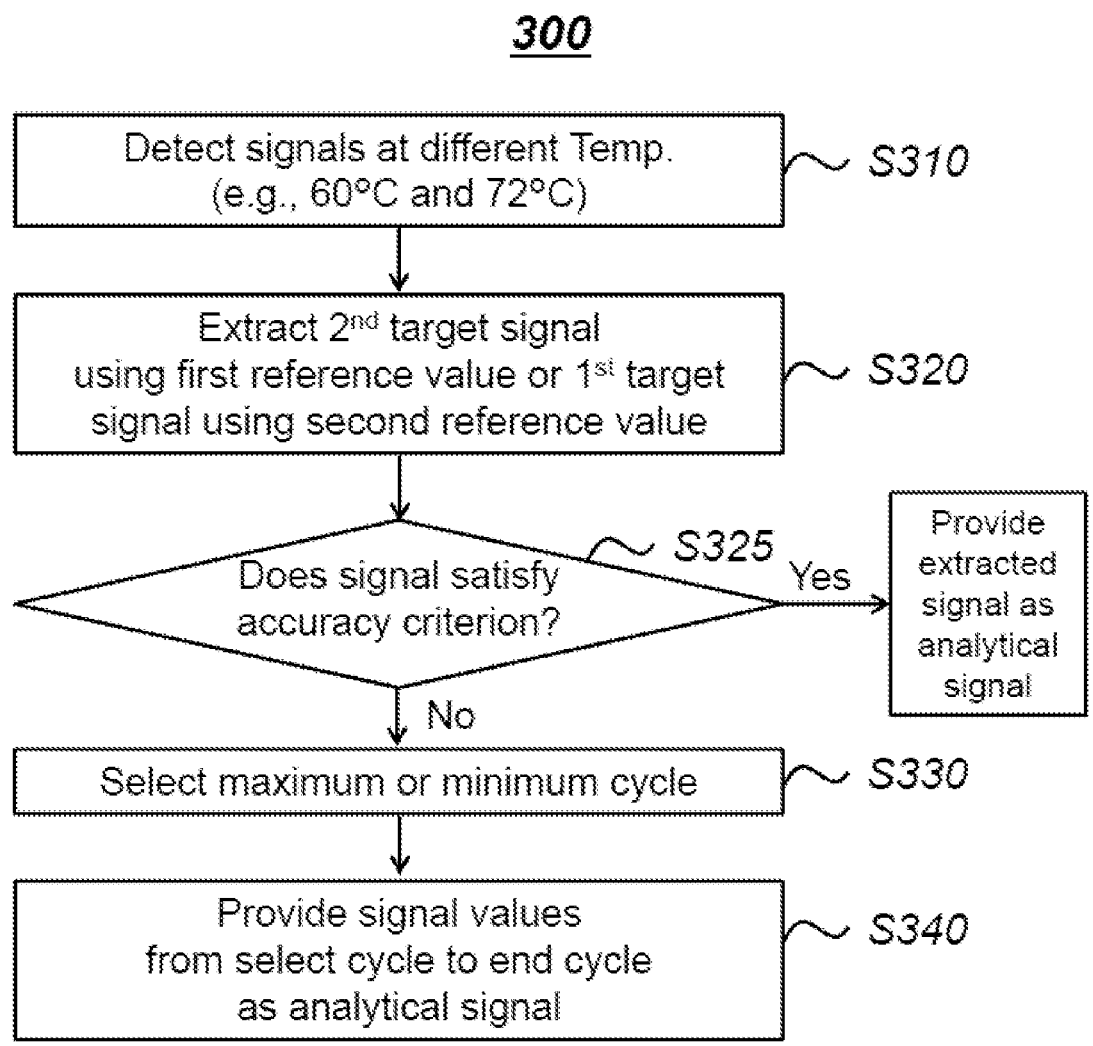

The embodiment is illustrated in FIG. 3 (300).

The embodiment further comprises the following steps between the step (b) and the step (c):

(bc-1) identifying whether the extracted signal satisfies an accuracy criterion; wherein the accuracy criterion is that the extracted signal does not cross a threshold; and (bc-2) proceeding to the step (c) when the extracted signal for the first target nucleic acid sequence or the second target nucleic acid sequence does not satisfy the accuracy criterion; or providing the extracted signal as an analytical signal without proceeding to the step (c) when the extracted signal for the first target nucleic acid sequence or the second target nucleic acid sequence satisfies the accuracy criterion.

The step (bc-1) and (bc-2) will be explained in detail below.

Step (bc-1): Identification of Erroneously Extracted Signal (S325)

In the step of (bc-1), it is identified whether the extracted signal satisfies an accuracy criterion; wherein the accuracy criterion is that the extracted signal does not cross a threshold.

Specifically, the signal extracted in the step (b) is analyzed to identify whether it is correctly or suitably extracted.

The term "correctly extracted signal" refers to an extracted signal showing a theoretically-predicted signal pattern, particularly in MuDT1 or MuDT2 technologies; the term "erroneously extracted signal" refers to an extracted signal showing a theoretically-unpredicted signal pattern, particularly in MuDT1 or MuDT2 technologies.

For a conventional signal-generating process in which the signal intensity increases or decreases with amplification of a target nucleic acid sequence when a target nucleic acid sequence is present in a sample, the extracted signal for the target nucleic acid sequence would be likely to produce either an increasing or decreasing pattern; whereas when a target nucleic acid sequence is absent in a sample, the extracted signal for the target nucleic acid sequence would be likely to produce a substantially zero (0) value (e.g., RFU 0)-approaching pattern.

Therefore, according to an embodiment of the present invention, when the suitably extracted signal for a target nucleic acid sequence of interest exhibits an increasing signal pattern in the presence of the target nucleic acid sequence in a sample and exhibits a substantially zero (0) value (e.g., RFU 0)-approaching pattern in the absence of the target nucleic acid sequence in a sample, such two patterns are regarded as theoretically-predicted patterns, but other patterns deviating from such signal patterns are regarded as theoretically unpredicted patterns. For example, a signal pattern having a signal value less than zero may be considered as a theoretically-unpredicted pattern.

According to another embodiment of the present invention, when the suitably extracted signal for a target nucleic acid sequence of interest exhibits a decreasing signal pattern in the presence of the target nucleic acid sequence in a sample and exhibits a substantially zero (0) value (e.g., RFU 0)-approaching pattern in the absence of the target nucleic acid sequence in a sample, such two patterns are regarded as theoretically-predicted patterns, but other patterns deviating from such signal patterns are regarded as theoretically unpredicted patterns. For example, a signal pattern having a signal value more than zero may be considered as a theoretically-unpredicted pattern.

It should be noted that the correctly extracted signal and the erroneously extracted signal herein should be comprehensively interpreted, i.e., by taking into account the extracted signal as a whole. For example, a signal having at least one portion showing a theoretically-unpredicted pattern should be regarded as an erroneously extracted signal.

Whether the signal is correctly or suitably extracted is identified using an accuracy criterion.

The term used herein "accuracy criterion" with reference to signal extraction means a criterion allowing for differentially discriminating correctly (accurately) extracted signals from erroneously extracted signals. For example, the accuracy criterion may mean a criterion allowing for identifying whether the extracted signal shows a theoretically-predicted signal pattern. The accuracy criterion may mean a criterion for determining suitability (accuracy) of the reference value for signal extraction.

The accuracy criterion may be suitably predetermined by one of skill in the art, as long as it can distinguish correctly extracted signals from erroneously extracted signals. The accuracy criterion may be, without limitation, any value. The accuracy criterion may be empirically predetermined.

In an embodiment, the accuracy criterion may be predetermined in consideration of the pattern of signals to be theoretically predicted in signal extraction.

As indicated above, the accuracy of signal extraction is based on whether the extracted signal satisfies the accuracy criterion.

In other words, the identification that the extracted signal satisfies the accuracy criterion demonstrates suitability of the reference value for signal extraction, whereas the identification that the extracted signal does not satisfy the accuracy criterion demonstrates unsuitability of the reference value for signal extraction.

Given that the reference value used in the step (b) is suitable, the extracted signal is very likely to show a theoretically-predicted signal pattern. For example, assumed that the reference value is suitable and normal signals show positive values (e.g., increasing or growing pattern) or substantially zero (0) value (e.g., RFU 0)-approaching pattern (e.g., background pattern), it can be determined that signals showing negative values (e.g. decreasing pattern) are erroneous. Where an accuracy criterion for elevating accuracy of such determination is applied by adopting a threshold as any value of less than zero (0) and the extracted signal has a signal value crossing the threshold, the extracted signal can be determined to be erroneous. In contrast, where signals showing positive values (e.g. increasing or growing pattern) are theoretically erroneous and a threshold is adopted as any value of more than zero (0), the extracted signal having a signal value crossing the threshold can be determined to be erroneous.

The accuracy criterion may be exemplified by a threshold.

In an embodiment of the present invention, the accuracy criterion is that the extracted signal does not cross a threshold, i.e., that the extracted signal has no signal value crossing a threshold (or a threshold line).

Where the extracted signal for the first target nucleic acid sequence or the second target nucleic acid sequence satisfies the accuracy criterion, the extracted signal is provided as an analytical signal for determination of the presence/absence of the respective target nucleic acid sequence without proceeding to the step (c).

For example, where the extracted signal has no signal value crossing a threshold, the procedures of the present method are terminated. In such case, the signal extracted by using the reference value is regarded as an accurately extracted signal and provided as an analytical signal.

The accuracy criterion represented by the extracted signal having no signal value crossing a threshold encompasses two cases: the extracted signal having signal values of more than a threshold and the extracted signal having signal values of less than a threshold.

The term "the extracted signal having signal value of more than a threshold" means that the signal values at all cycles in the extracted signal exceed a threshold. Likewise, the term "the extracted signal having signal values of less than a threshold" means that the signal values at all cycles in the extracted signal fall below a threshold.

For example, where the accuracy criterion is that the extracted signal has signal values of more than the predetermined threshold and the extracted signal is determined to have signal values of more than the predetermined threshold, the extracted signal (from 1st cycle to an end cycle) is provided as an analytical signal for determination of the presence/absence of the target nucleic acid sequence without performing the next steps. Where the accuracy criterion is that the extracted signal has signal values of less than the predetermined threshold and the extracted signal is determined to have signal values less than the predetermined threshold, the extracted signal (from 1st cycle to an end cycle) is provided as an analytical signal for determination of the presence/absence of the target nucleic acid sequence without performing the next steps.

The threshold may be predetermined based on the theoretically predicted signal pattern, upon extraction of signal according to the present invention.

As one example, where a theoretically predicted normal signal pattern is positive values (e.g., increasing or growing pattern) or substantially zero (0) value (e.g., RFU 0)-approaching pattern (e.g., a background pattern), the threshold may be any suitable negative value and the accuracy criterion may be that the extracted signal has signal values of more than the threshold. For example, the threshold may be, e.g., RFU −10, −20, −30, −40, −50, −60, −70, −80, −90, −100, −200, −300 or less. In this case, the extracted signal having signal values of not more than the threshold, i.e., the extracted signal having a signal value crossing the threshold, can be regarded as an abnormally extracted signal.

As another example, where a theoretically predicted normal signal pattern is negative values (e.g., decreasing pattern) or substantially zero (0) value (e.g., RFU 0)-approaching pattern (e.g., a background pattern), the threshold may be any suitable positive value and the accuracy criterion may be that the extracted signal has signal values of less than the threshold. For example, the threshold may be, e.g., RFU 10, 20, 30, 40, 50, 60, 70, 80, 90, 100, 200, 300 or more, but not limited thereto. In this case, the extracted signal having signal values of not less than the threshold, i.e., the extracted signal having a signal value crossing the threshold, can be regarded as an abnormally extracted signal.

The threshold may vary depending upon the signal-generating process and the extraction process used in the step (b).

Specifically, where the present invention is applied to the MuDT1 technology (see WO 2015/147412), the threshold may be determined as follows:

(i) When a signal-generating process in which the signal intensity increases with amplification of a target nucleic acid sequence is performed and the extraction of the signal for the second target nucleic acid sequence is performed by the mathematical Equation I-1, the threshold may be a negative value; and (ii) When a signal-generating process in which the signal intensity increases with amplification of a target nucleic acid sequence is performed and the extraction of the signal for the second target nucleic acid sequence is performed by the mathematical Equation I-2, the threshold may be a positive value.

Alternatively, where the present invention is applied to the MuDT2 technology (see WO 2016/093619) and the second reference value is greater than the first reference value, the threshold may be predetermined as follows:

(i) When a signal-generating process in which the signal intensity increases with amplification of a target nucleic acid sequence is performed and the extraction of the signal for the second target nucleic acid sequence is performed by the mathematical Equation I-1, the threshold may be a negative value;

(ii) When a signal-generating process in which the signal intensity increases with amplification of a target nucleic acid sequence is performed and the extraction of the signal for the second target nucleic acid sequence is performed by the mathematical Equation I-2, the threshold may be a positive value;

(iii) When a signal-generating process in which the signal intensity increases with amplification of a target nucleic acid sequence is performed and the extraction of the signal for the first target nucleic acid sequence is performed by the mathematical Equation I-3, the threshold may be a positive value;

(iv) When a signal-generating process in which the signal intensity increases with amplification of a target nucleic acid sequence is performed and the extraction of the signal for the first target nucleic acid sequence is performed by the mathematical Equation I-4, the threshold may be a negative value;

(v) When a signal-generating process in which the signal intensity decreases with amplification of a target nucleic acid sequence is performed and the extraction of the signal for the second target nucleic acid sequence is performed by the mathematical Equation I-1, the threshold may be a positive value;

(vi) When a signal-generating process in which the signal intensity decreases with amplification of a target nucleic acid sequence is performed and the extraction of the signal for the second target nucleic acid sequence is performed by the mathematical Equation I-2, the threshold may be a negative value;

(vii) When a signal-generating process in which the signal intensity decreases with amplification of a target nucleic acid sequence is performed and the extraction of the signal for the first target nucleic acid sequence is performed by the mathematical Equation I-3, the threshold may be a negative value; and (viii) When a signal-generating process in which the signal intensity decreases with amplification of a target nucleic acid sequence is performed and the extraction of the signal for the first target nucleic acid sequence is performed by the mathematical Equation I-4, the threshold may be a positive value.

The threshold should be appropriately selected so as to avoid any misinterpretation of normally extracted signal into erroneously extracted signal, e.g., due to signal noises or fluctuations.

It should be understood by one of skill in the art that the threshold used in this step is distinct from a threshold used in determination of the presence of a target nucleic acid sequence as described hereinafter.

Step (bc-2): Determination of Progress or Termination of Procedures

When the extracted signal for the first target nucleic acid sequence or the second target nucleic acid sequence does not satisfy the accuracy criterion, the next step (c) is proceed; when the extracted signal for the first target nucleic acid sequence or the second target nucleic acid sequence satisfies the accuracy criterion, the method provides the extracted signal as an analytical signal without proceeding to the step (c).

In this step, the extracted signal satisfying the accuracy criterion is directly provided as an analytical signal, since it is considered to be correctly extracted. In contrast, the extracted signal not satisfying the accuracy criterion is subjected to the subsequent step, since it is considered to be erroneously extracted.

Meanwhile, after the extracted signal is analyzed to select a cycle having a maximum or minimum signal value, the following step is performed.

Step (d): Providing Signal Value(s) from Selected Cycle to End Cycle (S140; S240; S340; S440)

In the step (d), the signal value(s) from the selected cycle to the end cycle is provided as an analytical signal for determination of the presence of the first target nucleic acid sequence or the second target nucleic acid sequence.

The term "analytical signal" as used herein refers to a signal provided to determine the presence of a target nucleic acid sequence of interest. The term also refers to a signal that is finally used to determine the presence of a target nucleic acid sequence.

As explained above, the present inventors have found that the signal value(s) from the first cycle to the cycle immediately before the selected cycle (target-unrelated region) is negligible in determining the presence or absence of a target nucleic acid sequence of interest and the signal value(s) from the selected cycle to the end cycle (target-related region) is significant in determining the presence or absence of a target nucleic acid sequence of interest.

Based on the findings, only the target-related region is provided as an analytical signal for determining the presence of the target nucleic acid sequence in this step.

The signal value(s) from the selected cycle to the end cycle (target-related region) may be provided as an analytical signal with or without modification as follows:

(I) Providing Analytical Signal without Modification

Figure 6B:
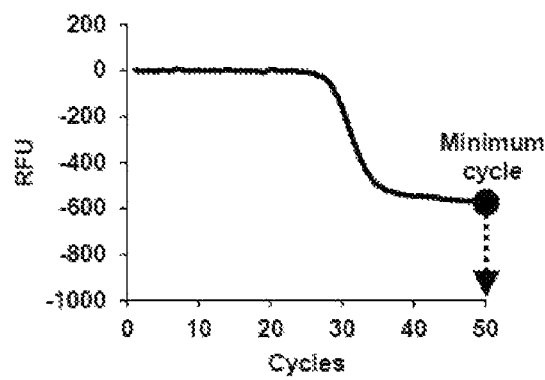
FIG. 6B represents four embodiments of this invention (middle left; middle right; bottom left; bottom right) for obtaining various analytical signals for determining the presence of a target nucleic acid sequence from the extracted signal of FIG. 6A.
Figure 6B:
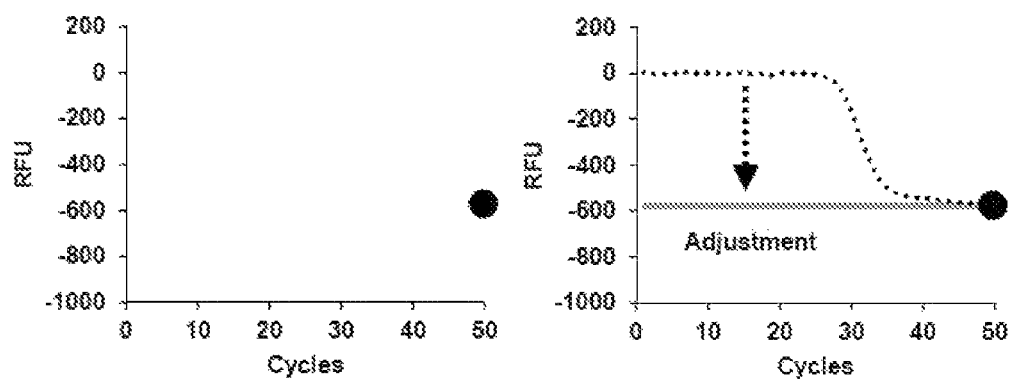
Figure 6B:
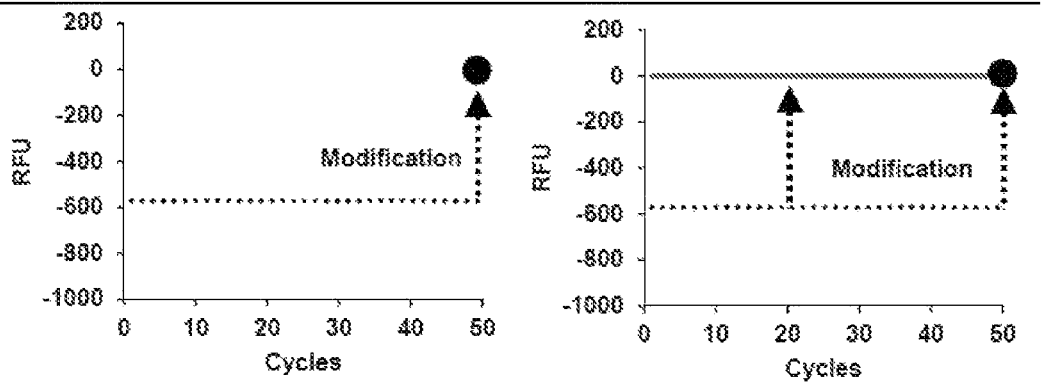
Figure 7B:
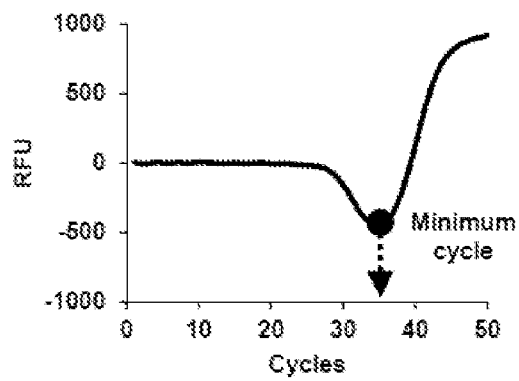
FIG. 7B represents four embodiments of this invention (middle left; middle right; bottom left; bottom right) for obtaining various analytical signals for determining the presence of a target nucleic acid sequence from the extracted signal of FIG. 7A.
Figure 7B:
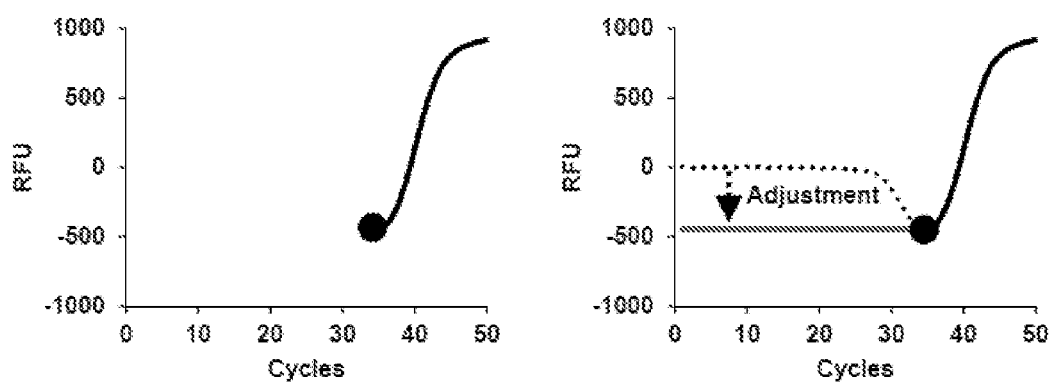
Figure 7B:
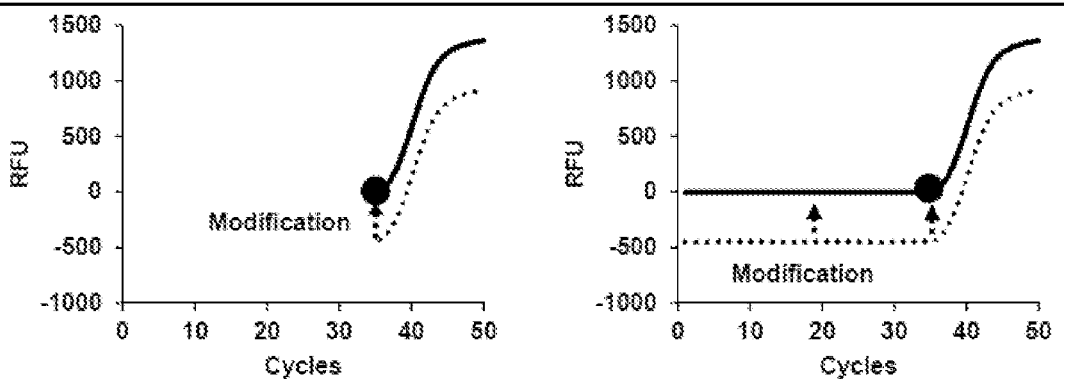

The signal value(s) from the selected cycle to the end cycle may be provided as an analytical signal, without modification thereof (see FIGS. 6B and 7B; middle left). In other words, the signal value(s) from the selected cycle to the end cycle per se may be used as an analytical signal for determining the presence of the target nucleic acid sequence.

The signal value(s) provided as an analytical signal without modification in the step (d) is used to determine the presence of a target nucleic acid sequence by a number of methods well known in the art.

In an embodiment, a predetermined threshold may be applied to the analytical signal provided without modification for determination of the presence of the target nucleic acid sequence.

It is to be understood by one of skill in the art that the threshold in the step (d) is different from the threshold for identifying an erroneously extracted signal in the step (bc-1).

For example, the threshold for determination of the presence of the target nucleic acid sequence may be set to RFU 100 so as to detect positive signals, whereas the threshold for identifying an erroneously extracted signal may be set to RFU −100 so as to detect negative signals.

For determination of the presence of the target nucleic acid sequence, the threshold applied to the analytical signal without modification may be determined in consideration of the magnitude of the maximum signal value or the minimum signal value.

Specifically, when a cycle having a maximum signal value is selected, the higher the maximum signal value is, the higher the threshold is; when a cycle having a minimum signal value is selected, the lower the minimum signal value is, the lower the threshold is.

When a cycle having a maximum signal value is selected, the magnitude of the maximum signal value is confirmed and then a threshold corresponding to the confirmed magnitude is determined; when a cycle having a minimum signal value is selected, the magnitude of the maximum signal value is confirmed and then a threshold corresponding to the confirmed magnitude is determined.

(ii) Providing Analytical Signal with Modification

The signal value(s) from the selected cycle to the end cycle may be modified prior to being provided as the analytical signal, followed by being applied to determination of the presence of the target nucleic acid sequence (see FIGS. 6B and 7B; bottom left). For this purpose, the method further comprises modifying the signal value(s) from the selected cycle to the end cycle prior to providing as the analytical signal.

The "modification" as used herein refers to a process by which a signal value(s) is converted into another signal value(s) by using a mathematical operation (addition, subtraction, multiplication, division, differentiation, integration, etc.).

The modification refers to a process performed in order to improve user's convenience in determining the presence of the target nucleic acid sequence.

The modification may be accomplished for all extracted signal, or may be accomplished only if certain criterion is met. The modification may be performed only when a signal value at the selected cycle is not within a certain range (e.g., around RFU 0). For example, in the case where a cycle having a maximum signal value is selected, the modification may be performed only if the selected cycle has a signal value higher than a certain value (e.g., RFU 0). In the case where a cycle having a minimum signal value is selected, the modification may be performed only if the selected cycle has a signal value lower than a certain value (e.g., RFU 0).

The modification of the signal may be performed using a number of methods known in the art, unless the modification adversely affects the determination of the presence or absence of the target nucleic acid sequence.

As one example, the modification comprises shifting the signal value(s) from the selected cycle to the end cycle upward or downward.

The "shift" or "shifting" as used herein is meant that the signal value(s) moves vertically with a same magnitude along the Y-axis.

According to an embodiment of the present invention, the modification comprises shifting the signal value(s) from the selected cycle to the end cycle upward such that the selected cycle has a signal value greater than a specific value and less than or equal to zero, or shifting the signal value(s) from the selected cycle to the end cycle downward such that the selected cycle has a signal value less than a specific value and greater than or equal to zero.

The specific value may be a nonzero value which is close to zero. Alternatively, when the steps (bc-1) and (bc-2) are further comprised, the specific value may be the threshold used in the step (bc-1).

In a particular embodiment of the present invention, the modification comprises shifting the signal value(s) from the selected cycle to the end cycle upward or downward such that the selected cycle has a signal value of zero.

Specifically, Where the present invention is applied to the MuDT1 technology (see WO 2015/147412), the modification, in particular shifting, may be performed as follows:

(i) When a signal-generating process in which the signal intensity increases with amplification of a target nucleic acid sequence is performed and the extraction of the signal for the second target nucleic acid sequence is performed by the mathematical Equation I-1, the modification comprises shifting the signal value(s) from the selected cycle to the end cycle upward such that the selected cycle has a signal value of zero; and (ii) When a signal-generating process in which the signal intensity increases with amplification of a target nucleic acid sequence is performed and the extraction of the signal for the second target nucleic acid sequence is performed by the mathematical Equation I-2, the modification comprises shifting the signal value(s) from the selected cycle to the end cycle downward such that the selected cycle has a signal value of zero.

Alternatively, where the present invention is applied to the MuDT2 technology (see WO 2016/093619) and the second reference value is greater than the first reference value, the modification, in particular shifting, may be performed as follows:

(i) When a signal-generating process in which the signal intensity increases with amplification of a target nucleic acid sequence is performed and the extraction of the signal for the second target nucleic acid sequence is performed by the mathematical Equation I-1, the modification comprises shifting the signal value(s) from the selected cycle to the end cycle upward such that the selected cycle has a signal value of zero;

(ii) When a signal-generating process in which the signal intensity increases with amplification of a target nucleic acid sequence is performed and the extraction of the signal for the second target nucleic acid sequence is performed by the mathematical Equation I-2, the modification comprises shifting the signal value(s) from the selected cycle to the end cycle downward such that the selected cycle has a signal value of zero;

(iii) When a signal-generating process in which the signal intensity increases with amplification of a target nucleic acid sequence is performed and the extraction of the signal for the first target nucleic acid sequence is performed by the mathematical Equation I-3, the modification comprises shifting the signal value(s) from the selected cycle to the end cycle downward such that the selected cycle has a signal value of zero;

(iv) When a signal-generating process in which the signal intensity increases with amplification of a target nucleic acid sequence is performed and the extraction of the signal for the first target nucleic acid sequence is performed by the mathematical Equation I-4, the modification comprises shifting the signal value(s) from the selected cycle to the end cycle upward such that the selected cycle has a signal value of zero;

(v) When a signal-generating process in which the signal intensity decreases with amplification of a target nucleic acid sequence is performed and the extraction of the signal for the second target nucleic acid sequence is performed by the mathematical Equation I-1, the modification comprises shifting the signal value(s) from the selected cycle to the end cycle downward such that the selected cycle has a signal value of zero;

(vi) When a signal-generating process in which the signal intensity decreases with amplification of a target nucleic acid sequence is performed and the extraction of the signal for the second target nucleic acid sequence is performed by the mathematical Equation I-2, the modification comprises shifting the signal value(s) from the selected cycle to the end cycle upward such that the selected cycle has a signal value of zero;

(vii) When a signal-generating process in which the signal intensity decreases with amplification of a target nucleic acid sequence is performed and the extraction of the signal for the first target nucleic acid sequence is performed by the mathematical Equation I-3, the modification comprises shifting the signal value(s) from the selected cycle to the end cycle upward such that the selected cycle has a signal value of zero; and (viii) When a signal-generating process in which the signal intensity decreases with amplification of a target nucleic acid sequence is performed and the extraction of the signal for the first target nucleic acid sequence is performed by the mathematical Equation I-4, the modification comprises shifting the signal value(s) from the selected cycle to the end cycle downward such that the selected cycle has a signal value of zero.

As another example, the modification may be performed by baselining (baseline-subtraction) (U.S. Pat. No. 8,219,324; US 2003/0148332; US 2006/0269947; KR 10-2012-0097215).

The signal value(s) from the selected cycle to the end cycle as an analytical signal does not contain a baseline region. Therefore, the baseline subtraction may be performed assuming that the signal value(s) from the first cycle to the cycle immediately before the selected cycle is a baseline region (background level). For example, if the selected cycle is the $35^{th}$ cycle, the baseline subtraction is performed assuming that the region from the 1st cycle to the 34th cycle is a baseline region.

The shifting and the baseline-subtraction as described above may yield the same result.

Figure 2:
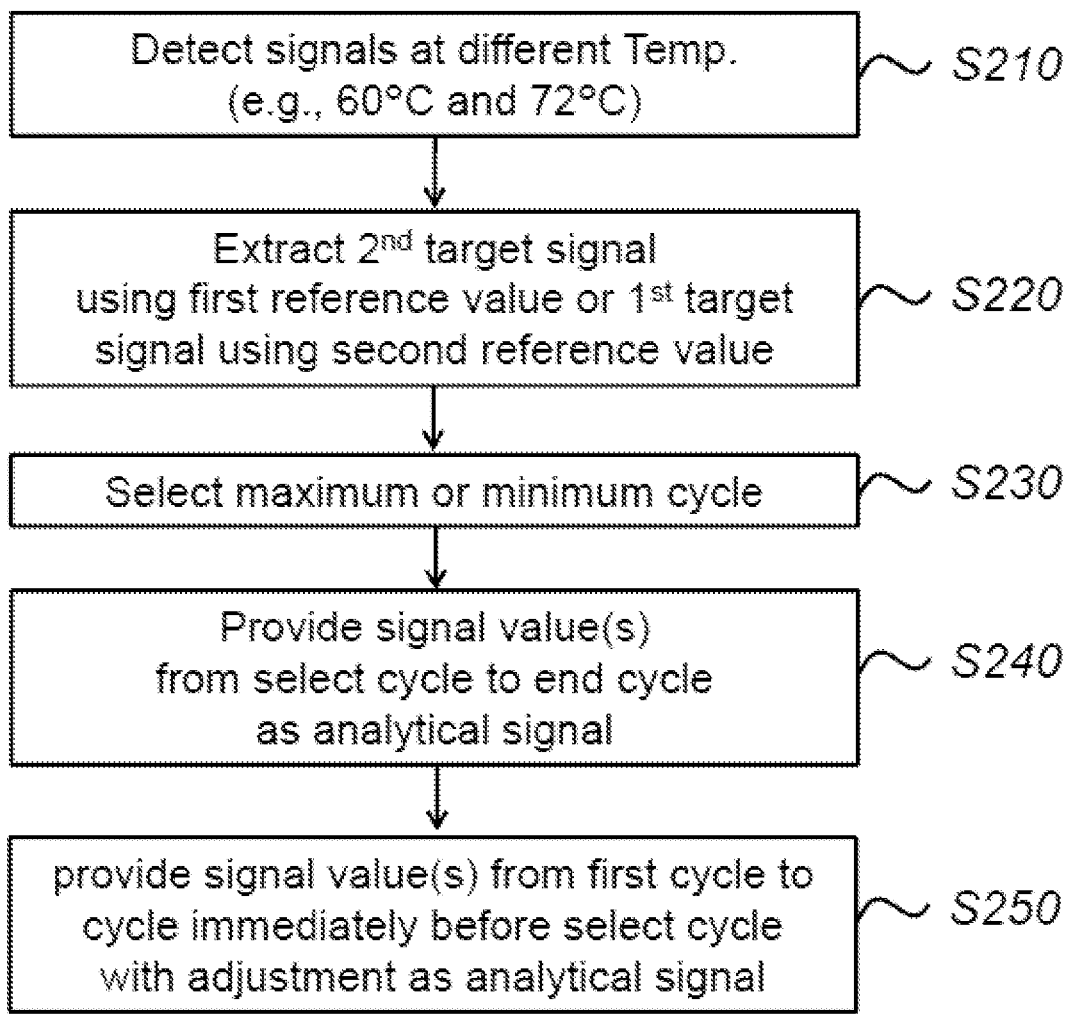
Figure 4:
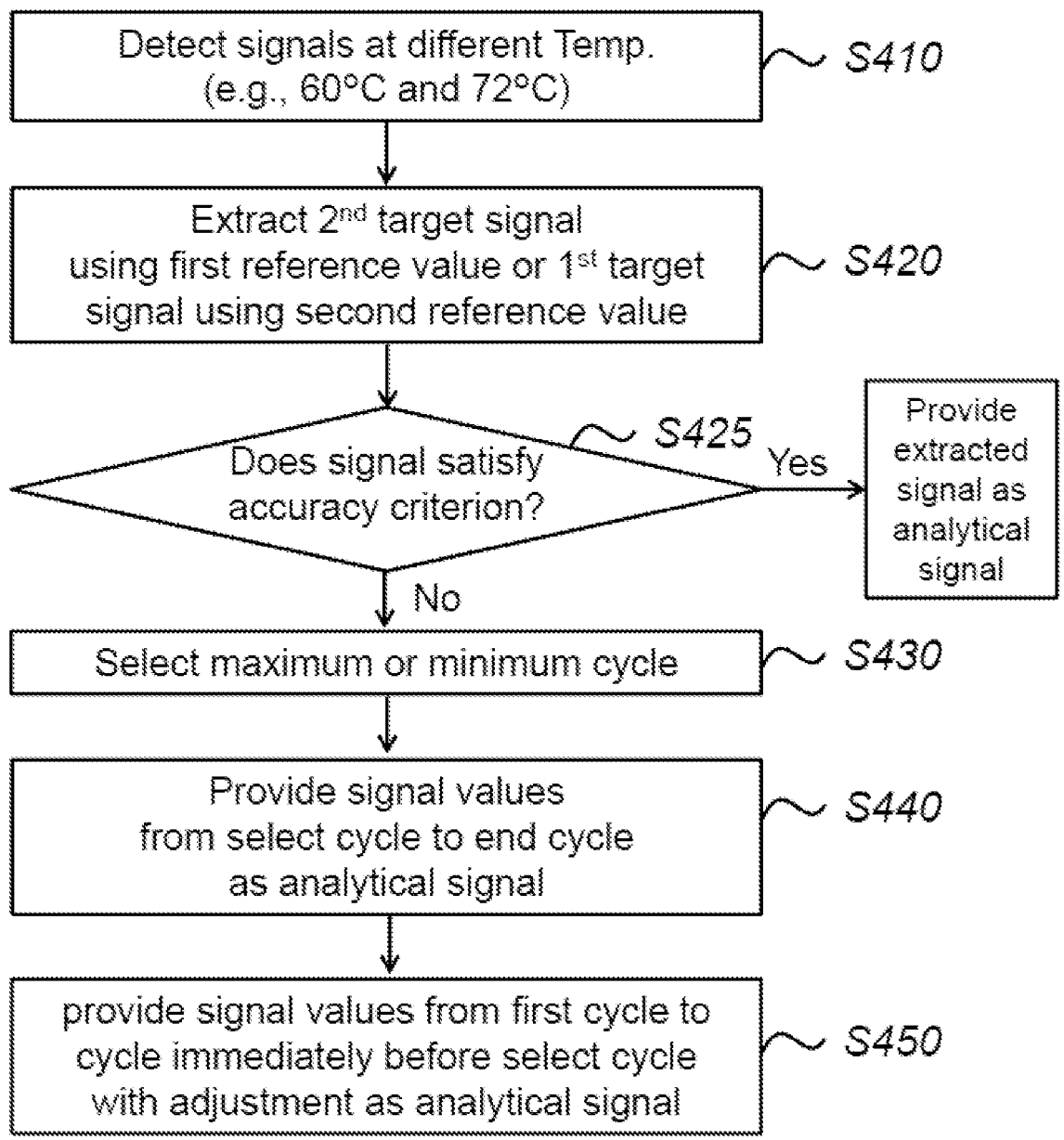

According to the present invention, a signal value(s) from a first cycle to a cycle immediately before the selected cycle may be further provided as an analytical signal after signal adjustment (see FIG. 2, S250 and FIG. 4, S450).

In an embodiment of the present invention, the method further comprises adjusting a signal value(s) from a first cycle to a cycle immediately before the selected cycle to the extent that the adjustment does not affect the determination of the presence of the first target nucleic acid sequence or the second target nucleic acid sequence and providing the adjusted signal value(s) in combination with the signal value(s) from the selected cycle to an end cycle as the analytical signal.

In other words, a target-unrelated region, i.e., a signal region from the first cycle to the cycle immediately before the selected cycle, may be adjusted and then further provided as an analytical signal.

The present inventors have found that the signal value(s) from the first cycle to the cycle immediately before the selected cycle is a target-unrelated region, and therefore the signal value(s) should be neglected in the determination of the presence of the target nucleic acid sequence, in order to obtain more accurate results. In addition, the present inventors have found that the signal value(s) from the first cycle to the cycle immediately before the selected cycle corresponds to a background region when being correctly extracted.

Therefore, in order to further provide the signal value(s) from the first cycle to the cycle immediately before the selected cycle as an analytical signal, the signal value(s) should be subjected to a signal adjustment process.

The term "adjust" or "adjustment" as used herein means that the signal value(s) is converted into a single value or values within a specific range.

In an embodiment of the present invention, the adjustment comprises adjusting the signal value(s) from the first cycle to the cycle immediately before the selected cycle to a background level (or background signal). The adjustment means a process in which the signal value(s) is converted to a signal that is generated in the absence of any target nucleic acid sequence or a process in which the signal value(s) is converted to a signal that is indicative of the absence of any target nucleic acid sequence.

In another embodiment of the present invention, the adjustment to background level comprises adjusting the signal value(s) from a first cycle to the cycle immediately before the selected cycle to be substantially identical to the signal value at the selected cycle.

The phrase "substantially identical to the signal value at the selected cycle" refers to a value within a certain range predetermined by considering the signal value at the selected cycle or a value equal to the signal value at the selected cycle.

In one example, the adjustment to background level comprises adjusting the signal value(s) from a first cycle to the cycle immediately before the selected cycle to be a value within a certain range predetermined by considering the signal value at the selected cycle.

In another example, the adjustment to background level comprises adjusting the signal value(s) from a first cycle to the cycle immediately before the selected cycle to be equal to the signal value at the selected cycle.

It is noted that the signal value(s) to be adjusted may comprise the signal value at the selected cycle. When the selected cycle is $35^{th}$ cycle, the signal values from the 1st cycle to the $35^{th}$ cycle may be adjusted. Alternatively, the signal values from the 1st cycle to the 34th cycle may be adjusted.

According to the present invention, the entire signal values comprising the adjusted signal value(s) from the first cycle to the cycle immediately before the selected cycle and the unadjusted signal value(s) from the selected cycle to the end cycle are provided as an analytical signal for determination of the presence of the target nucleic acid sequence.

For determination of the presence of the target nucleic acid sequence, the adjusted signal value(s) from the first cycle to the cycle immediately before the selected cycle may be directly provided without further modification (see FIGS. 6B and 7B; middle right), or may be provided with further modification (see FIGS. 6B and 7B; bottom right).

In an embodiment, the method further comprises modifying the adjusted signal value(s) from the first cycle to the cycle immediately before the selected cycle independently of the modification of the signal value(s) from the selected cycle to the end cycle.

In an embodiment, the method further comprises modifying the adjusted signal value(s) from the first cycle to the cycle immediately before the selected cycle and the signal value(s) from the selected cycle to the end cycle prior to providing as an analytical signal.

The modification includes a shifting or a baselining as described above.

As one example, the modification comprises shifting the adjusted signal value(s) from the first cycle to the cycle immediately before the selected cycle and the signal value(s) from the selected cycle to the end cycle upward or downward.

In an embodiment of the present invention, the modification comprises shifting the adjusted signal value(s) from the first cycle to the cycle immediately before the selected cycle and the signal values from the selected cycle to the end cycle upward such that the selected cycle has a signal value greater than a specific value and less than or equal to zero, or shifting the adjusted signal values from a first cycle to the cycle immediately before the selected cycle and the signal values from the selected cycle to the end cycle downward such that the selected cycle has a signal value less than a specific value and greater than or equal to zero; wherein the modified signal values from a first cycle to the cycle immediately before the selected cycle do not affect the determination of the presence of the first target nucleic acid sequence or the second target nucleic acid sequence (see FIGS. 6B & 7B, bottom right).

The specific value may be a nonzero value which is close to zero. Alternatively, the specific value may be the threshold used in the step (bc-1).

In an embodiment of the present invention, the modification comprises shifting the signals upward or downward such that the selected cycle has a signal value of zero.

As another example, the modification comprises baselining (baseline-subtraction).

The adjustment and the modification as described above may be combined with the use of the accuracy criterion.

Where the present invention is applied to the MuDT1 technology (see WO 2015/147412), it may be embodied as follows:

According to an embodiment, the first signal-generating means generates signals at the relatively high detection temperature and the relatively low detection temperature and the second signal-generating means generates a signal at the relatively low detection temperature, and the processing of the signal values in the step (b) comprises mathematically processing the signal values by using the first reference value to extract the signal for the second target nucleic acid sequence from the signals at the relatively low detection temperature obtained in the step (a).

According to an embodiment, the extraction of the signal for the second target nucleic acid sequence may be performed by the mathematical Equation I-1.

In an embodiment, the extracted signal is analyzed to select a cycle having a minimum signal value. Afterwards, the signal value(s) from the selected cycle to the end cycle is provided as an analytical signal for determination of the presence of the second target nucleic acid sequence.

In an embodiment, the method further comprises modifying the signal value(s) from the selected cycle to the end cycle prior to providing as an analytical signal.

In an embodiment, the method further comprises adjusting the signal value(s) from the first cycle to the cycle immediately before the selected cycle and then providing the adjusted signal value(s) in combination with the signal value(s) from the selected cycle to an end cycle as an analytical signal.

In an embodiment, the method further comprises modifying the adjusted signal value(s) from the first cycle to the cycle immediately before the selected cycle and the unadjusted signal value(s) from the selected cycle to the end cycle prior to providing as an analytical signal.

Alternatively, the first signal-generating means generates signals at the relatively high detection temperature and the relatively low detection temperature and the second signal-generating means generates a signal at the relatively low detection temperature, and the processing of the signal values in the step (b) comprises mathematically processing the signal values by using the first reference value to extract the signal for the second target nucleic acid sequence from the signal at the relatively high detection temperature obtained in the step (a).

According to an embodiment, the extraction of the signal for the second target nucleic acid sequence may be performed by the mathematical Equation I-2.

In an embodiment, the extracted signal is analyzed to select a cycle having a maximum signal value. Afterwards, the signal value(s) from the selected cycle to the end cycle is provided as an analytical signal for determination of the presence of the second target nucleic acid sequence.

In an embodiment, the signal value(s) from the selected cycle to the end cycle is modified prior to being provided as an analytical signal.

In an embodiment, the method further comprises adjusting the signal value(s) from the first cycle to the cycle immediately before the selected cycle and providing the adjusted signal value(s) in combination with the signal value(s) from the selected cycle to an end cycle as an analytical signal.

In an embodiment, the method further comprises modifying the adjusted signal value(s) from the first cycle to the cycle immediately before the selected cycle and the unadjusted signal value(s) from the selected cycle to the end cycle prior to providing as an analytical signal.

Where the present invention is applied to the MuDT2 technology (see WO 2016/093619), it may be embodied as follows:

According to an embodiment, the two signal-generating means generate signals at the relatively high detection temperature and the relatively low detection temperature.

More particularly, wherein the second reference value is greater than the first reference value; wherein (i) the processing of the signal values in the step (b) comprises mathematically extracting the signal for the second target nucleic acid sequence from the signal at the relatively low detection temperature in the step (a) by using the first reference value; (ii) the processing of the signal values in the step (b) comprises mathematically extracting the signal for the second target nucleic acid sequence from the signal at the relatively high detection temperature in the step (a) by using the first reference value; (iii) the processing of the signal values in the step (b) comprises mathematically extracting the signal for the first target nucleic acid sequence from the signal at the relatively low detection temperature in the step (a) by using the second reference value; or (iv) the processing of the signal values in the step (b) comprises mathematically extracting the signal for the first target nucleic acid sequence from the signal the signal at the relatively high detection temperature in the step (a) by using the second reference value.

Much more particularly, where the theoretically-predicted signal pattern is a positive pattern (e.g. increasing pattern), the extracted signal is analyzed to select a cycle having a minimum signal value. Afterwards, the signal from the selected cycle to the end cycle is provided as an analytical signal for determination of the presence of the second target nucleic acid sequence. Alternatively, where the theoretically-predicted signal pattern is a negative pattern (e.g. decreasing pattern), the extracted signal is analyzed to select a cycle having a maximum signal value. Afterwards, the signal from the selected cycle to the end cycle is provided as an analytical signal for determination of the presence of the second target nucleic acid sequence.

The method of the present invention can be used to provide an analytical signal for determining the presence of at least one of two target nucleic acid sequence. The expression "at least one of two target nucleic acid sequence" means either or both of the two target nucleic acid sequence.

Similarly, the method of the present invention can be used to provide analytical signals for determining the presence of three or more target nucleic acid sequence.

According to the MuDT1 technology and the MuDT2 technology, a signal for a target nucleic acid sequence can be extracted from signals for three or more target nucleic acid sequences by using a reference value, in a similar manner to the aforementioned method. In such cases, the inventive method can be also applied to provide an analytical signal for determination of the presence of the target nucleic acid sequence. According to the present invention, the signal value(s) from the selected cycle to the end cycle is provided as an analytical signal for determination of the presence of the target nucleic acid sequence.

In an embodiment for extracting a signal for a target nucleic acid sequence from signals for two target nucleic acid sequences in a sample, the two target nucleic acid sequences in the sample are those selected among three or more target nucleic acid sequences in the sample.

The present method can be involved in extraction of a signal for a target nucleic acid sequence in a reaction capable of generating three or more signals for three or more target nucleic acid sequences.

Furthermore, the signal extraction for three target nucleic acid sequences may be performed in a similar way to the signal extraction for two target nucleic acid sequences.

In other words, the signal extraction for a target nucleic acid sequence from signals for three or more target nucleic acid sequences in a sample may comprise an aspect of signal extraction for a target nucleic acid sequence from signals for two target nucleic acid sequences in a sample.

According to an embodiment, the method of the present invention can be used to provide an analytical signal for determining the presence of one or two of three or more target nucleic acid sequence.

As an example, a method for extracting a signal for a target nucleic acid sequence from signals for three target nucleic acid sequences in a sample is described in detail.

According to the MuDT1 technology, three signal-generating means (e.g., a first signal-generating means, a second signal-generating means and a third signal-generating means) and three detection temperature (e.g., a relatively high detection temperature, a relatively median detection temperature and a relatively low detection temperature) are employed.

The first signal-generating means generates signals at the relatively high detection temperature, the relatively median detection temperature and the relatively low detection temperature; the second signal-generating means generates signals at the relatively median detection temperature and the relatively low detection temperature; and the third signal-generating means generate signal at the relatively low detection temperature.

The sample is incubated with a first signal-generating means capable of generating a signal for a first target nucleic acid sequence, a second signal-generating means capable of generating a signal for a second target nucleic acid sequence, and a third signal-generating means capable of generating a signal for a second target nucleic acid sequence in a single reaction vessel and detecting signals at a relatively high detection temperature, a relatively median detection temperature and a relatively low detection temperature by the single type of detector. Afterwards, the signal detected at the relatively high detection temperature and the signal detected at the relatively median detection temperature are mathematically processed by using a first reference value to extract the signal for the second target nucleic acid sequence; wherein the first reference value is a value representing a relationship of change in signals provided by the first signal-generating means at the relatively high detection temperature and the relatively median detection temperature. The suitability of the first reference value is verified.

Then, if it is determined that one of the first target nucleic acid sequence and the second target nucleic acid sequence is absent from a result of the above extraction step, a signal extraction from the signals detected at the relatively low detection temperature and the signal detected at the relatively median detection temperature can be performed according to the present method as if there may be two target nucleic acid sequences in the sample.

Meanwhile, if it is determined that both of the first target nucleic acid sequence and the second target nucleic acid sequence are present, the present method can be applied with modifications as follows: the signal detected at the relatively low detection temperature and the signal detected at the relatively median detection temperature are mathematically processed by using a reference value for a mixture of the first target nucleic acid sequence and the second target nucleic acid sequence to extract the signal for the third target nucleic acid sequence; wherein the reference value for a mixture of the first target nucleic acid sequence and the second target nucleic acid sequence is a value representing a relationship of change in signals provided by the first signal-generating means and the second signal-generating means at the relatively median detection n temperature and the relatively low detection temperature.

Afterwards, the extracted signal for the second target nucleic acid sequence and the extracted signal for the third target nucleic acid sequence are each subjected to the step (c) of the method of the present invention.

As such, the signal extraction for three target nucleic acid sequences may be performed in a similar way to the signal extraction for two target nucleic acid sequences.

Therefore, it would be appreciated by one of skill in the art that the inventive method can be used to extract signals for three or more target nucleic acid sequences, with a slight modification thereof.

According to an embodiment, the incubation comprises a plurality of incubations and analytical signals for the incubations are individually provided.

The term used herein "a plurality of incubations" means incubations undertaken in different reaction vessels, tubes or wells. The advantages of the present invention become more highlighted for a plurality of incubations. Assumed that a plurality of incubations comprises certain combinations of "NG" target sequence and "CT" target sequence in unknown amounts, it would be general that the plurality of incubations is analyzed by using a single reference value for each target nucleic acid sequence. The present inventors have found that such utilization of a single reference value is likely to lead to erroneous detection results. According to an embodiment, a reference value for "NG" target sequence or a reference value for "CT" target sequence are applied to all of the incubations and then analytical signals are individually provided from the individual incubations if needed.

II. Storage Medium, Computer Program and Device for Signal Extraction

Since the storage medium, the device and the computer program of the prevent invention described hereinbelow are intended to perform the present methods in a computer, the common descriptions between them are omitted in order to avoid undue redundancy leading to the complexity of this specification.

In another aspect of this invention, there is provided a computer readable storage medium containing instructions to configure a processor to perform a method for providing an analytical signal for a target nucleic acid sequence in a sample, the method comprising:

(a) receiving signals from the sample at a relatively high detection temperature and a relatively low detection temperature; wherein the first target nucleic acid sequence in the sample is detected by a first signal-generating means and the second target nucleic acid sequence in the sample is detected by a second signal-generating means; wherein the detection is performed at one or more cycles of the signal-generating process to obtain a signal value at each of the one or more cycles; wherein the two signals to be generated by the two signal-generating means are not differentiated by a single type of detector;

(b) processing the signal values obtained in the step (a) by using a second reference value to extract the signal for the first target nucleic acid sequence or processing the signal values obtained in the step (a) by using a first reference value to extract the signal for the second target nucleic acid sequence; wherein the first reference value is a value representing a relationship of change in signals provided by the first signal-generating means at the relatively high detection temperature and the relatively low detection temperature, and the second reference value is a value representing a relationship of change in signals provided by the second signal-generating means at the relatively high detection temperature and the relatively low detection temperature; wherein the first reference value is determined from a control reaction using the first target nucleic acid sequence and the first signal-generating means and the second reference value is determined from a control reaction using the second target nucleic acid sequence and the second signal-generating means;

(c) selecting a cycle having a maximum signal value or a minimum signal value in the extracted signal for the first target nucleic acid sequence or the second target nucleic acid sequence; and (d) providing a signal value(s) from the selected cycle to an end cycle as an analytical signal for determination of the presence of the first target nucleic acid sequence or the second target nucleic acid sequence.

According to an embodiment, the first reference value (or the second reference value) is stored in the computer readable storage medium. According to an embodiment, the computer readable storage medium contains instructions to input the first reference value (or the second reference value) in performing the method. According to an embodiment, the computer readable storage medium further contains instructions to configure a processor to perform a method for obtaining the first reference value (or the second reference value).

In still another aspect of this invention, there is provided a computer program to be stored on a computer readable storage medium to configure a processor to perform a method for providing an analytical signal for a target nucleic acid sequence in a sample, the method comprising:

(a) receiving signals from the sample at a relatively high detection temperature and a relatively low detection temperature; wherein the first target nucleic acid sequence in the sample is detected by a first signal-generating means and the second target nucleic acid sequence in the sample is detected by a second signal-generating means; wherein the detection is performed at one or more cycles of the signal-generating process to obtain a signal value at each of the one or more cycles; wherein the two signals to be generated by the two signal-generating means are not differentiated by a single type of detector;

(b) processing the signal values obtained in the step (a) by using a second reference value to extract the signal for the first target nucleic acid sequence or processing the signal values obtained in the step (a) by using a first reference value to extract the signal for the second target nucleic acid sequence; wherein the first reference value is a value representing a relationship of change in signals provided by the first signal-generating means at the relatively high detection temperature and the relatively low detection temperature, and the second reference value is a value representing a relationship of change in signals provided by the second signal-generating means at the relatively high detection temperature and the relatively low detection temperature; wherein the first reference value is determined from a control reaction using the first target nucleic acid sequence and the first signal-generating means and the second reference value is determined from a control reaction using the second target nucleic acid sequence and the second signal-generating means;

(c) selecting a cycle having a maximum signal value or a minimum signal value in the extracted signal for the first target nucleic acid sequence or the second target nucleic acid sequence; and (d) providing a signal value(s) from the selected cycle to an end cycle as an analytical signal for determination of the presence of the first target nucleic acid sequence or the second target nucleic acid sequence.

According to an embodiment of the present invention, the computer program contains the first reference value (or the second reference value). According to an embodiment of the present invention, the computer program contains instructions to input the first reference value (or the second reference value) in performing the method. According to an embodiment of the present invention, the computer program further contains instructions to configure a processor to perform a method for obtaining the first reference value (or the second reference value).

The program instructions are operative, when performed by the processor, to cause the processor to perform the present method described above. The program instructions for performing the present method may comprise an instruction to receive signal values from the signal-generating process with the sample at the relatively high detection temperature and the relatively low detection temperature; an instruction to process the signal values received for extracting a signal; an instruction to select a cycle having a maximum signal value or a minimum signal value; and an instruction to provide signal value(s) from the selected cycle to an end cycle as an analytical signal. According to an embodiment, the program instructions for performing the present method may further comprise an instruction to obtain the first reference value (or the second reference value).

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The signal values from the signal-generating process may be received through several mechanisms. For example, the signal values may be acquired by a processor resident in a PCR data acquiring device. The signal values may be provided to the processor in real time as the signal values are being collected, or it may be stored in a memory unit or buffer and provided to the processor after the experiment has been completed. Similarly, the signal values may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system.

After the signal values have been received or acquired, the processing of the signal values undertakes to extract the signal for the first target nucleic acid sequence by the second reference value or to extract the signal for the second target nucleic acid sequence by the first reference value. The processor selects a cycle having a maximum signal value or a minimum signal value and provides signal value(s) from the selected cycle to an end cycle as an analytical signal.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In a further aspect of this invention, there is provided a device for providing an analytical signal for a target nucleic acid sequence in a sample, comprising (a) a computer processor and (b) the computer readable storage medium described above coupled to the computer processor.

According to an embodiment, the device further comprises a reaction vessel to accommodate the sample and signal-generating means, a temperature controlling means to control temperatures of the reaction vessel and/or a detector to detect signals at cycles.

According to an embodiment, the computer processor permits not only to receive a signal value at one or more cycles of the signal-generating process but also to process the signal values obtained for signal extraction by reference values and selects a cycle having a maximum signal value or a minimum signal value. The processor may be prepared in such a manner that a single processor can do several performances. Alternatively, the processor unit may be prepared in such a manner that several processors do the several performances, respectively.

According to an embodiment, the processor may be embodied by installing software into conventional devices for detection of target nucleic acid sequences (e.g. real-time PCR device).

For example, the present device may be embodied into a real-time PCR system. The system comprises a real-time PCR device for performing a real-time PCR amplification, and a computer system as a logic system connected to the real-time PCR device via a cable for extracting signal and displaying the correction resultants. The computer system may display the extraction resultants in various forms such as graphs, tables and words according to demands of users. The computer system may comprise instructions contained in a computer readable storage medium for performing the present method. The real-time PCR device and the computer system may be integrated into a system.

The signal values may be received with amplification curves in various fashions. For example, the signal values may be received and collected by a processor in a data collector of the real-time PCR device. Upon collecting the signal values, they may be provided to a processor in a real-time manner, or stored in a memory unit or buffer and then provided to a processor after experiments.

Likely, the signal values may be provided from the real-time PCR device to the computer system such as a desktop computer system via network connection (e.g., LAN, VPN, intranet and internet) or direct connection (e.g., USB and wired or wireless direct connections), or via portable media such as CD, DVD, floppy disk and portable HDD. Alternatively, the signal values may be provided to a server system via network connections (e.g., LAN, VPN, intranet, internet and wireless communication network) connected to a client such as notebook and desktop computer systems.

After the signal values are received or obtained, a signal-value processor proceeds to extract the signal by reference values. The signal extraction of the present invention may be undertaken by an application (i.e., program) installed into the computer system. Alternatively, it may be made by an application directly installed into the computer system through application store server or application provider servers in which the application is operable in an operating system of the computer system. The operating system includes Window, Macintosh and mobile operating systems such as iOS and Android that are installed into mobile terminals such as Smartphones and Tablet PC.

As described above, the present method for signal extraction may be embodied by an application (i.e., program) supplier-installed or user-direct installed into the computer system, and recorded in a computer readable storage medium.

A computer program embodying the present method may implement all functions for signal extraction. The computer program may a program comprising program instructions stored on a computer readable storage medium to configure a processor to perform the present method.

The computer program may be coded by using suitable computer languages such as C, C++, JAVA, Visual basic, VBScript, JavaScript, Perl, XML and machine languages. The program codes may include function codes for mathematical functions described above and control codes for implementing process in order by a processor of the computer system.

The codes may further comprise memory reference codes by which additional information or media required in implementing the above-described functions by the processor is referred at location (address) of internal or external memory of the computer system.

When the computer system requires communication with another computer or server in remote for implementing functions of the processor, the codes may further comprise communication-relating codes encoding how the processor is communicated with another computer or server in remote by using communication module (e.g., wired and/or wireless communication module) or what information or media is transmitted.

Functional programs and codes (code segments) for embodying the present invention may be easily inferred or modified by programmers in the art in considering system environments of computers reading storage media and executing programs.

The storage medium network-connected to the computer system may be distributed and computer-readable codes may be stored and executed in a distribution manner. In such case, at least one computer among a plurality of distributed computers may implement a portion of the functions and transmit results of the implementation to at least one computer that may also implement a portion of the functions and transmit results of the implementation to at least one computer.

The storage medium in which application (i.e., program) is recorded for executing the present invention includes a storage medium (e.g., hard disk) contained in application store servers or application provider servers, application provider servers per se, another computer having the program and its storage medium.

The computer system capable of reading the storage medium may include general PC such as desk top or notebook computers, mobile terminals such as Smartphone, Tablet PC, PDA (Personal Digital Assistants) and mobile communication terminals as well as all computing-executable devices.

III. Detection of Target Nucleic Acid

The analytical signal for the target nucleic acid sequence may be employed in the detection thereof. The detection of the target nucleic acid sequence comprises the determination of the presence of the target nucleic acid sequence in a sample. The target detection may be accomplished by various methods known in the art. For example, the target detection may be accomplished by applying a threshold to the plot of the extracted signal, and identifying whether there is a crossing point between the plot and the threshold. If there is a crossing point, the presence of the target nucleic acid sequence is determined; and if there is no crossing point, the absence of the target nucleic acid sequence is determined.

The features and advantages of this invention will be summarized as follows:

(a) The present invention allows detection of a target nucleic acid sequence in a more accurate, effective and reproducible manner, by removing or adjusting a signal region that may erroneously affect the detection of a target nucleic acid sequence.

(b) The present invention can contribute to dramatic improvement in methods for detecting target nucleic acid sequences using different detection temperatures and reference values.

(c) In particular, in the case of RNA target detection using a degenerate primer set or lower concentration of a target nucleic acid sequence having a relatively low detection temperature, the usefulness of the present invention becomes more prominent.

(d) According to the present invention, more accurate signal extraction for detecting a target nucleic acid sequence is practical by developing a computer program for performing the present method.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Signal Detection and Extraction Based on MuDT1 Technology

According to an embodiment of MuDT1 technology (see WO 2015/147412), the first signal-generating means generates signals at the relatively high detection temperature and the relatively low detection temperature and the second signal-generating means generates a signal at the relatively low detection temperature, and the processing of the signal values is performed using the first reference value to extract the signal for the second target nucleic acid sequence from the signal at the relatively low detection temperature.

<1-1> Preparation of Templates and Oligonucleotides

The PTOCE method (WO 2012/096523) was used as a real-time PCR approach for detecting signals in a real-time manner at different detection temperatures.

Taq DNA polymerase having a 5' nuclease activity was used for the extension of upstream primers and downstream primers, the cleavage of PTO (Probing and Tagging Oligonucleotide), and the extension of PTO fragment. Genomic DNA of *Neisseria gonorrhoeae* (NG) and genomic DNA of *Chlamydia trachomatis* (CT) were used as target nucleic acid sequences.

The PTOs for detection of NG and CT by using the PTOCE method as signal-generating means comprise (i) a 5'-tagging portion comprising a nucleotide sequence non-complementary to the target nucleic acid sequence and (ii) a 3'-targeting portion comprising a hybridizing nucleotide sequence complementary to the target nucleic acid sequence. The CTOs (Capturing and Templating Oligonucleotides) comprise, in a 3' to 5' direction, (i) a capturing portion comprising a nucleotide sequence complementary to the 5'-tagging portion or a part of the 5'-tagging portion of the PTOs and (ii) a templating portion comprising a nucleotide sequence non-complementary to the 5'-tagging portion and the 3'-targeting portion of the PTOs. The CTOs were labeled with a quencher molecule (BHQ-2) at their 5'-ends and a fluorescent reporter molecule (CAL Fluor Red 610) in their templating portions. The PTOs and CTOs are blocked with a carbon spacer at their 3'-ends to prohibit their extension.

Because the PTOCE real-time method uses a single fluorescence label (CAL Fluor Red 610) for detecting two different target nucleic acid sequences, signals for the two target nucleic acid sequences cannot be differentiated from each other in a single reaction vessel by a single detector.

In the PTOCE real-time method, when a target sequence is present, the PTO hybridized with the target sequence is cleaved and a PTO fragment is produced. The PTO fragment is then annealed to the capturing portion of the CTO, extended on the templating portion of the CTO and forms an extended duplex with the CTO (Duplexed CTO). The formation of the extended duplex provides a signal and an amplification curve can be obtained by measuring the signal at the extended duplex-forming temperature.

In this Example, the sequence and length of each extended duplex was designed such that the extended duplex for CT can be formed at 72° C. and the extended duplex for NG can be formed at 60° C. not at 72° C.

Accordingly, at the detection temperature of 72° C., only the signal for CT is detected, whereas at the detection temperature of 60° C., the signal for NG as well as the signal for CT is detected.

The sequences of upstream primers, downstream primers, PTOs, and CTOs used in this Example are described in Table 1.

TABLE 1

| Name | Type | Sequence (5' → 3') | SEQ ID |
|---|---|---|---|
| NG_F | Primer | TACGCCTGCTACTTTCAC GCTIIIIGTAATCAGAT G | SEQ ID NO: 1 |
| NG_R | Primer | CAATGGATCGGTATCACT CGCIIIIICGAGCAAGAA C | SEQ ID NO: 2 |
| NG_PTO | PTO | GTACGCGATACGGGCCCC TCATTGGCGTGTTTCG [C3 spacer] | SEQ ID NO: 3 |
| NG_CTO | CTO | [BHQ-2]TTTTTTTTTT TTTTTTTTG[T(Cal Fluor Red 610)]ACT GCCCGTATCGCGTAC [C3 spacer] | SEQ ID NO: 4 |
| CT_F | Primer | GAGTTTTAAAATGGGAAA TTCTGGTIIIIITTTGTA TAAC | SEQ ID NO: 5 |
| CT_R | Primer | CCAATTGTAATAGAAGCA TTGGTTGIIIIITTATTG GAGA | SEQ ID NO: 6 |
| CT_PTO | PTO | GATTACGCGACCGCATCA GAAGCTGTCATTTTGGCT GCG[C3 spacer] | SEQ ID NO: 7 |
| CT_CTO | CTO | [BHQ-2]GCGCTGGATAC CCTGGACGA[T(Cal Fluor Red 610)]ATG TGCGGTCGCGTAATC[C3 spacer] | SEQ ID NO: 8 |

I: Deoxyinosine
PTO: Probing and Tagging Oligonucleotide
CTO: Capturing and Templating Oligonucleotide
BHQ: Quencher (Black Hole Quencher)
Underlined letter: 5'-tagging portion of PTO <1-2> Real-Time PCR and Signal Detection at Different Temperatures The real-time PCR in accordance with the PTOCE method was conducted in the final volume of 20 μl containing a target nucleic acid (100 fg of NG genomic DNA, 10 pg of CT genomic DNA, a mixture of 100 fg of NG genomic DNA and 10 pg of CT genomic DNA), 5 pmole of upstream primer (SEQ ID NO:1), 5 pmole of downstream primer (SEQ ID NO:2), 3 pmole of PTO (SEQ ID NO:3) and 1 pmole of CTO (SEQ ID NO:4) for NG target amplification, 5 pmole of upstream primer (SEQ ID NO:5), 5 pmole of downstream primer (SEQ ID NO:6), 3 pmole of PTO (SEQ ID NO:7) and 1 pmole of CTO (SEQ ID NO:8) for CT target amplification, and 5 μl of 4× Master Mix (final conc., 200 μM dNTPs, 2 mM MgCl2, 2 U of Taq DNA polymerase) (Enzynomics, Korea). The tubes containing the reaction mixture were placed on the real-time thermocycler (CFX96 Real-time Cycler, Bio-Rad) for 5 min at 50° C., denatured for 15 min at 95° C. and subjected to 50 cycles of 30 sec at 95° C., 60 sec at 60° C., 30 sec at 72° C. Detection of signals was performed at 60° C. and 72° C. at each cycle. The results are represented by FIG. 5.

Figure 5:
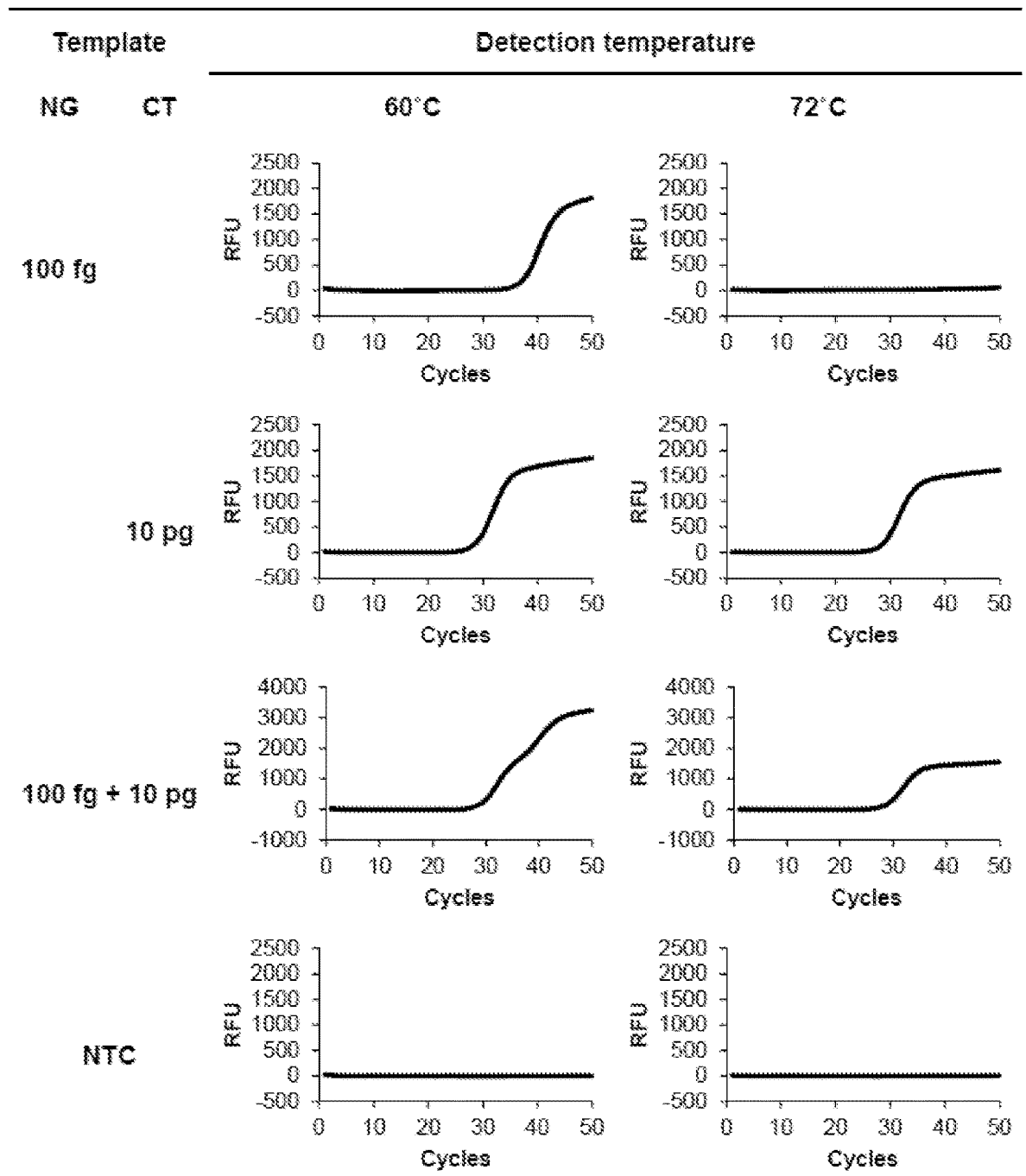
FIG. 5 represents signals detected at different detection temperatures of 60° C. and 72° C. in accordance with MuDT1 Technology (see WO 2015/147412) using a PTOCE real-time PCR method, for samples containing 100 fg of genomic DNA of *Neisseria gonorrhoeae* (NG), 10 pg of genomic DNA of *Chlamydia trachomatis* (CT), a mixture of 100 fg of NG and 10 pg of CT, and NTC (no target control).

As shown in FIG. 5, the sample containing only NG target (100 fg) exhibited a signal at 60° C. but not at 72° C. (see 1st row); the sample containing only CT target (10 pg) exhibited signals at both 60° C. and at 72° C. (see 2nd row); the sample containing both NG and CT targets (100 fg NG+10 pg CT) exhibited signals at both 60° C. and at 72° C. (see 3rd row); and the sample containing no target (NTC) exhibited no signals at 60° C. and at 72° C. (see 4th row).

<1-3> Extraction of Signal for a Target Nucleic Acid Sequence

As represented in FIG. 5, signals for CT target can be directly taken from signals detected at 72° C., since signals for NG target are not detected at 72° C. In contrast, signals for NG target are not detected at 72° C. but at 60° C. together with signals for CT target, and signals for CT target has to be therefore removed from signals at 60° C. for extraction of signals for NG target. It is noted that the signal intensities for target nucleic acid, particularly CT, vary depending upon the temperatures for detection, i.e., the intensity of signals at 60° C. may be higher than that at 72° C. Accordingly, signals for CT target detected at 72° C. should be appropriately transformed into signals to be expected at 60° C. For this purpose, a reference value was used in this method.

Specifically, signals for NG target can be extracted by using a reference value representing a relationship of change in signals at 72° C. and 60° C. for CT target in accordance with the Equation I-1:

Extracted signal for the second target nucleic acid sequence=[signal at the relatively low detection temperature]−[(signal at the relatively high detection temperature)×(first reference value)];   <Equation I-1> wherein, the second target nucleic acid sequence is NG target, the relatively low detection temperature is 60° C. and the relatively high detection temperature is 72° C. and the first reference value is a reference value for CT target.

The extracted signal for NG target can be plotted.

A reference value for CT target may be calculated in accordance with the Equation II-1:

Reference value for CT target=[signal at 60° C. for a control sample containing only CT target]÷[signal at 72° C. for a control sample containing only CT target]   <Equation II-1>

The reference value for CT target may vary depending upon the condition of the reaction. Accordingly, some different reference values for CT may be obtained from iterative experiments. That is, the reference value for CT may be obtained in a certain range of values from a control sample containing only CT target.

It would be general to one of skill in the art that reference values for CT target are obtained in a certain range from a control sample containing only CT target and a single suitable reference value among the reference values is suitably selected to remove signals for CT target from signals at 60° C. The present inventors have found that the application of the single reference value for CT target to all reactions may cause erroneous signals when the single reference value is unsuitable to an individual reaction.

For example, FIG. 6A represents an embodiment of a signal extraction for NG target in the sample containing 10 pg of CT target. A signal for the second target nucleic acid sequence (NG) was extracted by using (i) a reference value for the first target nucleic acid sequence (CT) of 1.50 and (ii) signals detected at the relatively low detection temperature (60° C.) and the relatively high detection temperature (72° C.), in accordance with the mathematical Equation I-1. As the sample contains only CT target, the signal for NG target extracted by removal of CT target signal should be theoretically around RFU 0 at all cycles when a suitable reference value for CT target is applied. Unlike such expectation, the application of the reference value for CT target (1.50) generated an erroneous signal significantly lower than RFU 0 due to removal of signals larger than signals originated from CT target.

As another example, FIG. 7A represents an embodiment of a signal extraction for NG target in the sample containing 100 fg of NG and 10 pg of CT target. A signal for the second target nucleic acid sequence (NG) was extracted by using (i) a reference value for the first target nucleic acid sequence (CT) of 1.50 and (ii) signals detected at the relatively low detection temperature (60° C.) and the relatively high detection temperature (72° C.), in accordance with the mathematical Equation I-1. In FIG. 7A, a portion of the resulting extracted signal shows a theoretically-unpredicted pattern (below RFU 0).

These results demonstrate that when a single reference value is applied to all reactions for signal extraction for a target nucleic acid sequence, erroneous signals may be generated due to unsuitability of the reference value to certain reactions.

Example 2: Providing an Analytical Signal for Determination of the Presence of a Target Nucleic Acid Sequence Based on MuDT1 Technology It has been verified that the present method can provide an analytical signal for determination of the presence of a target nucleic acid sequence, even though the extracted signal contains an erroneous signal.

FIG. 6B represents four embodiments of this invention (middle left; middle right; bottom left; bottom right) for obtaining various analytical signals for determining the presence of a target nucleic acid sequence from the extracted signal of FIG. 6A. According to a first embodiment of the present invention, a cycle having the minimum signal value (indicated as "Minimum cycle"; corresponding to $50^{th}$ cycle) is selected (top left); signal value(s) from the selected cycle to the end cycle (the select cycle and the end cycle are both $50^{th}$ cycle) is provided as an analytical signal for determining the presence of NG (middle left). According to a second embodiment of the present invention, a cycle having the minimum signal value (indicated as "Minimum cycle"; corresponding to $50^{th}$ cycle) is selected (top left); signal value(s) from the selected cycle to the end cycle ($50^{th}$ cycle) is further modified (e.g., shifted) and then provided as an analytical signal for determining the presence of NG (bottom left). According to a third embodiment of the present invention, a cycle having the minimum signal value (indicated as "Minimum cycle"; corresponding to $50^{th}$ cycle) is selected (top right); signal value(s) from the first cycle to the cycle immediately before the selected cycle (from the $1^{st}$ cycle to the $49^{th}$ cycle) is adjusted to be equal to the signal value at the selected cycle; the adjusted signal value(s) from the first cycle to the cycle immediately before the selected cycle (from the $1^{st}$ cycle to the $49^{th}$ cycle) and the signal value(s) from the selected cycle to the end cycle ($50^{th}$ cycle) are provided together as an analytical signal for determining the presence of NG (middle right). According to a fourth embodiment of the present invention, a cycle having the minimum signal value (indicated as "Minimum cycle"; corresponding to $50^{th}$ cycle) is selected (top right); signal value(s) from the first cycle to the cycle immediately before the selected cycle (from the $1^{st}$ cycle to the $49^{th}$ cycle) is adjusted to be equal to the signal value at the selected cycle; the adjusted signal value(s) from the first cycle to the cycle immediately before the selected cycle (from the $1^{st}$ cycle to the $49^{th}$ cycle) and the signal value(s) from the selected cycle to the end cycle ($50^{th}$ cycle) are further modified (e.g., shifted) and then provided as an analytical signal for determining the presence of NG (bottom right).

FIG. 7B represents four embodiments of this invention (middle left; middle right; bottom left; bottom right) for obtaining various analytical signals for determining the presence of a target nucleic acid sequence from the extracted signal of FIG. 7A. According to a first embodiment of the present invention, a cycle having the minimum signal value (indicated as "Minimum cycle"; corresponding to $35^{th}$ cycle) is selected (top left); signal value(s) from the selected cycle to the end cycle (from $35^{th}$ cycle to $50^{th}$ cycle) is provided as an analytical signal for determining the presence of NG (middle left). According to a second embodiment of the present invention, a cycle having the minimum signal value (indicated as "Minimum cycle"; corresponding to $35^{th}$ cycle) is selected (top left); signal value(s) from the selected cycle to the end cycle (from $35^{th}$ cycle to $50^{th}$ cycle) is further modified (e.g., shifted) and then provided as an analytical signal for determining the presence of NG (bottom left). According to a third embodiment of the present invention, a cycle having the minimum signal value (indicated as "Minimum cycle"; corresponding to $35^{th}$ cycle) is selected (top right); signal value(s) from the first cycle to the cycle immediately before the selected cycle (from 1st cycle to 34th cycle) is adjusted to be equal to the signal value at the selected cycle; the adjusted signal value(s) from the first cycle to the cycle immediately before the selected cycle (from 1st cycle to 34th cycle) and the signal value(s) from the selected cycle to the end cycle (from $35^{th}$ cycle to $50^{th}$ cycle) are provided together as an analytical signal for determining the presence of NG (middle right). According to a fourth embodiment of the present invention, a cycle having the minimum signal value (indicated as "Minimum cycle"; corresponding to $35^{th}$ cycle) is selected (top right); signal value(s) from the first cycle to the cycle immediately before the selected cycle (from 1st cycle to 34th cycle) is adjusted to be equal to the signal value at the selected cycle; the adjusted signal value(s) from the first cycle to the cycle immediately before the selected cycle (from 1st cycle to 34th cycle) and the signal value(s) from the selected cycle to the end cycle (from $35^{th}$ cycle to $50^{th}$ cycle) are further modified (e.g., shifted) and then provided as an analytical signal for determining the presence of NG (bottom right).

In FIGS. 6B and 7B above, it is noted that a cycle having a minimum signal value were selected, because suitably extracted signal for a target nucleic acid sequence of interest is expected to exhibit an increasing signal pattern in the presence of the target nucleic acid sequence in a sample. However, it will be appreciated by those skilled in the art that a cycle having a maximum signal value may be selected instead, depending upon the signal-generating process and the extraction process used in the step (b).

In order to demonstrate the applicability of the present method, extracted signals for NG targets (by using various reference values, e.g., 1.15, 1.50, 2.00, and 2.50) shown on the left column of FIGS. 8A to 8D were employed.

<2-1> Selection of a Cycle Having a Minimum Signal Value

The extracted signals in Example 1 (see FIGS. 8A to 8D, left column) were analyzed for selecting a cycle having a minimum signal value. Then, the signal value(s) from a first cycle to a cycle immediately before the selected cycle was regarded as a target-unrelated signal region, and the signal value(s) from the selected cycle to an end cycle was regarded as a target-related signal region.

<2-2> Adjustment of the Target-Unrelated Signal Region

For each extracted signal, the signal value(s) from the first cycle to the cycle immediately before the selected cycle (target-unrelated signal region) was adjusted not to affect the determination of the presence of NG target. Specifically, the signal value(s) was adjusted to be equal to the signal value at the selected cycle (a cycle having the minimum value).

<2-3> Shifting of the Entire Signal Values

The entire signal values, comprising the adjusted signal value(s) from the first cycle to the cycle immediately before the selected cycle and the unadjusted signal value(s) from the selected cycle to the end cycle, were shifted upward such that the selected cycle has a signal value of zero. The obtained signals were provided as analytical signals for determination of the presence of NG target.

The analytical signals for NG target obtained by the above steps were shown on the right column of FIGS. 8A to 8D.

Figure 8A:
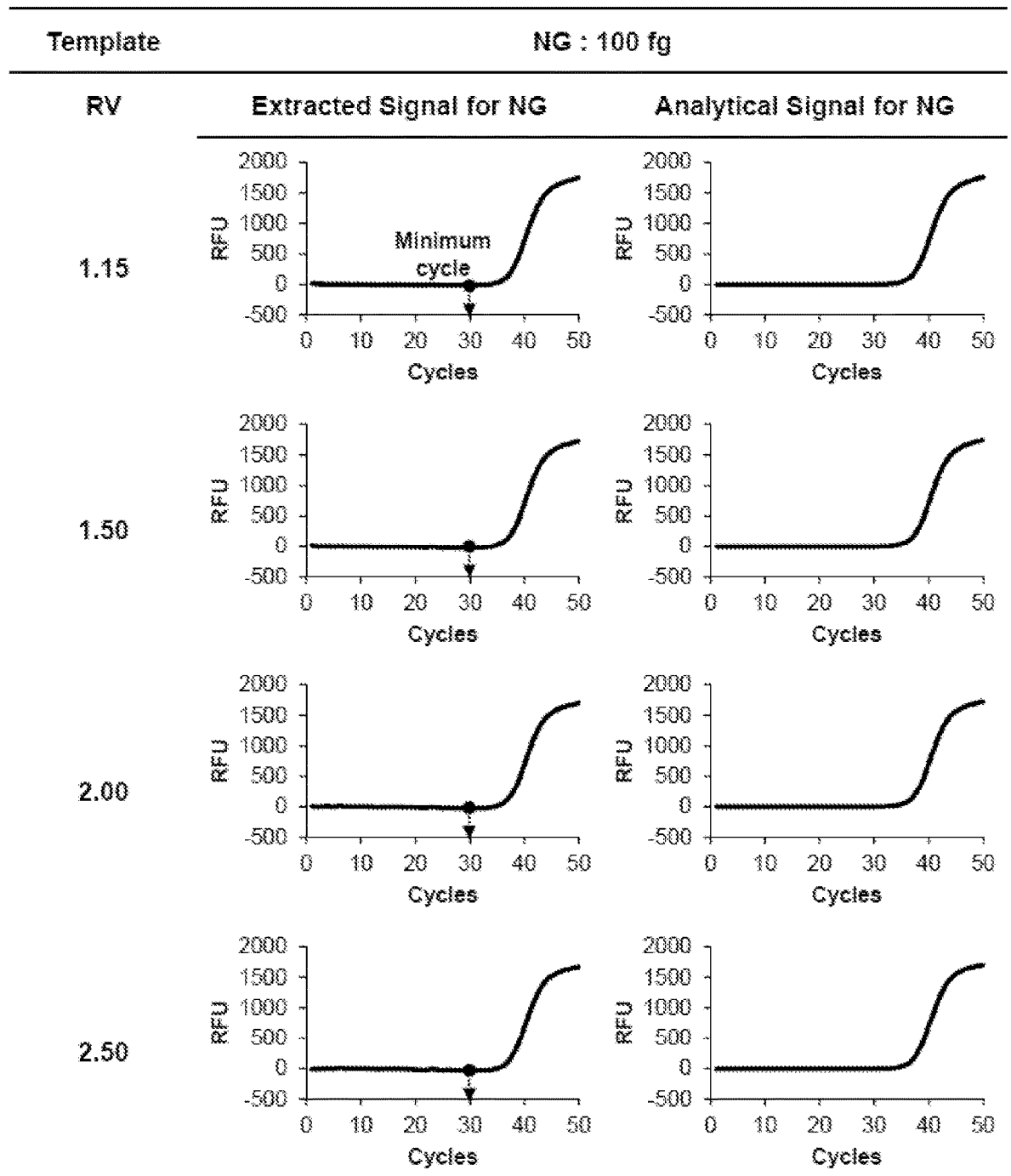
FIGS. 8A, 8B, 8C and 8D represent extracted signals for NG target obtained by using various reference values (1.15, 1.50, 2.00, or 2.50) and Equation I-1 from the signals in FIG. 5 (left column); and analytical signals for NG target obtained from the extracted signals in accordance with an embodiment of this invention 200 (right column). A minimum cycle (a cycle having a minimum signal value) in each extracted signal is indicated by an arrow.
Figure 8B:
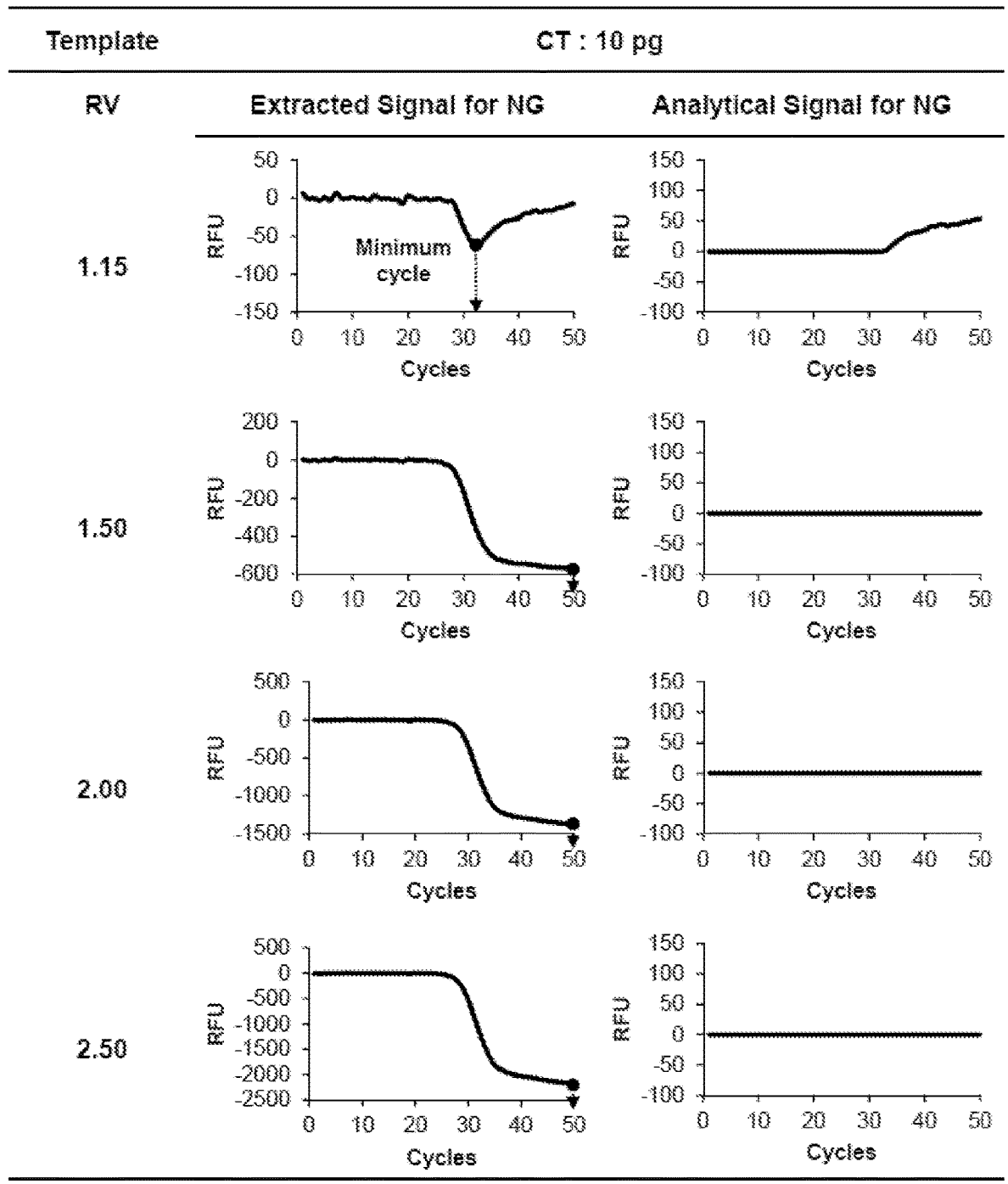

As shown in FIG. 8B, it was found that the erroneously extracted signals (left column) were amended into the correctly extracted signals (right column) by the method of the present invention, for the sample containing 10 pg of CT only.

Figure 8C:
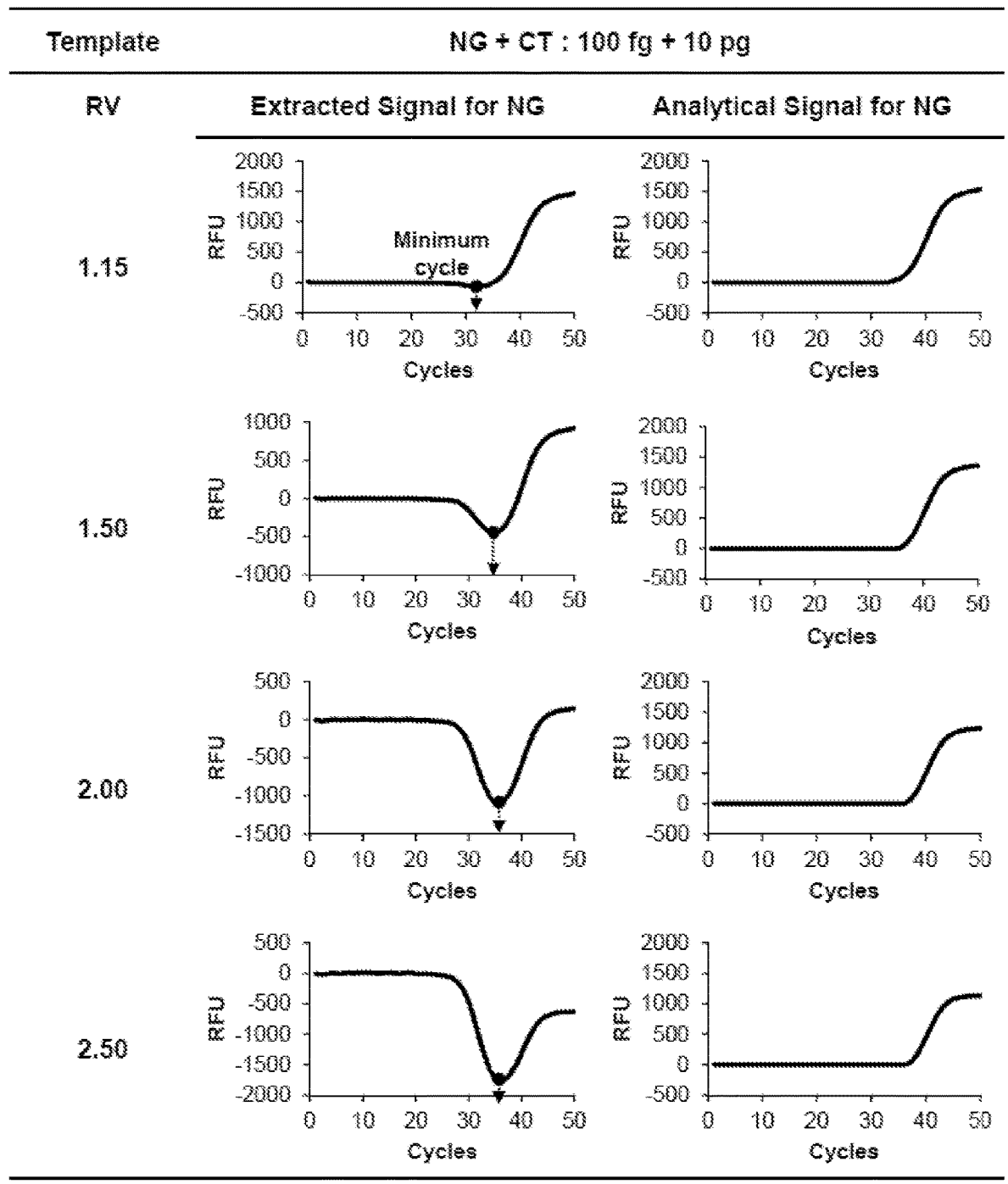
Figure 8D:
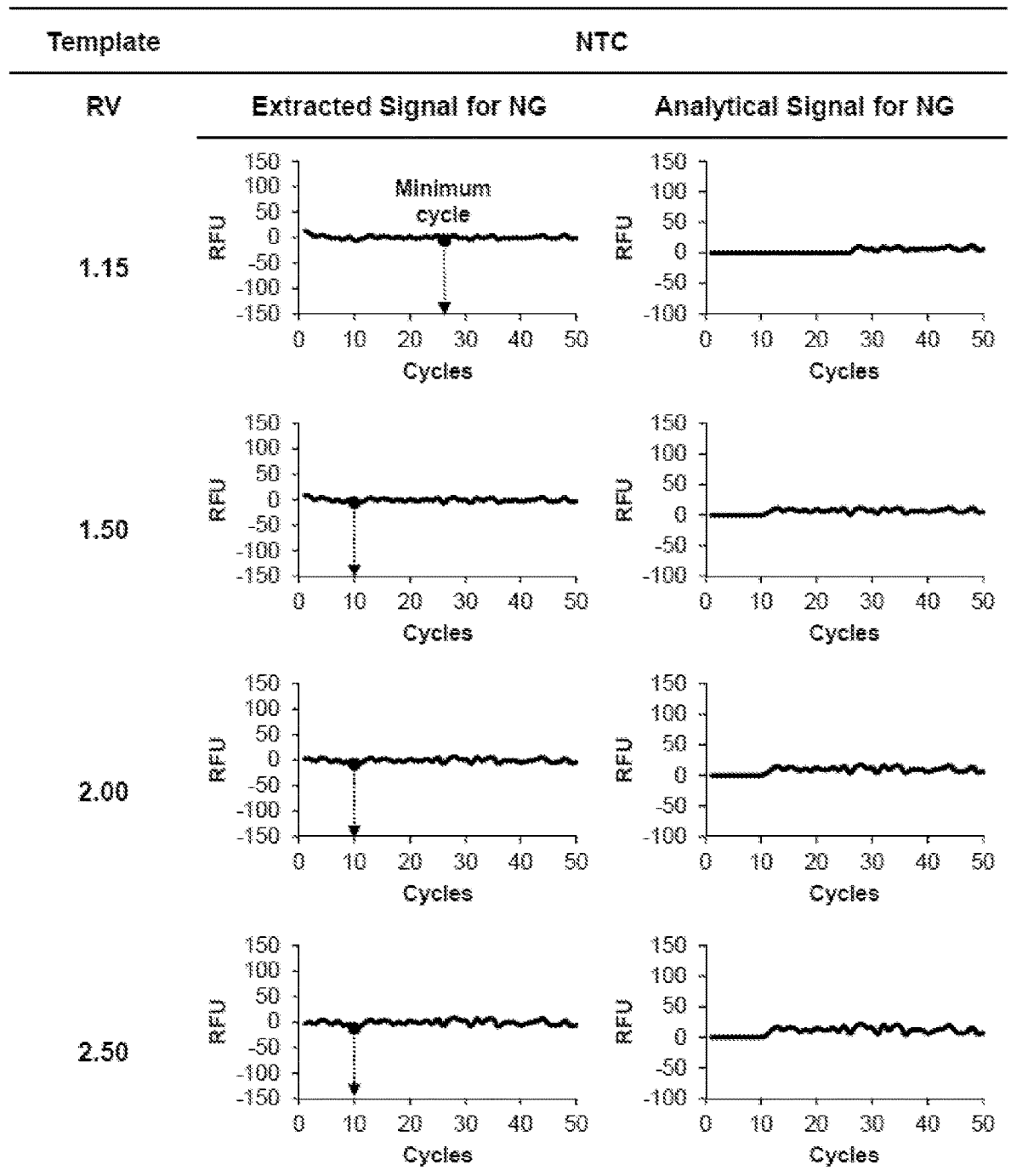

Further, as shown in FIG. 8C, it was found that the erroneously extracted signals (left column) were amended into the correctly extracted signals (right column) by the method of the present invention, for the sample containing 100 fg of NG and 10 pg of CT.

<2-4> Determination of the Presence of the Target Nucleic Acid Sequence

Using the analytical signals provided in the step 3, the presence and the amount of the target nucleic acid sequence were determined. For this purpose, a threshold of RFU 100 was used.

The results are summarized in Table 2 below.

TABLE 2

| NG | CT | RV | Extracted Signal | | Analytical Signal | |
|----|----|----|----|----|----|----|
| | | | Presence | Ct value | Presence | Ct value |
| 100 fg | — | 1.15 | Positive | 36.43 | Positive | 36.21 |
| 100 fg | — | 1.50 | Positive | 36.55 | Positive | 36.26 |
| 100 fg | — | 2.00 | Positive | 36.72 | Positive | 36.32 |
| 100 fg | — | 2.50 | Positive | 36.89 | Positive | 36.39 |
| — | 10 pg | 1.15 | Negative | N.D | Negative | N.D |
| — | 10 pg | 1.50 | Negative | N.D | Negative | N.D |
| — | 10 pg | 2.00 | Negative | N.D | Negative | N.D |
| — | 10 pg | 2.50 | Negative | N.D | Negative | N.D |
| 100 fg | 10 pg | 1.15 | Positive | 36.56 | Positive | 35.72 |
| 100 fg | 10 pg | 1.50 | Positive | 39.85 | Positive | 36.98 |
| 100 fg | 10 pg | 2.00 | Positive | 46.35 | Positive | 37.47 |
| 100 fg | 10 pg | 2.50 | Negative | N.D | Positive | 37.79 |
| — | — | 1.15 | Negative | N.D | Negative | N.D |
| — | — | 1.50 | Negative | N.D | Negative | N.D |
| — | — | 2.00 | Negative | N.D | Negative | N.D |
| — | — | 2.50 | Negative | N.D | Negative | N.D |

As shown in Table 2, it was found that a false negative error and some Ct values were amended for the sample containing 10 pg of CT only and the sample containing 100 fg of NG and 10 pg of CT.

Example 3: Signal Detection and Extraction Based on MuDT2 Technology

According to an embodiment of MuDT2 technology (see WO 2016/093619), the two signal-generating means generate signals at the relatively high detection temperature and the relatively low detection temperature. The processing of the signal values is performed to extract the signal for the second target nucleic acid sequence by the first reference value from the signal at the relatively low detection temperature or the signal at the relatively high detection temperature. Likewise, the processing of the signal values is performed to extract the signal for the first target nucleic acid sequence by the second reference value from the signal at the relatively low detection temperature or the signal at the relatively high detection temperature.

<3-1> Preparation of Templates and Oligonucleotides

The TaqMan method was used as a real-time PCR approach for detecting signals in a real-time manner at different detection temperatures.

Taq DNA polymerase having a 5' nuclease activity was used for the extension of upstream primers and downstream primers and the cleavage of TaqMan probes. Genomic DNA of *Neisseria gonorrhoeae* (NG) and genomic DNA of *Chlamydia trachomatis* (CT) were used as target nucleic acid sequences.

Where a target nucleic acid is present in the TaqMan real-time PCR, a TaqMan probe is cleaved and a labeled fragment is released. The release of the labeled fragment provides a signal and an amplification curve can be obtained by measuring the signal from the labeled fragment.

A TaqMan probe for NG was labeled with a fluorescent reporter molecule (Quasar 670) at its 5'-end and a quencher molecule at its 3'-end (SEQ ID NO: 9) and a TaqMan probe for CT with a fluorescent reporter molecule (Quasar 670) at its 5'-end and a quencher molecule at its internal site (BHQ-2) (SEQ ID NO: 12).

In this Example, a signal for NG and a signal for CT are both detected at 60° C. and 72° C. The TaqMan probes used for the two targets provide different relationships in a signal change between the two detection temperatures (i.e., different reference values). In particular, the TaqMan probes were designed in this Example such that the difference in signals at 60° C. and 72° C. for CT was higher than that for NG.

The sequences of upstream primers, downstream primers, and TaqMan probes used in this Example are described in Table 3.

TABLE 3

| Name | Type | Sequence (5' → 3') | SEQ ID |
|------|------|--------------------|--------|
| NG_F | Primer | TACGCCTGCTACTTTCAC GCTIIIIIGTAATCAGAT G | SEQ ID NO: 1 |
| NG_R | Primer | CAATGGATCGGTATCACT CGCIIIIICGAGCAAGAA C | SEQ ID NO: 2 |
| NG_P | TaqMan Probe | [Quasar 670]TGCCCC TCATTGGCGTGTTTCG [BHQ-2] | SEQ ID NO: 9 |

TABLE 3-continued

| Name | Type | Sequence (5' → 3') | SEQ ID |
|---|---|---|---|
| CT2_F | Primer | TCCGAATGGATAAAGCGT GACIIIIIATGAACTCAC | SEQ ID NO: 10 |
| CT2_R | Primer | AACAATGAATCCTGAGCA AAGGIIIIICGTTAGAGT C | SEQ ID NO: 11 |
| CT2_P | TaqMan Probe | [Quasar 670]CATTGT AAAGA[T(BHQ-2)]ATG GTCTGCTTCGACCG[C3 spacer] | SEQ ID NO: 12 |

I: Deoxyinosine
BHQ: Quencher (Black Hole Quencher)

<3-2> Real-Time PCR and Signal Detection at Different Temperatures

The real-time PCR in accordance with the TaqMan method was conducted in the final volume of 20 µl containing a target nucleic acid (10 pg of NG genomic DNA, 1 pg of CT genomic DNA, a mixture of 10 pg of NG genomic DNA and 1 pg of CT genomic DNA), 5 pmole of upstream primer (SEQ ID NO:1), 10 pmole of downstream primer (SEQ ID NO:2) and 1.5 pmole of TaqMan probe (SEQ ID NO:9) for NG target amplification, 5 pmole of upstream primer (SEQ ID NO:10), 10 pmole of downstream primer (SEQ ID NO:11) and 3 pmole of TaqMan probe (SEQ ID NO:12) for CT target amplification, and 5 µl of 4× Master Mix (final conc., 200 pM dNTPs, 2 mM $MgCl_2$, 2 U of Taq DNA polymerase)(Enzynomics, Korea). The tubes containing the reaction mixture were placed on the real-time thermocycler (CFX96 Real-time Cycler, Bio-Rad) for 5 min at 50° C., denatured for 15 min at 95° C. and subjected to 50 cycles of 30 sec at 95° C., 60 sec at 60° C., 30 sec at 72° C. Detection of signals was performed at 60° C. and 72° C. at each cycle. The results are represented in FIG. 9.

Figure 9:
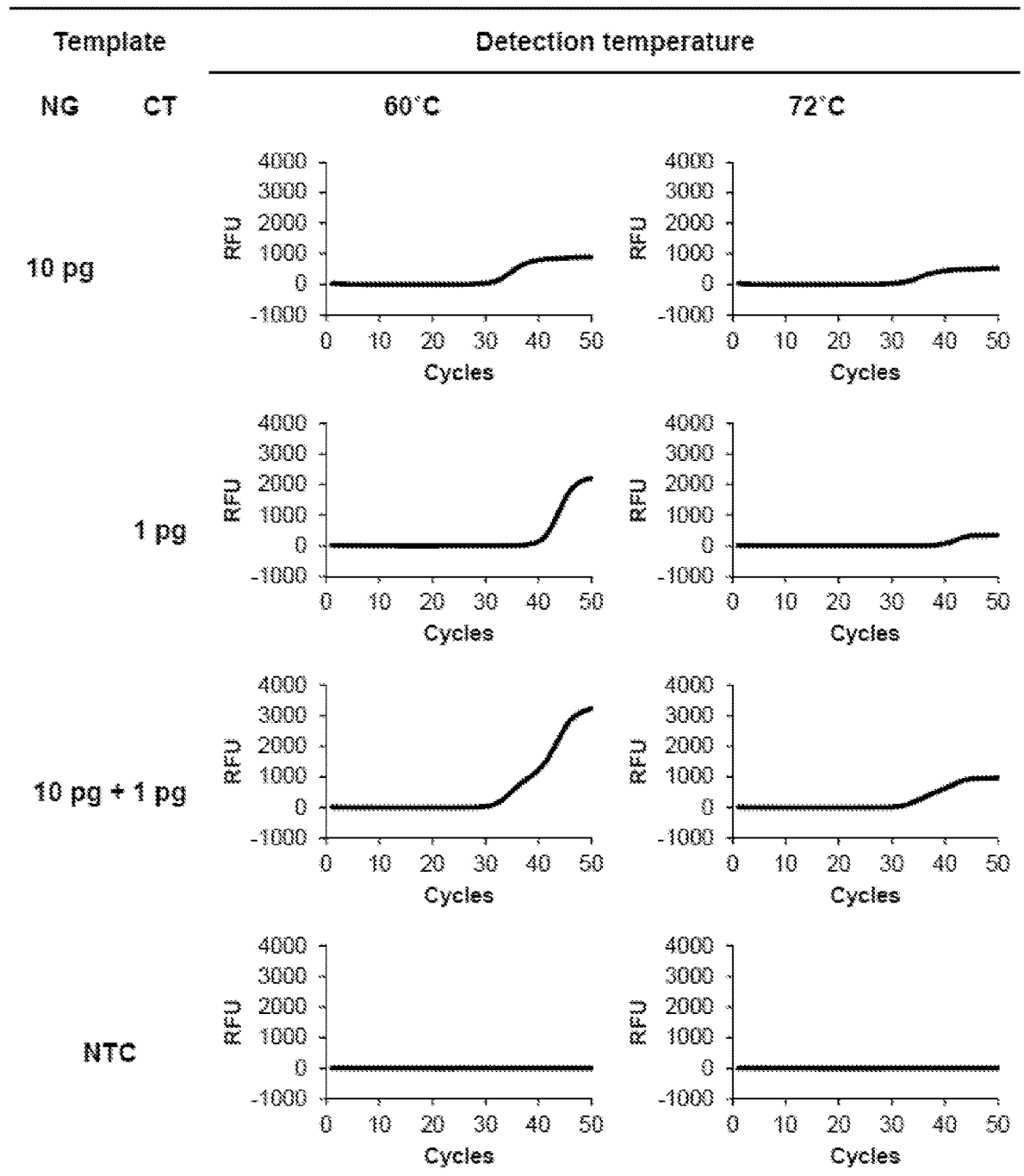
FIG. 9 represents signals detected at different detection temperatures of 60° C. and 72° C. in accordance with MuDT2 Technology (see WO 2016/093619) using a TaqMan real-time PCR method, for samples containing 10 pg of genomic DNA of *Neisseria gonorrhoeae* (NG), 1 pg of genomic DNA of *Chlamydia trachomatis* (CT), a mixture of 10 pg of NG and 1 pg of CT, and NTC (no target control).

As shown in FIG. 9, signals were detected both at 60° C. and 72° C. in the presence of NG, CT, or NG+CT targets and not detected in the absence of targets (NTC).

<3-3> Extraction of Signal for a Target Nucleic Acid Sequence

As represented in FIG. 9, signals for each target cannot be directly taken from signals detected at 60° C. or 72° C. Therefore, signals for the other target have to be removed from signals at each detection temperature for extraction of signals for each target.

Signals for each target can be extracted by using a reference value representing a relationship of change in signals at 72° C. and 60° C. for each target. In this Example, signals were extracted in accordance with the mathematical Equation I-1 and mathematical Equation I-4:

Extracted signal for the second target nucleic acid sequence=[signal at the relatively low detection temperature]−[(signal at the relatively high detection temperature)×(first reference value)];  <Equation I-1> wherein, the second target nucleic acid sequence is CT target; and the first reference value is a ratio of the signal provided by the first signal-generating means at the relatively low detection temperature to the signal provided by the first signal-generating means at the relatively high detection temperature.

Extracted signal for the first target nucleic acid sequence=[signal at the relatively high detection temperature]−[(signal at the relatively low detection temperature)÷(second reference value)];  <Equation I-4> wherein, the first target nucleic acid sequence is NG target; and the second reference value is a ratio of the signal provided by the second signal-generating means at the relatively low detection temperature to the signal provided by the second signal-generating means at the relatively high detection temperature.

The extracted signal for each target can be plotted.

The reference value for each target may be calculated in accordance with the mathematical Equations II-1 and II-2:

reference value for CT target=[signal at 60° C. for a control sample containing only CT target]÷[signal at 72° C. for a control sample containing only CT target]  <Equation II-1> reference value for NG target=[signal at 60° C. for a control sample containing only NG target]÷[signal at 72° C. for a control sample containing only NG target]  <Equation II-2>

As shown in FIGS. 10A to 10D, the signal for NG target was extracted from signal at 72° C. by using a reference value for CT target. The reference value for CT was predetermined as "6.50, 6.00, 5.50, or 5.00". The application of the reference value for CT target (5.50 or 5.00) generated erroneous signals due to removal of signals larger than signals originated from CT target in a sample containing 1 pg of CT target (see FIG. 10B). The erroneous signal addresses that the reference value is not suitable.

As shown in FIGS. 11A to 11D, the signal for CT target was extracted from signal at 60° C. by using a reference value for NG target. The reference value for NG was predetermined as "1.80, 2.50, 3.00, or 3.50". The application of the reference value for NG target (2.50, 3.00, or 3.50) generated erroneous signals due to removal of signals larger than signals originated from NG target (see FIGS. 11A and 11C). The erroneous signal addresses that the reference value is not suitable.

These results demonstrate that when a single reference value is applied to all reactions for signal extraction for a target nucleic acid sequence, erroneous signals are generated due to unsuitability of the reference value to certain samples.

Example 4: Providing an Analytical Signal for Determination of the Presence of a Target Nucleic Acid Sequence Based on MuDT2 Technology In a similar manner to Example 2, the extracted signals in Example 3 were analyzed for selecting a cycle having a minimum signal value. Since suitably extracted signal is expected to exhibit an increasing signal pattern, a cycle having a minimum signal value was selected in this Example. Afterwards, the signal value(s) from the first cycle to the cycle immediately before the selected cycle (target-unrelated signal region) was adjusted to be equal to the signal value at the selected cycle (a cycle having the minimum value). Then, the entire signal values, comprising the adjusted signal value(s) from the first cycle to the cycle immediately before the selected cycle and the unadjusted signal value(s) from the selected cycle to the end cycle, were shifted upward such that the selected cycle has a signal value of zero. The obtained signals were provided as analytical signals for determination of the presence of NG target or CT target.

The analytical signals for NG target obtained by the above steps were shown on the right column of FIGS. 10A to 10D. Also, the analytical signals for CT target obtained by the above steps were shown on the right column of FIGS. 11A to 11D.

Figure 10A:
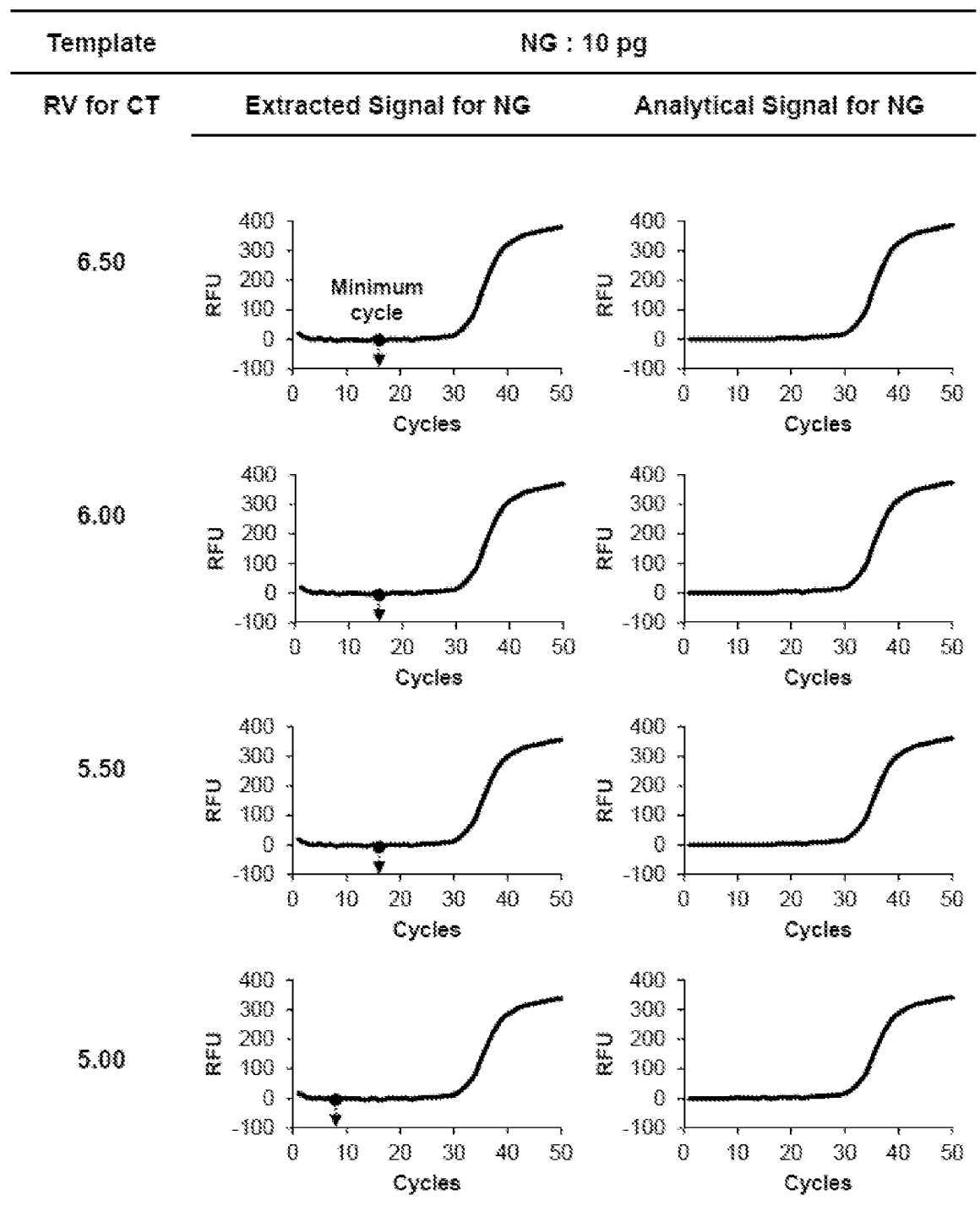
FIGS. 10A, 10B, 10C and 10D represent extracted signals for NG target obtained by using various reference values (6.50, 6.00, 5.50 or 5.00) and Equation I-4 from the signals in FIG. 9 (left column); and analytical signals for NG target obtained from the extracted signals in accordance with an embodiment of this invention 200 (right column). A minimum cycle in each extracted signal is indicated by an arrow.
Figure 10B:
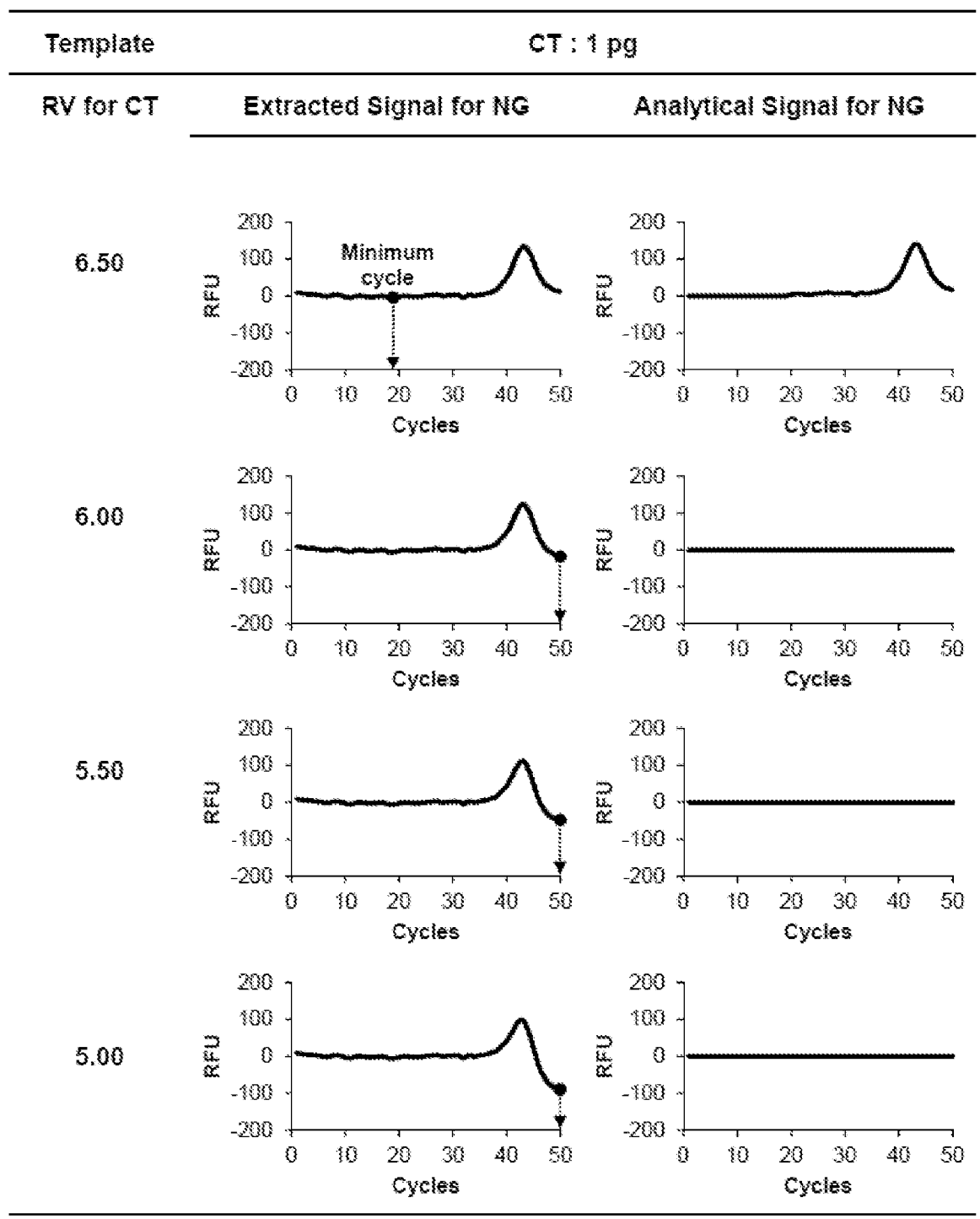
Figure 10C:
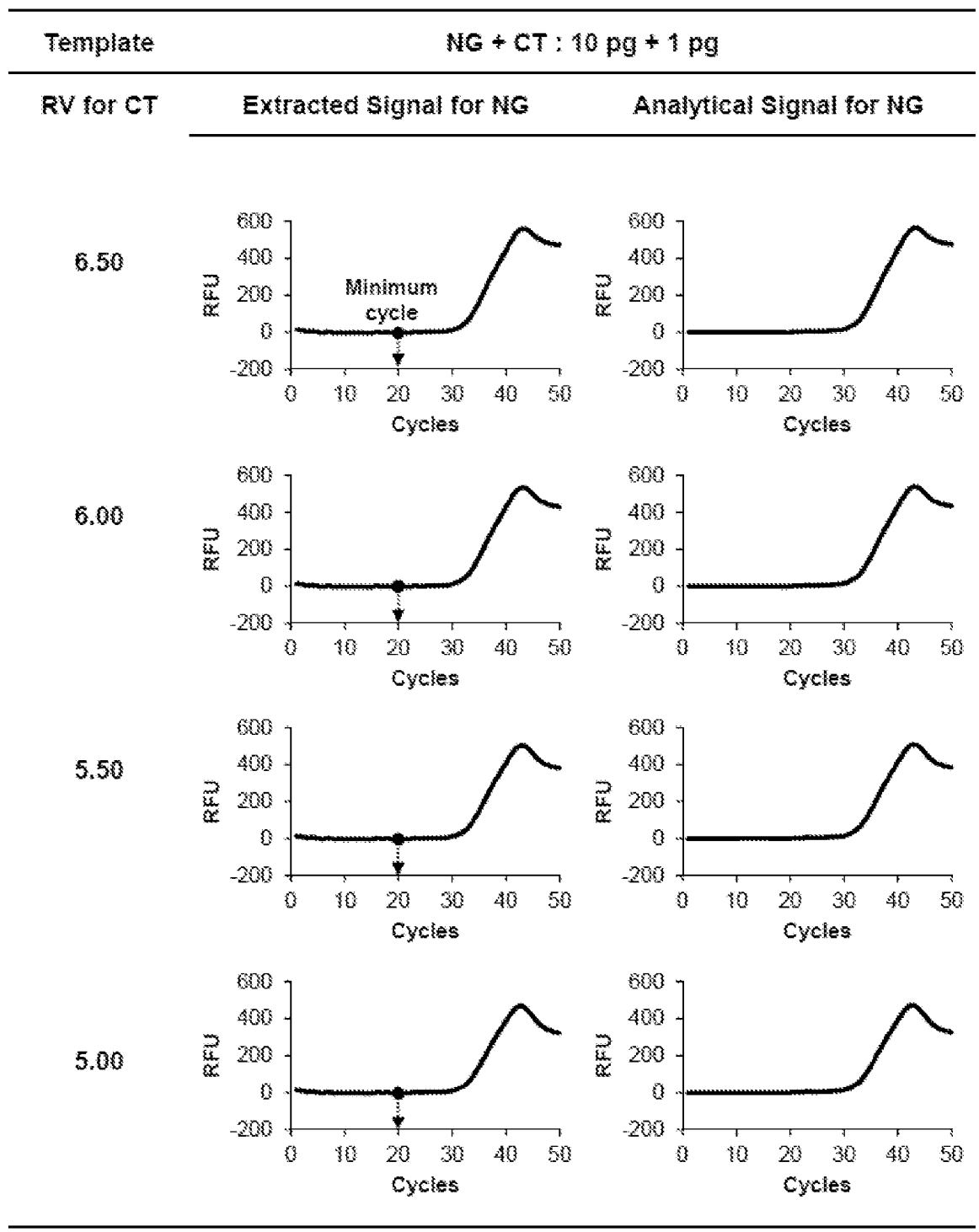
Figure 10D:
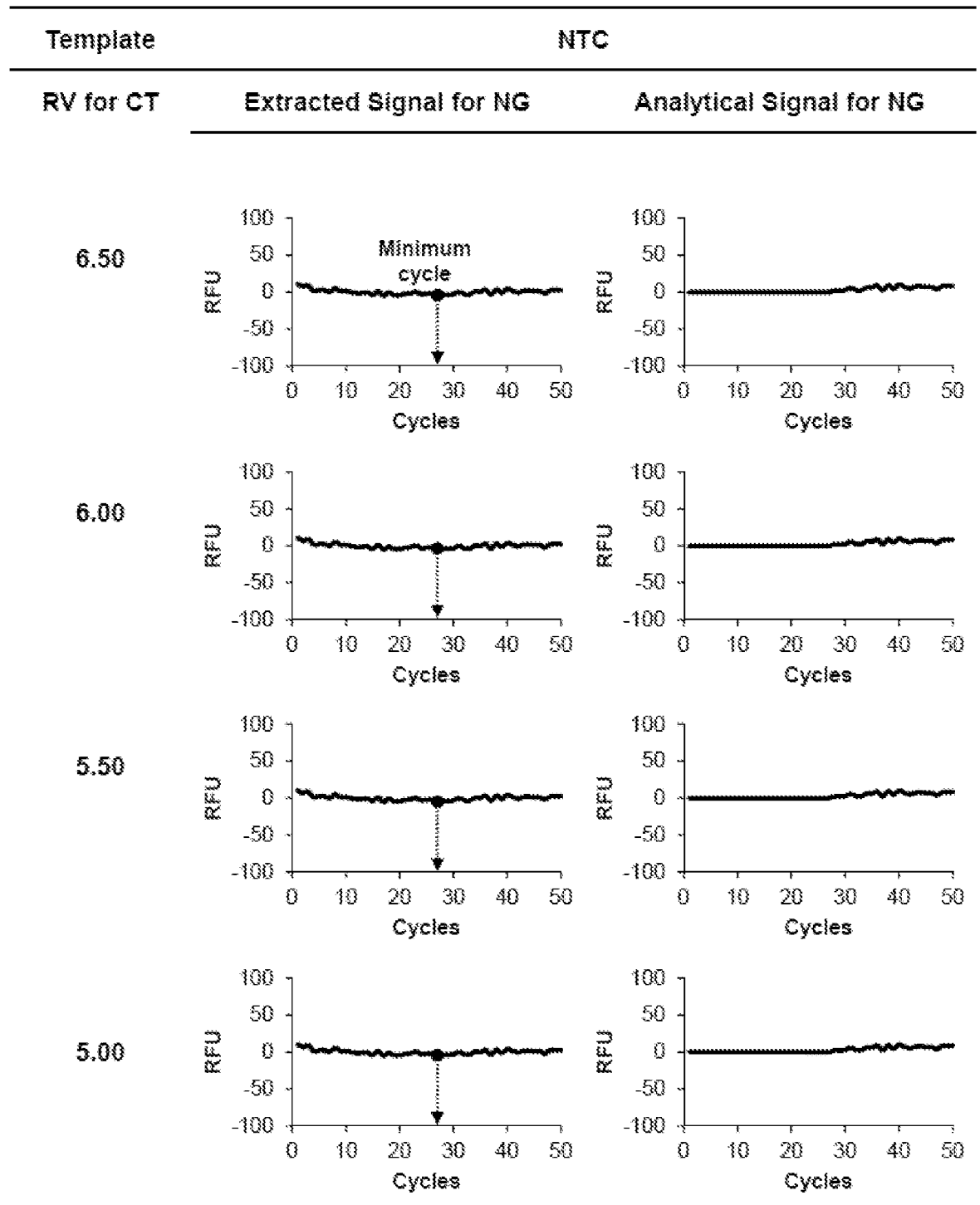

As shown in FIG. 10B, it was found that the erroneously extracted signals (left column) were amended into the correctly extracted signals (right column) by the method of the present invention, for the sample containing 1 pg of CT only.

Figure 11A:
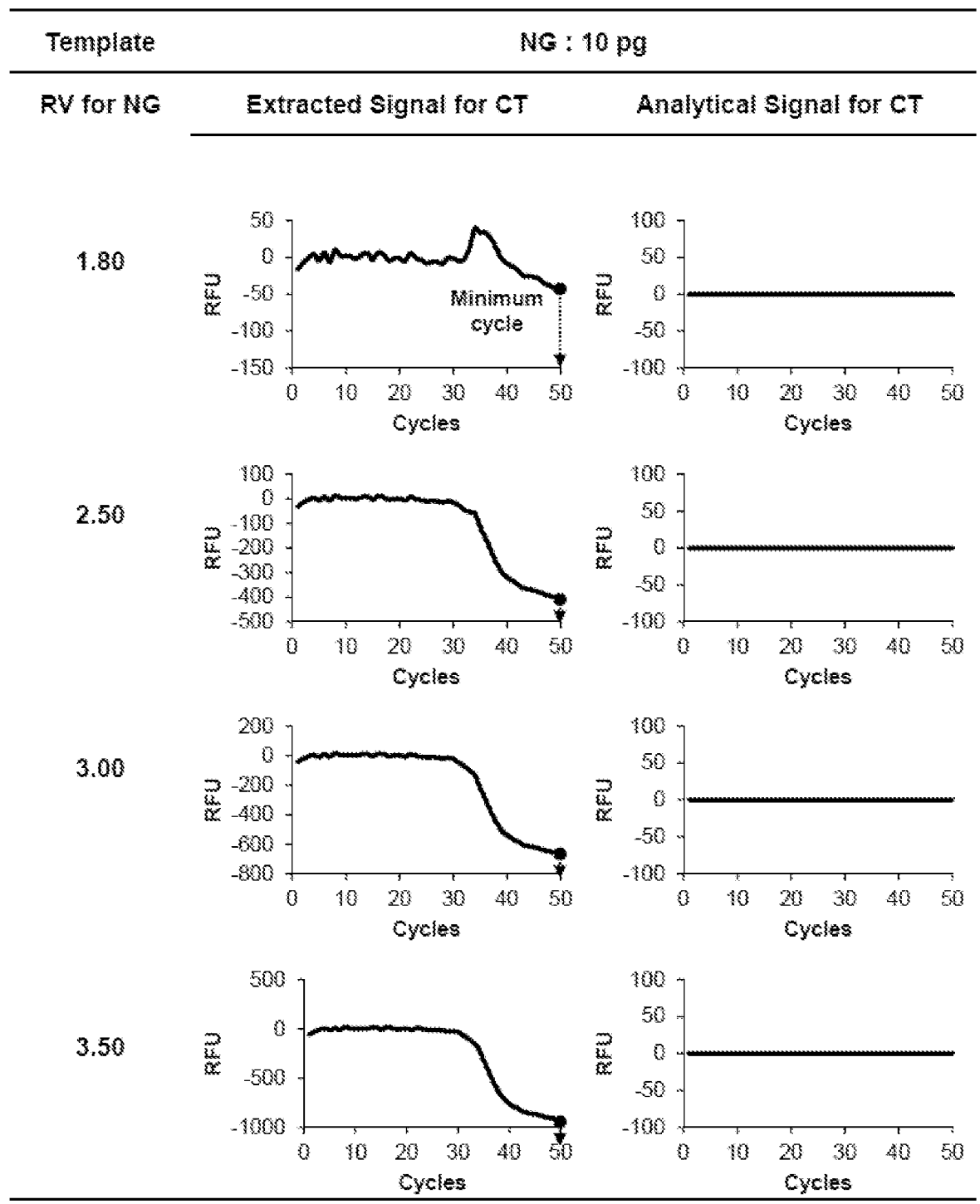
FIGS. 11A, 11B, 11C and 11D represent extracted signals for CT target obtained by using various reference values (1.80, 2.50, 3.00 or 3.50) and Equation I-1 from the signals in FIG. 9 (left column); and analytical signals for CT target obtained from the extracted signals in accordance with an embodiment of this invention 200 (right column). A minimum cycle in each extracted signal is indicated by an arrow.
Figure 11B:
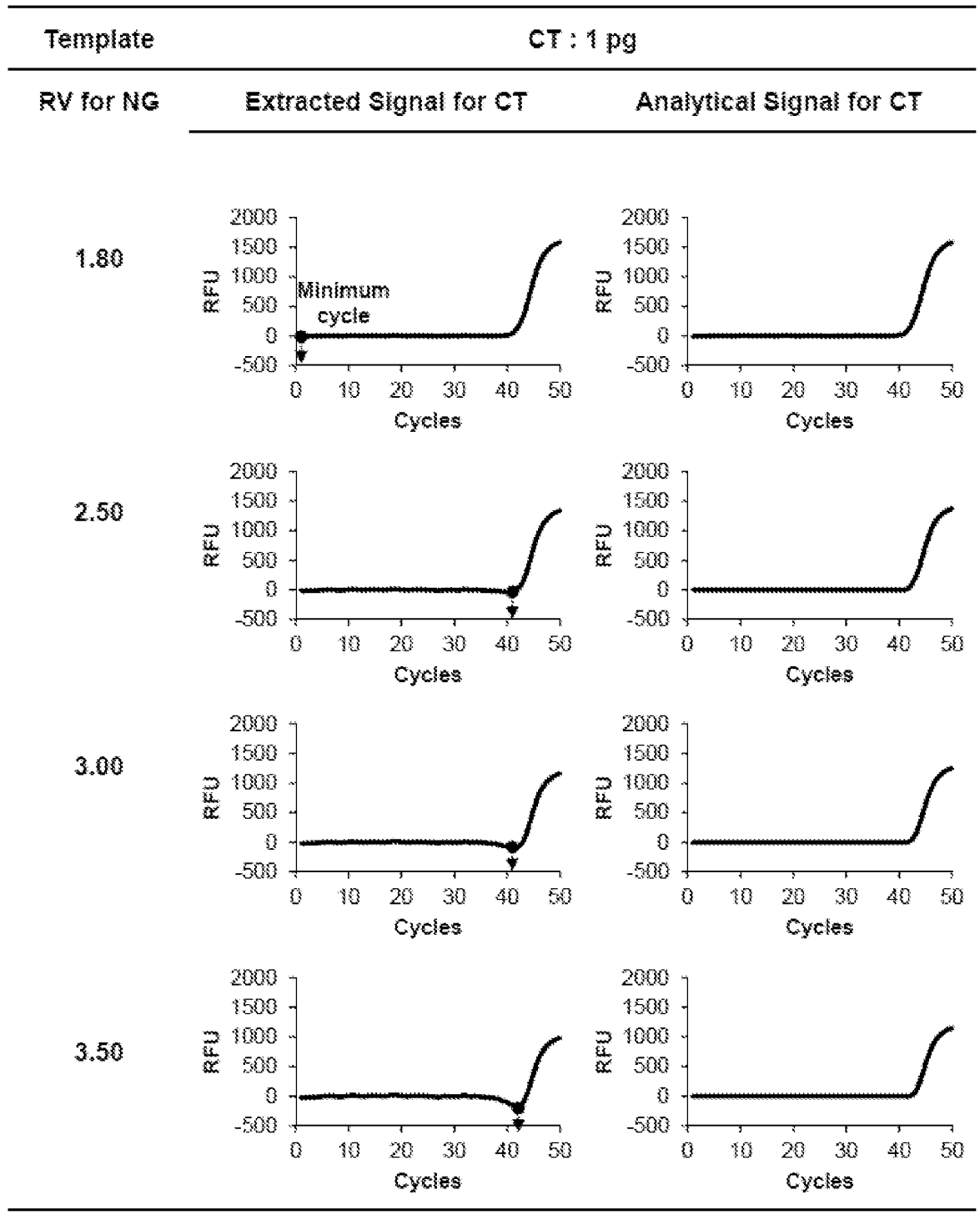
Figure 11C:
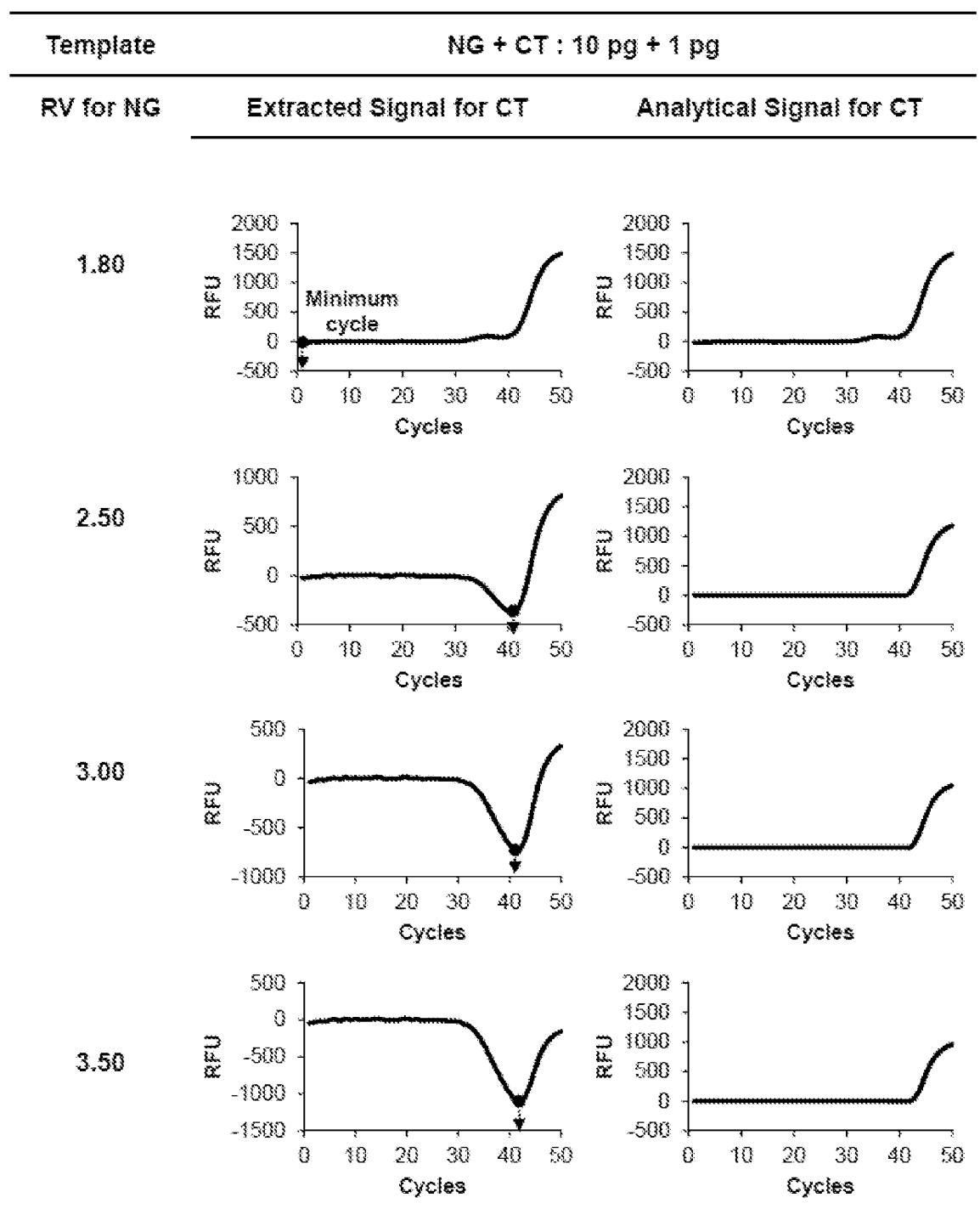
Figure 11D:
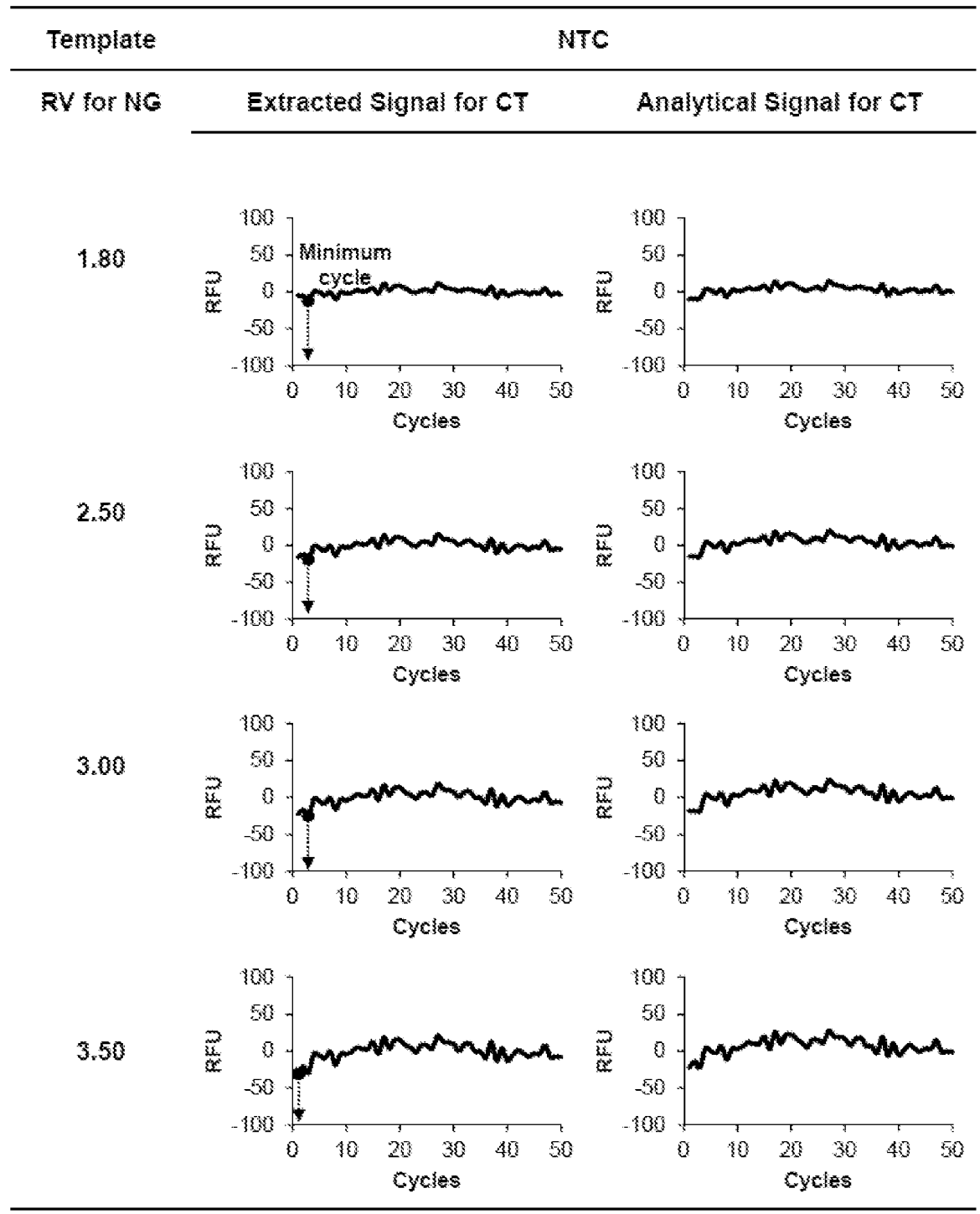

As shown in FIG. 11A, it was found that the erroneously extracted signals (left column) were amended into the correctly extracted signals (right column) by the method of the present invention, for the sample containing 10 fg of NG only and the sample containing 10 pg of NG and 1 pg of CT.

Further, using the analytical signals, the presence and the amount of the target nucleic acid sequence were determined. For this purpose, thresholds of 200 and 150 were used for CT and NG targets, respectively.

The results are summarized in Tables 4 and 5 below.

TABLE 4

|  |  |  | Extracted Signal | | Analytical Signal | |
| --- | --- | --- | --- | --- | --- | --- |
| NG | CT | RV | Presence | Ct value | Presence | Ct value |
| 10 pg | — | 6.50 | Positive | 35.04 | Positive | 34.94 |
| 10 pg | — | 6.00 | Positive | 35.16 | Positive | 35.05 |
| 10 pg | — | 5.50 | Positive | 35.30 | Positive | 35.19 |
| 10 pg | — | 5.00 | Positive | 35.50 | Positive | 35.41 |
| — | 1 pg | 6.50 | Negative | N.D | Negative | N.D |
| — | 1 pg | 6.00 | Negative | N.D | Negative | N.D |
| — | 1 pg | 5.50 | Negative | N.D | Negative | N.D |
| — | 1 pg | 5.00 | Negative | N.D | Negative | N.D |
| 10 pg | 1 pg | 6.50 | Positive | 34.74 | Positive | 34.65 |
| 10 pg | 1 pg | 6.00 | Positive | 34.87 | Positive | 34.77 |
| 10 pg | 1 pg | 5.50 | Positive | 35.02 | Positive | 34.93 |
| 10 pg | 1 pg | 5.00 | Positive | 35.20 | Positive | 35.12 |
| — | — | 6.50 | Negative | N.D | Negative | N.D |
| — | — | 6.00 | Negative | N.D | Negative | N.D |
| — | — | 5.50 | Negative | N.D | Negative | N.D |
| — | — | 5.00 | Negative | N.D | Negative | N.D |

TABLE 5

|  |  |  | Extracted Signal | | Analytical Signal | |
| --- | --- | --- | --- | --- | --- | --- |
| NG | CT | RV | Presence | Ct value | Presence | Ct value |
| 10 pg | — | 1.80 | Negative | N.D | Negative | N.D |
| 10 pg | — | 2.50 | Negative | N.D | Negative | N.D |
| 10 pg | — | 3.00 | Negative | N.D | Negative | N.D |
| 10 pg | — | 3.50 | Negative | N.D | Negative | N.D |
| — | 1 pg | 1.80 | Positive | 42.29 | Positive | 42.29 |
| — | 1 pg | 2.50 | Positive | 43.20 | Positive | 43.06 |
| — | 1 pg | 3.00 | Positive | 43.77 | Positive | 43.37 |
| — | 1 pg | 3.50 | Positive | 44.36 | Positive | 43.65 |
| 10 pg | 1 pg | 1.80 | Positive | 41.67 | Positive | 41.69 |
| 10 pg | 1 pg | 2.50 | Positive | 44.68 | Positive | 43.07 |
| 10 pg | 1 pg | 3.00 | Positive | 47.66 | Positive | 43.46 |
| 10 pg | 1 pg | 3.50 | Negative | N.D | Positive | 43.75 |
| — | — | 1.80 | Negative | N.D | Negative | N.D |
| — | — | 2.50 | Negative | N.D | Negative | N.D |
| — | — | 3.00 | Negative | N.D | Negative | N.D |
| — | — | 3.50 | Negative | N.D | Negative | N.D |

As shown in Table 4, it was found that some Ct values were amended, for the sample containing 10 pg of NG only and the sample containing 10 pg of NG and 1 pg of CT.

Also, as shown in Table 5, it was found that some Ct values were amended for the sample containing 1 pg of CT only, and, a false negative error and some Ct values were also amended for the sample containing 10 pg of NG and 1 pg of CT.

Example 5: Applicability of the Method of the Present Invention to Signals Extracted in a Different Way It was examined whether the method of present invention can be applied to the signals for the second target nucleic acid sequence (i.e., CT target) extracted using Equation I-2 instead of those extracted using Equation I-1 in Example 3.

For this purpose, both signals detected at 60° C. and 72° C. for a sample containing a mixture of 10 pg of NG and 1 pg of CT (see 3rd row in FIG. 9) were subjected to signal extraction for CT target. For signal extraction of CT target, the following mathematical Equation I-2 was used:

Extracted signal for the second target nucleic acid sequence=[signal at the relatively high detection temperature obtained in the step (a)]−[(signal at the relatively low detection temperature obtained in the step (a))÷(first reference value)];  <Equation I-2> wherein, the second target nucleic acid sequence is CT target; and the first reference value is a ratio of the signal provided by the first signal-generating means at the relatively low detection temperature to the signal provided by the first signal-generating means at the relatively high detection temperature.

The first reference values, 1.80, 2.50, 3.00 and 3.50, were used.

Figure 12:
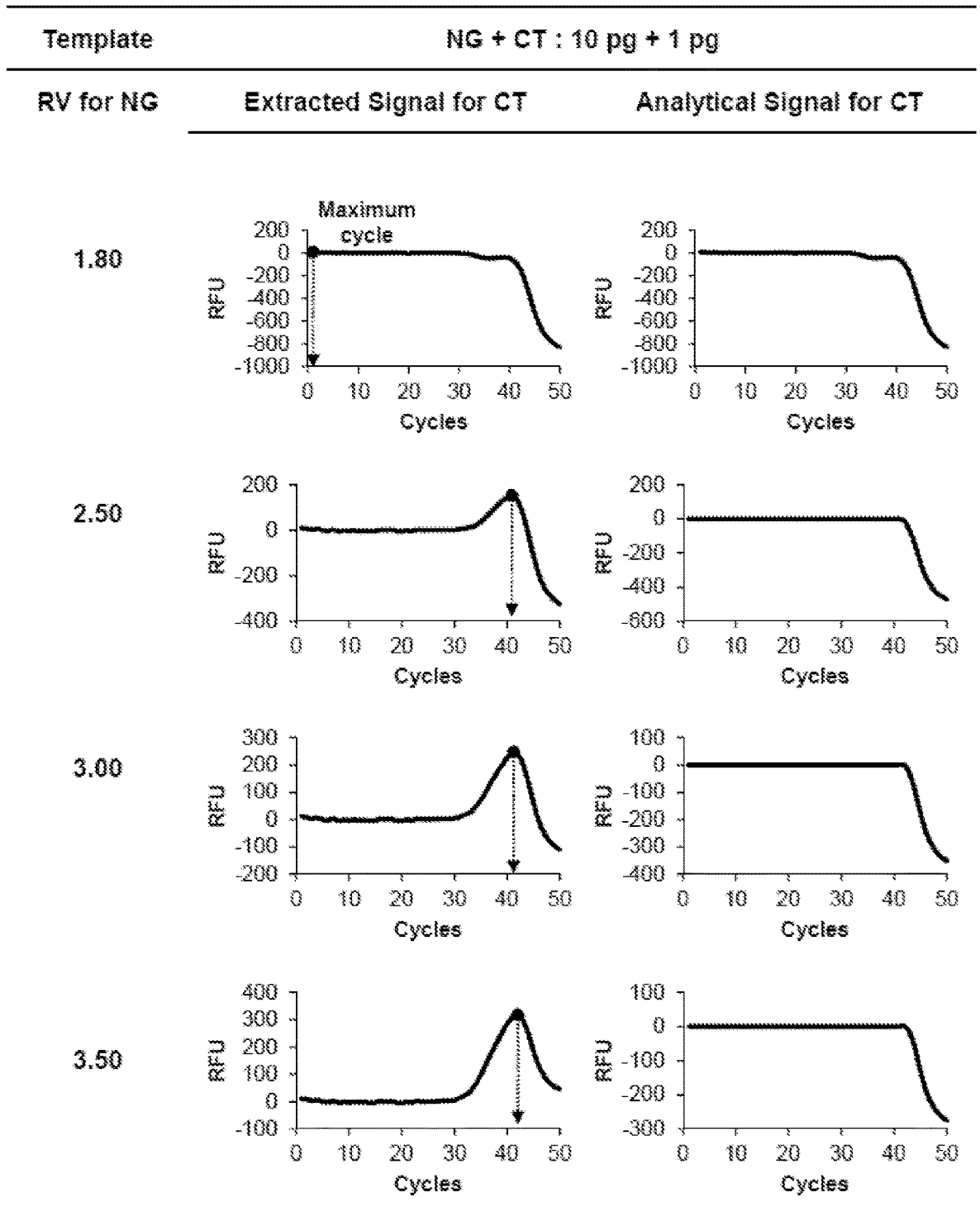
FIG. 12 represents extracted signals for CT target obtained by using various reference values (1.80, 2.50, 3.00 or 3.50) and Equation I-2 from the signals in FIG. 9 (left column); and analytical signals for CT target obtained from the extracted signals in accordance with an embodiment of this invention 200 (right column), particularly for a sample containing a mixture of 10 pg of NG and 1 pg of CT. A maximum cycle (a cycle having a maximum signal value) in each extracted signal is indicated by an arrow.

The extracted signals for CT target were shown in the left column of FIG. 12.

If the reference value used is suitable, the signal extracted using Equation I-2 will show a decreasing pattern in the presence of the target or substantially zero (o) in the absence of the target. Thus, a signal that deviates from such predicted signal pattern, for example a signal having a signal value(s) significantly higher than RFU 0 corresponds to an erroneously extracted signal.

As shown in the left column of FIG. 12, the application of the reference value for NG target (2.50, 3.00, or 3.50) generated erroneous signals significantly higher than RFU 0.

In a similar manner to Example 4, the extracted signals were analyzed for selecting a cycle having a maximum signal value. Since suitably extracted signal is expected to exhibit a decreasing signal pattern, a cycle having a maximum signal value was selected in this Example. Afterwards, the signal value(s) from the first cycle to the cycle immediately before the selected cycle (target-unrelated signal region) was adjusted to be equal to the signal value at the selected cycle (a cycle having the maximum value). Then, the entire signal values, comprising the adjusted signal value(s) from the first cycle to the cycle immediately before the selected cycle and the unadjusted signal value(s) from the selected cycle to the end cycle, were shifted downward such that the selected cycle has a signal value of zero. The obtained signals were provided as analytical signals for determination of the presence of CT target.

The analytical signals for CT target obtained by the above steps were shown on the right column of FIG. 12.

As shown in FIG. 12, it was found that the erroneously extracted signals (left column) were amended into the correctly extracted signals (right column) by the method of the present invention.

These results urge us to reason that the inventive method permits to detect target nucleic acid sequences in more accurate manner by using the particular signal region as an analytical signal.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for providing an analytical signal for determination of the presence of a target nucleic acid sequence in a sample, comprising:
   (a) incubating the sample with a first signal-generating means capable of generating a signal for a first target nucleic acid sequence and a second signal-generating means capable of generating a signal for a second target nucleic acid sequence in a single reaction vessel and detecting signals at a relatively high detection temperature and a relatively low detection temperature by a single type of detector; wherein the incubation is performed by a signal-generating process; wherein the detection is performed at one or more cycles of the signal-generating process to obtain a signal value at each of the one or more cycles; wherein the two signals to be generated by the two signal-generating means are not differentiated by the single type of detector;
   (b) processing the signal values obtained in the step (a) by using a second reference value to extract the signal for the first target nucleic acid sequence or processing the signal values obtained in the step (a) by using a first reference value to extract the signal for the second target nucleic acid sequence; wherein the first reference value is a value representing a relationship of change in signals provided by the first signal-generating means at the relatively high detection temperature and the relatively low detection temperature, and the second reference value is a value representing a relationship of change in signals provided by the second signal-generating means at the relatively high detection temperature and the relatively low detection temperature; wherein the first reference value is determined from a control reaction using the first target nucleic acid sequence and the first signal-generating means and the second reference value is determined from a control reaction using the second target nucleic acid sequence and the second signal-generating means;
   (c) selecting a cycle having a maximum signal value or a minimum signal value in the extracted signal for the first target nucleic acid sequence or the second target nucleic acid sequence; and
   (d) providing a signal value(s) from the selected cycle to an end cycle as an analytical signal for determination of the presence of the first target nucleic acid sequence or the second target nucleic acid sequence.

2. The method of claim 1, which further comprises the following steps between the step (b) and the step (c):
   (bc-1) identifying whether the extracted signal satisfies an accuracy criterion; wherein the accuracy criterion is that the extracted signal does not cross a threshold; and
   (bc-2) proceeding to the step (c) when the extracted signal for the first target nucleic acid sequence or the second target nucleic acid sequence does not satisfy the accuracy criterion; or providing the extracted signal as an analytical signal without proceeding to the step (c) when the extracted signal for the first target nucleic acid sequence or the second target nucleic acid sequence satisfies the accuracy criterion.

3. The method of claim 1, wherein the selected cycle is a cycle having the minimum signal value when the suitably extracted signal for a target nucleic acid sequence exhibits an increasing signal pattern in the presence of the target nucleic acid sequence in a sample; or the selected cycle is a cycle having a maximum signal value when the suitably extracted signal for a target nucleic acid sequence exhibits a decreasing signal pattern in the presence of the target nucleic acid sequence in a sample.

4. The method of claim 1, wherein the method further comprises modifying the signal value(s) from the selected cycle to the end cycle prior to providing as the analytical signal.

5. The method of claim 4, wherein the modification comprises shifting the signal values from the selected cycle to the end cycle upward or downward.

6. The method of claim 1, wherein the method further comprises adjusting a signal value(s) from a first cycle to a cycle immediately before the selected cycle to the extent that the adjustment does not affect the determination of the presence of the first target nucleic acid sequence or the second target nucleic acid sequence and providing the adjusted signal value(s) in combination with the signal value(s) from the selected cycle to an end cycle as the analytical signal.

7. The method of claim 6, wherein the adjustment comprises adjusting the signal value(s) from the first cycle to the cycle immediately before the selected cycle to a background level.

8. The method of claim 6, wherein the adjustment comprises adjusting the signal value(s) from the first cycle to the cycle immediately before the selected cycle to be substantially identical to the signal value at the selected cycle.

9. The method of claim 6, wherein the method further comprises modifying the adjusted signal value(s) from the first cycle to the cycle immediately before the selected cycle and the signal value(s) from the selected cycle to the end cycle prior to providing as the analytical signal.

10. The method of claim 9, wherein the modification comprises shifting the adjusted signal value(s) from the first cycle to the cycle immediately before the selected cycle and the signal value(s) from the selected cycle to the end cycle upward or downward.

11. The method of claim 1, wherein the first signal-generating means generates signals at the relatively high detection temperature and the relatively low detection temperature and the second signal-generating means generates a signal at the relatively low detection temperature.

12. The method of claim 11, wherein the processing of the signal values in the step (b) comprises mathematically processing the signal values by using the first reference value to extract the signal for the second target nucleic acid sequence from the signals at the relatively low detection temperature in the step (a).

13. The method of claim 11, wherein the processing of the signal values in the step (b) comprises mathematically processing the signal values by using the first reference value to extract the signal for the second target nucleic acid sequence from the signal at the relatively high detection temperature in the step (a).

14. The method of claim 1, wherein the two signal-generating means generate signals at the relatively high detection temperature and the relatively low detection temperature.

15. The method of claim 14, wherein the second reference value is greater than the first reference value; wherein (i) the processing of the signal values in the step (b) comprises mathematically extracting the signal for the second target nucleic acid sequence from the signal at the relatively low detection temperature in the step (a) by using the first reference value; (ii) the processing of the signal values in the step (b) comprises mathematically extracting the signal for the second target nucleic acid sequence from the signal at the relatively high detection temperature in the step (a) by using the first reference value; (iii) the processing of the signal values in the step (b) comprises mathematically extracting the signal for the first target nucleic acid sequence from the signal at the relatively low detection temperature in the step (a) by using the second reference value; or (iv) the processing of the signal values in the step (b) comprises mathematically extracting the signal for the first target nucleic acid sequence from the signal the signal at the relatively high detection temperature in the step (a) by using the second reference value.

16. A computer readable storage medium containing instructions to configure a processor to perform a method for providing an analytical signal for a target nucleic acid sequence in a sample, the method comprising:
(a) receiving signals from the sample at a relatively high detection temperature and a relatively low detection temperature; wherein the first target nucleic acid sequence in the sample is detected by a first signal-generating means and the second target nucleic acid sequence in the sample is detected by a second signal-generating means; wherein the detection is performed at one or more cycles of the signal-generating process to obtain a signal value at each of the one or more cycles; wherein the two signals to be generated by the two signal-generating means are not differentiated by a single type of detector;
(b) processing the signal values obtained in the step (a) by using a second reference value to extract the signal for the first target nucleic acid sequence or processing the signal values obtained in the step (a) by using a first reference value to extract the signal for the second target nucleic acid sequence; wherein the first reference value is a value representing a relationship of change in signals provided by the first signal-generating means at the relatively high detection temperature and the relatively low detection temperature, and the second reference value is a value representing a relationship of change in signals provided by the second signal-generating means at the relatively high detection temperature and the relatively low detection temperature; wherein the first reference value is determined from a control reaction using the first target nucleic acid sequence and the first signal-generating means and the second reference value is determined from a control reaction using the second target nucleic acid sequence and the second signal-generating means;
(c) selecting a cycle having a maximum signal value or a minimum signal value in the extracted signal for the first target nucleic acid sequence or the second target nucleic acid sequence; and
(d) providing a signal value(s) from the selected cycle to an end cycle as an analytical signal for determination of the presence of the first target nucleic acid sequence or the second target nucleic acid sequence.

17. A device for providing an analytical signal for a target nucleic acid sequence in a sample, comprising (a) a computer processor and (b) the computer readable storage medium of claim 16 coupled to the computer processor.

* * * * *

SEQUENCE LISTING

```
<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: NG_F
<220> FEATURE:
<221> NAME/KEY: misc_feature
<222> LOCATION: (22)..(26)
<223> OTHER INFORMATION: n denotes deoxyinosine

<400> SEQUENCE: 1
tacgcctgct actttcacgc tnnnnngtaa tcagatg                              37

<210> SEQ ID NO 2
<211> LENGTH: 37
<212> TYPE: DNA
<213> ORGANISM: Artificial Sequence
<220> FEATURE:
<223> OTHER INFORMATION: NG_R
<220> FEATURE:
<221> NAME/KEY: misc_feature
<222> LOCATION: (22)..(26)
<223> OTHER INFORMATION: n denotes deoxyinosine

<400> SEQUENCE: 2
caatggatcg gtatcactcg cnnnnncgag caagaac                              37

<210> SEQ ID NO 3
<211> LENGTH: 34
<212> TYPE: DNA
<213> ORGANISM: Artificial Sequence
<220> FEATURE:
<223> OTHER INFORMATION: NG_PTO

<400> SEQUENCE: 3
gtacgcgata cgggcccctc attggcgtgt ttcg                                 34

<210> SEQ ID NO 4
<211> LENGTH: 39
<212> TYPE: DNA
<213> ORGANISM: Artificial Sequence
<220> FEATURE:
<223> OTHER INFORMATION: NG_CTO

<400> SEQUENCE: 4
tttttttttt ttttttttg tactgcccgt atcgcgtac                             39

<210> SEQ ID NO 5
<211> LENGTH: 40
<212> TYPE: DNA
<213> ORGANISM: Artificial Sequence
<220> FEATURE:
<223> OTHER INFORMATION: CT_F
<220> FEATURE:
<221> NAME/KEY: misc_feature
<222> LOCATION: (26)..(30)
```

<223> OTHER INFORMATION: n denotes deoxyinosine

<400> SEQUENCE: 5
gagttttaaa atgggaaatt ctggtnnnnn tttgtataac                            40

<210> SEQ ID NO 6
<211> LENGTH: 40
<212> TYPE: DNA
<213> ORGANISM: Artificial Sequence
<220> FEATURE:
<223> OTHER INFORMATION: CT_R
<220> FEATURE:
<221> NAME/KEY: misc_feature
<222> LOCATION: (26)..(30)
<223> OTHER INFORMATION: n denotes deoxyinosine

<400> SEQUENCE: 6
ccaattgtaa tagaagcatt ggttgnnnnn ttattggaga                            40

<210> SEQ ID NO 7
<211> LENGTH: 39
<212> TYPE: DNA
<213> ORGANISM: Artificial Sequence
<220> FEATURE:
<223> OTHER INFORMATION: CT_PTO

<400> SEQUENCE: 7
gattacgcga ccgcatcaga agctgtcatt ttggctgcg                             39

<210> SEQ ID NO 8
<211> LENGTH: 39
<212> TYPE: DNA
<213> ORGANISM: Artificial Sequence
<220> FEATURE:
<223> OTHER INFORMATION: CT_CTO

<400> SEQUENCE: 8
gcgctggata ccctggacga tatgtgcggt cgcgtaatc                             39

<210> SEQ ID NO 9
<211> LENGTH: 22
<212> TYPE: DNA
<213> ORGANISM: Artificial Sequence
<220> FEATURE:
<223> OTHER INFORMATION: NG_P

<400> SEQUENCE: 9
tgcccctcat tggcgtgttt cg                                               22

<210> SEQ ID NO 10
<211> LENGTH: 36
<212> TYPE: DNA
<213> ORGANISM: Artificial Sequence
<220> FEATURE:
<223> OTHER INFORMATION: CT2_F
<220> FEATURE:
<221> NAME/KEY: misc_feature
<222> LOCATION: (22)..(26)
<223> OTHER INFORMATION: n denotes deoxyinosine

<400> SEQUENCE: 10
tccgaatgga taaagcgtga cnnnnnatga actcac                                36

<210> SEQ ID NO 11
<211> LENGTH: 37
<212> TYPE: DNA
<213> ORGANISM: Artificial Sequence

```
<220> FEATURE:
<223> OTHER INFORMATION: CT2_R
<220> FEATURE:
<221> NAME/KEY: misc_feature
<222> LOCATION: (23)..(27)
<223> OTHER INFORMATION: n denotes deoxyinosine

<400> SEQUENCE: 11
aacaatgaat cctgagcaaa ggnnnnncgt tagagtc                              37

<210> SEQ ID NO 12
<211> LENGTH: 29
<212> TYPE: DNA
<213> ORGANISM: Artificial Sequence
<220> FEATURE:
<223> OTHER INFORMATION: CT2_P

<400> SEQUENCE: 12
cattgtaaag atatggtctg cttcgaccg                                      29
```